United States Patent
Imamura et al.

(10) Patent No.: US 6,855,472 B2
(45) Date of Patent: Feb. 15, 2005

(54) POLYHYDROXYALKANOATE, PRODUCING METHOD THEREFOR, CHARGE CONTROL AGENT CONTAINING SUCH POLYHYDROXYALKANOATE, TONER CONTAINING SUCH CONTROL AGENT AND IMAGE FORMING METHOD AND IMAGE FORMING APPARATUS UTILIZING SUCH TONER

(75) Inventors: Takeshi Imamura, Kanagawa (JP); Etsuko Sugawa, Kanagawa (JP); Tetsuya Yano, Kanagawa (JP); Takashi Kenmoku, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 251 days.

(21) Appl. No.: 10/133,379

(22) Filed: Apr. 29, 2002

(65) Prior Publication Data

US 2003/0073804 A1 Apr. 17, 2003

(30) Foreign Application Priority Data

Apr. 27, 2001 (JP) .......................... 2001-131693
Apr. 27, 2001 (JP) .......................... 2001-131811

(51) Int. Cl.$^7$ .......................... G03G 9/08; C12P 11/00; C08C 75/00
(52) U.S. Cl. .................. 430/109.4; 528/360; 528/361; 528/364; 430/108.4; 430/108.5; 430/109.1; 430/137.1; 430/238; 430/445; 435/130; 435/136; 435/137; 435/139; 435/140; 435/146; 435/252.34; 435/252.4; 435/255.1; 339/222
(58) Field of Search .......................... 430/108.4, 108.5, 430/109.1, 109.4, 137.1, 238, 445; 528/360, 361, 364; 435/130, 136, 137, 139, 140, 146, 252.34, 252.4, 255.1; 339/222

(56) References Cited

U.S. PATENT DOCUMENTS 4,393,167 A  7/1983  Holmes et al. ............... 525/64
4,442,189 A  4/1984  Lu et al. ...................... 430/45
4,480,021 A  10/1984  Lu et al. ..................... 430/106
4,795,690 A  1/1989  Shindo et al. .............. 430/109
4,876,331 A  10/1989  Doi ............................ 528/361
4,925,765 A  5/1990  Madeleine .................. 430/110
5,004,664 A  4/1991  Fuller et al. ................. 43/106
5,135,859 A  8/1992  Witholt et al. .............. 435/135

(List continued on next page.)

FOREIGN PATENT DOCUMENTS

JP      63-38958    2/1985
JP      60-108861   6/1985
JP      61-3149     11/1986

(List continued on next page.)

OTHER PUBLICATIONS

Stelnbüchel, et al., "Diversity of bacterial polyhydroxyalkanoic acids", FEMS Microbiology Letters, vol. 128, pp. 219–228 (1995).

Takagi, et al., "Biosynthesis of Polyhydroxyalkanoate with a Thiophenoxy Side Group Obtained from *Pseudomonas putida*"; Macromolecules 32 (1999), 8315–8318.

Park, et al., "Epoxidation of Bacterial Polyesters with Unsaturated Side Chains. II. Rate of Epoxidation and Polymer Properties"; J. Polym. Sci., Part A, Polymer Chemistry. 36 (1998), 2381–2387.

(List continued on next page.)

*Primary Examiner*—Samuel A. Acquah
(74) *Attorney, Agent, or Firm*—Fitzpatrick, Cella, Harper and Scinto

(57) ABSTRACT

The invention is to provide polyhydroxyalkanoate of a novel structure enabling application to wider fields, and a producing method therefor. The invention also provides a biodegradable charge control agent having excellent charging characteristics, excellent dispersibility in the toner resin and improved spent property. The polyhydroxyalkanoate of the present invention is featured by including, in the polymer molecule, a units represented by the general formulas (1) and (2) and at least one of the units represented by the general formulas (3) to (6).

30 Claims, 8 Drawing Sheets

U.S. PATENT DOCUMENTS

| | | | |
|---|---|---|---|
| 5,200,332 A | 4/1993 | Yamane et al. | 435/135 |
| 5,292,860 A | 3/1994 | Shiotani et al. | 528/361 |
| 5,612,161 A | 3/1997 | Watanabe et al. | 430/110 |
| 5,667,927 A | 9/1997 | Kubota et al. | 430/109 |
| 6,266,272 B1 | 7/2001 | Kirihata et al. | 365/185.08 |

FOREIGN PATENT DOCUMENTS

| | | |
|---|---|---|
| JP | 63-88564 | 4/1988 |
| JP | 5-7492 | 1/1993 |
| JP | 5-93049 | 4/1993 |
| JP | 6-15604 | 3/1994 |
| JP | 6-289644 | 10/1994 |
| JP | 7-14352 | 2/1995 |
| JP | 7-72658 | 3/1995 |
| JP | 7-120975 | 5/1995 |
| JP | 7-265065 | 10/1995 |
| JP | 8-19227 | 2/1996 |
| JP | 8-179564 | 7/1996 |
| JP | 8-262796 | 10/1996 |
| JP | 2623684 | 6/1997 |
| JP | 9-191893 | 7/1997 |
| JP | 2642937 | 8/1997 |
| JP | 9-274335 | 10/1997 |
| JP | 9-2871746 | 10/1997 |
| JP | 2807795 | 10/1998 |
| JP | 2989175 | 12/1999 |
| JP | 2001-057085 | 12/1999 |

OTHER PUBLICATIONS

Gross et al., "Cyanophenoxy–Containing Microbial Polyesters: Structural Analysis, Th rmal Properties, Second Harmonic Generation and In–Vivo Biodegradability"; Polymer International, 39 (1996), 205–213.

Curl y, t al., "Production of Poly(3–hydroxyalkanoates) Containing Aromatic Substitu nts by *Pseudomonas oleovarans*"; Macromolecul s, 29, (1996), 1762–1766.

Fritzsche, et al., "An unusual bacterial polyester with a phenyl pendant group"; Makromol. Chem., 191 (1990), 1957–1965.

Kim, et al., "Preparation and Characterization of Poly(β–hydroxyalkanoat s) Obtained from *Pseudomonas oleovorans* Grown with Mixtures of 5–Phenylval ric Acid and n–Alkanoic Acids"; Macromolecul s, 24 (1991), 5256–5260.

Kim, et al., "Bioengineering of poly(β–hydroxyalkanoates) for advanced material applications: incorporation of cyano and nitrophenoxy side chain substituents"; Can. J. Microbiol., 41 (1995), (Suppl. 1): 32–43.

Arostegui, et al., "Bacterial Polyesters Produced by *Pseudomonas oleovorans* Containing Nitrophenyl Groups"; Macromolecules, 32, No. 9, (1999), 2889–2895.

Ritter, et al., "Bacterial production of polyesters bearing phenoxy groups in the side chians, 1"; Micromol. Chem. Phys., 195 (1994) 1165–1672.

Park, et al., "Epoxidation of Bacterial Polyesters with Unsaturated Side Chains. I. Production and Epoxidation of Polyester from 10–Undecenoic Acid"; Macromolecules 31, 5, 1480–1486 (1998).

POLYHYDROXYALKANOATE, PRODUCING METHOD THEREFOR, CHARGE CONTROL AGENT CONTAINING SUCH POLYHYDROXYALKANOATE, TONER CONTAINING SUCH CONTROL AGENT AND IMAGE FORMING METHOD AND IMAGE FORMING APPARATUS UTILIZING SUCH TONER

BACKGROUND OF THE INVENTION

1. Field of the Invention

The present invention relates to polyhydroxyalkanoate (PHA) containing novel a constituent unit and a producing method therefor. More specifically, it relates to a method for producing biodegradable novel PHA containing a 3-hydroxy alkanoic acid unit having 2-thienylsulfinyl radical and 2-thienylsulfonyl radical as substituents at the end of the side chain by culturing a microorganism having the PHA producing ability thereby producing and accumulating therein PHA containing 3-hydroxy alkanoic acid unit having corresponding 2-thienylsulfonyl radical as the substituent, and selectively oxidizing sulfur of sulfide type in such PHA thereby converting it into sulfonyl radical and sulfinyl radical.

The present invention also relates to a charge control agent, a toner binder and an electrostatic latent image developing toner to be used in a recording method utilizing an electrophotographic method, an electrostatic recording method, a magnetic recording method etc., and an image forming method and an image forming apparatus utilizing such toner. In particular, it relates to a charge control agent, a toner binder, an electrostatic latent image developing toner, an image forming method and an image forming apparatus to be employed in electrophotography, electrostatic recording, electrostatic printing such as a copying apparatus, a printer or a facsimile in which an image is formed by forming in advance a toner image on an electrostatic latent image bearing member (hereinafter simply called image bearing member) and then transferring such toner image onto a transfer material. More specifically, it relates to a negatively chargeable charge control agent, a toner binder and an electrostatic latent image developing toner utilizing the same, and an image forming method and an image forming apparatus utilizing such toner.

2. Description of the Related Art

It has already been reported that various microorganisms produce poly-3-hydroxybutyric acid (PHB) or other PHA's and accumulate such products therein ("Biodegradable Plastics Handbook", edited by Biodegradable Plastics Association, N.T.S.Co., p. 178–197 (1995)). Such PHA produced by the microorganisms can be utilized for producing various products for example by fusion, like the conventional plastics. Also the PHA produced by microorganisms, being biodegradable, has the advantage that it can be completely decomposed by the microorganisms in a nature, and, unlike the various conventional synthesized polymers, is free from contamination resulting from remaining in the natural environment. It also shows satisfactory matching with the living tissues and is expected in the applications as the soft material for medical use.

Such microorganism-produced PHA is known to assume various compositions or structures depending on the kind of microorganism, composition of culture medium and culture condition employed for production, and researches have been made for controlling such composition and structure, principally for improving the physical properties of PHA.

[1] At first, for the biosynthesis of PHA by polymerizing a monomer unit of relatively simple structure such as 3-hydroxybutyric acid (hereinafter abbreviated as 3HB), following references are known:

(a) PHA containing 3HB and 3-hydroxyvaleric acid (hereinafter abbreviated as 3HV) as monomer units:
Japanese Patent Publications Nos. 6-15604, 7-14352 and 8-19227, and Japanese Patent Application Laid-open No. 5-7492;

(b) PHA containing 3HB and 3-hydroxyhexanoic acid (hereinafter abbreviated as 3HHx) as monomer units:
Japanese Patent Applications Laid-open Nos. 5-93049 and 7-265065;

(c) PHA containing 3HB and 4-hydroxybutyric acid (hereinafter abbreviated as 4HB) as monomer units:
Japanese Patent Application Laid-open No. 9-191893;

(d) PHA containing 3-hydroxyalkanoate of 6 to 12 carbon atoms as monomer unit:
Japanese Patent No. 2642937; and (e) biosynthesis of PHA utilizing a single fatty acid as the carbon source, providing PHA substantially same as (d):
Appl. Environ. Microbiol., 58(2), 746(1992).

All these references report production of PHA consisting of a monomer unit having an alkyl radical in the side chain, namely "usual PHA", synthesized by β-oxidation of hydrocarbon or the like by microorganisms or by fatty acid synthesis from saccharide.

[2] However, for wider application of microorganism-produced PHA, for example for application as functional polymer, PHA having a substituent other than alkyl radical in the side chain, namely "unusual PHA", is anticipated to be extremely useful. Examples of hopeful substituent for this purpose include a radical containing an aromatic ring (phenyl radical, phenoxy radical, benzoyl radical etc.), an unsaturated hydrocarbon radical, an ester radical, an allyl radical, a cyano radical, a halogenated hydrocarbon radical and an epoxide present on the side chain. Among these, PHA having an aromatic ring on the side chain is actively investigated. For biosynthesis of PHA having an aromatic ring on the side chain, there are known following references:

(a) PHA containing phenyl radical or a partially substituted radical thereof (substituted phenyl radical etc.):
Makromol. Chem. 191, 1957–1965(1990) and Macromolecules, 24, 5256–5260(1991) report that *Pseudomonas oleovorans* produces PHA containing 3-hydroxy-5-phenylvaleric acid as a unit, from 5-phenylvaleric acid as substrate.
Also Macromolecules, 29, 1762–1766(1996) reports that *Pseudomonas oleovorans* produces PHA containing 3-hydroxy-5-(p-tolyl) valeric acid as a unit, from 5-(p-tolyl) valeric acid as substrate.
Also Macromolecules, 32, 2889–2895(1999) reports that *Pseudomonas oleovorans* produces PHA containing 3-hydroxy-5-(2,4-dinitrophenyl) valeric acid and 3-hydroxy-5-(p-nitrophenyl) valeric acid as units, from 5-(2,4-dinitrophenyl) valeric acid as substrate.

(b) PHA containing phenoxy radical or partially substituted radical thereof (such as substituted phenoxy radical):
Macromol. Chem. Phys., 195, 1665–1672(1994) reports that *Pseudomonas oleovorans* produces a PHA copolymer containing 3-hydroxy-5-pnenoxyvaleric acid and 3-hydroxy-9- phenoxynonaic acid as the units, from 11-phenoxyundecanoic acid as substrate.

Also Japanese Patent No. 2989175 discloses inventions relating to homopolymer consisting of a 3-hydroxy-5-(monofluorophenoxy) pentanoate (3H5(MFP)P) unit or a 3-hydroxy-5-(difluorophenoxy) pentanoate (3H5(DFP)P) unit, copolymer containing at least a 3H5(MFP)P unit or a 3H5(DFP)P unit, a novel strain of *Pseudomonas putida* capable of producing these polymers, and a method for producing the aforementioned polymers utilizing *Pseudomonas* genus. This patent specification teaches, as the effects of such inventions, that PHA polymer having a phenoxy radical substituted with 1 or 2 fluorine atoms at the end of the side chain can be biosynthesized from a long-chain fatty acid having a substituent and that thus produced PHA has a high melting point and is capable of providing stereoregularity and water repellency while maintaining satisfactory working properties.

In addition to the partially substituted phenoxy radical having fluorine substituent on the ring, there are also investigated partially substituted radical having cyano or nitro radical on the ring.

Can. J. Microbiol., 41, 32–43(1995) and Polymer International, 39, 205–213(1996) report production of PHA containing 3-hydroxy-6-(p-cyanophenoxy) hexanoic acid or 3-hydroxy-6-(p-nitrophenoxy) hexanoic acid as the monomer unit by *Pseudomonas oleovorans* ATCC 29347 strain and *Pseudomonas putida* KT2442 stain, from octanoic acid and 6-(p-cyanophenoxy) hexanoic acid or 6-(p-nitrophenoxy) hexanoic acid as substrate.

These references relate to PHA having an aromatic ring on the side chain, instead of the usual PHA in which the side chain consists of an alkyl radical, and are effective in obtaining polymer of physical properties resulting from such aromatic ring.

[3] Also as a new category not limited to changes in the physical properties, investigation is also made for producing PHA having an appropriate functional radical on the side chain, thereby obtaining PHA with new functions utilizing such substituent.

For example Macromolecules, 31, 1480–1486(1996) and Journal of Polymer Science: Part A: Polymer Chemistry, 36, 2381–2387(1998) etc. report a method of biosynthesizing PHA containing a unit having vinyl radical at the end of the side chain and then executing epoxylation with an oxidant, thereby obtaining PHA having a high reactive epoxy radical at the end of the side chain.

In addition to such vinyl radical, for biosynthesis of PHA containing a unit having sulfide type sulfur (—S—) for which high reactivity is anticipated, Macromolecules, 32, 8315–8318(1999) reports that *Pseudomonas putida* 27N01 strain produces PHA copolymer containing 3-hydroxy-5-(phenylsulfanyl) valeric acid and 3-hydroxy-7-(phenylsulfanyl) heptanoic acid as the units, from 11-(phenylsulfanyl) valeric acid as substrate.

On the other hand, the conventional electrophotography includes various methods so far proposed but in general consists of forming an electrical latent image by various means on an image bearing member (photosensitive member) utilizing a photoconductive substance, then developing such latent image with toner to obtain a visible image, transferring the toner image onto a transfer material such as paper if necessary, and fixing the toner image on the transfer material with heat and/or pressure thereby obtaining a copy. For rendering the electrical latent image visible, there are known cascade development method, magnetic brush development method, pressure development method etc. Also there is utilized a method of employing magnetic toner and a rotary developing sleeve having magnetic poles at the center, and causing the magnetic toner to fly from the developing sleeve to the photosensitive member.

For developing electrostatic latent image, there are known a two-component development method employing two-component developer consisting of toner and carrier, and a one-component development method employing one-component developer consisting solely of toner and not containing carrier.

The colored fine particles, generally called toner, are essentially composed of binder resin and a coloring material, and also contain magnetic powder etc. if necessary. For providing the toner with electric charge, there can be utilized charging characteristics of the binder resin itself without utilizing the charge control agent, but satisfactory image quality cannot be obtained because of insufficiency in stability of charge in time and in moisture resistance. Therefore, a charge control agent is added to the toner in order to retain and control the charge.

The charge control agents presently known in this technical field include, for example for negative triboelectricity, metal complexes of azo dyes, those of aromatic dicarboxylic acid, and those of salycilic acid derivatives. Also for positive charge control agents, there are known nigrosin dyes, triphenylmethane dyes, various quaternary ammonium salts and organic tin compounds such as tibutyltin oxide.

From the standpoint of environmental protection, it is recently desired worldwide to further reduce the wastes and the environmental pollution. Such requirements are same also in the electrophotography. In fact the discarded amount of the printed papers, waste toner after use and copy papers is increasing year after year with the popularization of the imaging apparatuses, and, from the standpoint of securing the global environment, it is strongly desired to further reduce the wastes and to use substances selected in consideration of the environment.

In order to meet such requirements, there are investigated charge control agents consisting of colorless compounds free from heavy metals or of polymers. Examples of such compounds include those disclosed in the U.S. Pat. Nos. 4,480,021, 4,442,189 and 4,925,765, and the Japanese Patent Applications Laid-open Nos. 60-108861, 61-3149, 63-38958 and 63-88564, but such compounds are not sufficient in the performances of the charge control agent, for example in the charge amount, start-up characteristics of charging, stability in time and environmental stability. In general the polymer charge control agent for providing the toner with the negative charging property is often composed of copolymer of styrene and/or α-methylstyrene and alkyl (meth)acrylate ester or alkyl(meth)acrylate amide having a sulfonic acid radical (Japanese Patent Applications Laid-open Nos. 7-72658 and 8-179564, and Japanese Patent Nos. 2114410, 2623684 and 2807795). Such materials are advantageous as they are colorless, but have to be added in a large amount in order to obtain the desired charge amount. Also the moisture resistance is anticipated to be insufficient since the sulfonic acid radical, serving as the anionic functional radical, apparently has hygroscopicity. Also there is anticipated insufficiency in the mutual solubility with the binding resin (binder) which is basically nonionic.

From the standpoint of environmental protection, developments are being made for biodegradable resin which can be decomposed in time by the function of microorganisms, and, as explained in the foregoing, there have been reported that various microorganisms produce and accumulate therein biodegradable resin having a polyester structure (PHA). Such PHA is known to assume various compositions or structures depending on the kind of microorganism, composition of culture medium and culture condition employed for production, and researches have been made for controlling such composition and structure, principally for improving the physical properties of PHA.

Also in the field of electrophotography, there has been proposed application of the biodegradable resin to the binder resin in the manufacture of toner. For example the U.S. Pat. No. 5,004,664 discloses toner containing biodegradable resin, in particular polyhydroxy butyric acid, polyhydroxy valeric acid, copolymer thereof or a blended substance thereof as a component. Also the Japanese Patent Application Laid-open No. 6-289644 discloses electrophotographic toner particularly for heat roller fixing, containing vegetable wax and biodegradable resin (for example microorganism-produced polyester, vegetable- or animal-derived natural polymer etc.), wherein the aforementioned vegetable wax is added to the binder resin in an amount of 5 to 50 mass %. Also the Japanese Patent Application Laid-open No. 7-120975 discloses electrophotographic toner containing butyric acid-based resin as the binder resin. Further, the Japanese Patent Application Laid-open No. 9-274335 discloses electrostatic latent image developing toner containing polyester resin, obtained by dehydration condensation-polymerization of a composition containing butyric acid and 3- or higher-functional oxycarboxylic acid, and a coloring agent. Also the Japanese Patent Application Laid-open No. 8-262796 discloses electrophotographic toner containing binder resin and a coloring agent, wherein the binder resin is composed of biodegradable resin (for example aliphatic polyester resin) and the coloring agent is composed of a water insoluble dyestaff. Also the Japanese Patent Application Laid-open No. 9-281746 discloses electrostatic image developing toner containing urethanized polyester resin, obtained by crosslinking polylactic acid with 3- or higher-functional polyvalent isocyanate, and a coloring agent. All these electrophotographic toners employ biodegradable resin as the binder resin, and are expected to be effective in contributing to securing the environment.

In any of the electrophotographic toners employing the aforementioned biodegradable resins as the binder resin, the charge control agent contains heavy metals such as chromium, cobalt, nickel, copper, zinc or iron. On the other hand, the use of biodegradable resin for the charge control agent has not been reported, and there is desired the material realizing further environmental protection.

SUMMARY OF THE INVENTION

Among the aforementioned PHA's having a functional radical on the side chain, let us consider PHA containing a 3-hydroxy-ω-(phenylsulfanyl) alkanoic acid unit. The sulfide-type sulfur (—S—) is strongly reactive, and, in the development of functional PHA's, various developments are expected toward various derivatives of PHA including sulfide-type sulfur (—S—). For the biosynthesis of such PHA containing an aromatic ring and sulfide-type sulfur (—S—), there is known only one reference mentioned in the foregoing. Thus, in the development of functional PHA's, there are desired various derivatives of PHA, derived from PHA containing sulfide-type sulfur (—S—).

In consideration of the foregoing, an object of the present invention is to provide PHA of a novel structure adaptable to wider applications, namely capable of further improving the physicochemical properties of PHA, instead of the PHA containing a unit having sulfide-type sulfur (—S—) in the side chain, and a producing method therefor. More specifically, an object of the present invention is to provide PHA of a novel structure obtained by employing PHA principally containing a 3-hydroxy-ω-(thienylsulfanyl) alkanoic acid unit and produced by microorganisms as an intermediate raw material, converting the sulfide-type sulfur (—S—) thereof into another sulfur-containing radical, and applying chemical modification to the methylene portion of the side chain thereby also changing the chemical structure, and a producing method therefor.

Also in consideration of the foregoing, another object of the present invention is to provide a negatively chargeable charge control agent which is colorless and free from metals in the functionality and provides higher performance (at least one of higher charge amount, faster rise of charging, superior stability in time and higher environmental stability) and improved dispersibility, toner binder containing such charge control agent, electrostatic latent image developing toner containing such charge control agent, and an image forming method utilizing such electrostatic charge developing toner.

As a result of intensive investigations for attaining the aforementioned objects, the present inventors have found that PHA of a novel structure can be obtained and the physicochemical properties of PHA can be further improved by employing PHA principally containing a 3-hydroxy-ω-(thienylsulfanyl) alkanoic acid unit and produced by microorganisms as an intermediate raw material, and employing oxidation with sodium hypochlorite for oxidizing the sulfide-type sulfur (—S—) thereof thereby converting it into a sulfinyl radical (—SO—) and a sulfonyl radical (—SO$_2$—). It is also found that such PHA contains not only the aforementioned conversion into sulfinyl radical (—SO—) and sulfonyl radical (—SO$_2$—) but also contains, as subsidiary units, a chloro-substituted unit including chloro-substitution on a carbon atom adjacent to the sulfonyl radical (—SO$_2$—) or a chloro-substituted unit including chloro-substitution on a carbon atom adjacent to the partially oxidized sulfinyl radical (—SO—). Also the present inventors have found that the desired PHA principally containing sulfinyl radical (—SO—) and sulfonyl radical (—SO$_2$—) by causing the microorganisms to produce, from ω-(2-thienylsulfanyl)-alkanoic acid used as the starting raw material, PHA principally containing 3-hydroxy-ω-(phenylsulfanyl) alkanoic acid unit an intermediate raw material, and, instead of executing a step of separation and purification thereof by solvent extraction and then an aforementioned oxidation step utilizing sodium hypochlorite, by applying a process utilizing sodium hypochlorite directly on the microorganism cells or by separating PHA accumulated in the microorganism cells by pulverizing such cells and then executing a process utilizing sodium hypochlorite. Based on such findings, the present inventors have reached the present invention.

More specifically, the polyhydroxyalkanoate of the present invention is featured by including, in the polymer molecule, a unit represented by the following general formula (1):

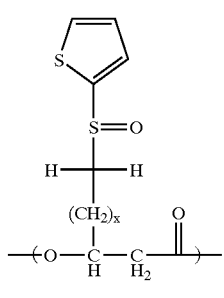

(1)

X = 0–8

(wherein x stands for an integer selected within a range of 0–8 indicated in the chemical formula, and such unit may be present at least one in the polymer);

a unit represented by the following general formula (2):

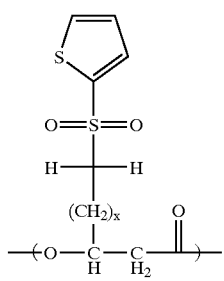

(2)

X = 0–8

(wherein x stands for an integer selected within a range of 0–8 indicated in the chemical formula, and such unit may be present at least one in the polymer); and at least one of the units represented by the following general formulas (3) to (6), namely:

a unit represented by the following general formula (3):

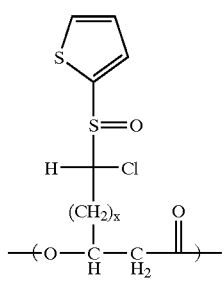

(3)

X = 0–8

(wherein x stands for an integer selected within a range of 0–8 indicated in the chemical formula, and such unit may be present at least one in the polymer);

a unit represented by the following general formula (4):

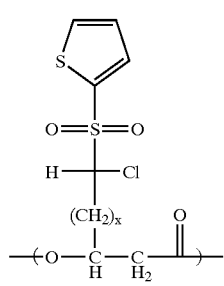

(4)

X = 0–8

(wherein x stands for an integer selected within a range of 0–8 indicated in the chemical formula, and such unit may be present at least one in the polymer);

a unit represented by the following general formula (5):

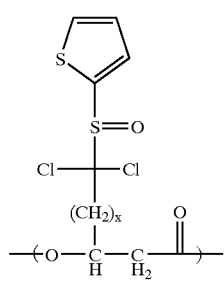

(5)

X = 0–8

(wherein x stands for an integer selected within a range of 0–8 indicated in the chemical formula, and such unit may be present at least one in the polymer); and a unit represented by the following general formula (6):

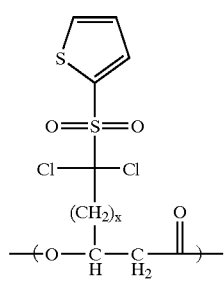

(6)

X = 0–8

(wherein x stands for an integer selected within a range of 0–8 indicated in the chemical formula, and such unit may be present at least one in the polymer). In such PHA of the present invention, in addition to the unit represented by the foregoing general formula (1), the unit represented by the foregoing general formula (2) and at least one of the units represented by the foregoing general formulas (3) to (6), there may be further included at least one of:

a unit represented by the following general formula (7):

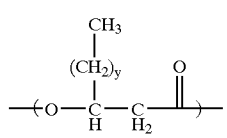

(7)

y = 0–8

(wherein y stands for an integer selected within a range of 0–8 indicated in the chemical formula, and such unit may be present at least one in the polymer); and a unit represented by the following general formula (8):

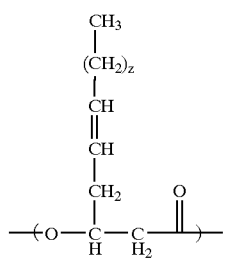

(8)

z = 3,5

(wherein z stands for an integer selected from 3 and 5). Also PHA of the present invention preferably has a number average molecular weight within a range of 1000 to 500000.

An embodiment of the PHA of the present invention of the aforementioned configuration may be polyhydroxyalkanoate featured by including:

a 3-hydroxy-5-(2-thienylsulfinyl) valeric acid unit represented by the following chemical formula (9):

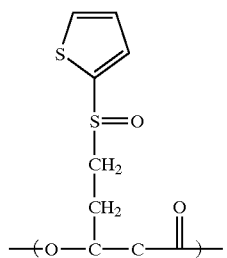

(9)

a 3-hydroxy-5-(2-thienylsulfonyl) valeric acid unit represented by the following chemical formula (10):

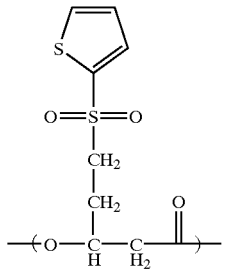

(10)

and at least one of the chloro-substituted units represented by the following chemical formulas (11) to (14), namely:

a 5-chloro-3-hydroxy-5-(2-thienylsulfinyl) valeric acid unit represented by the following chemical formula (11):

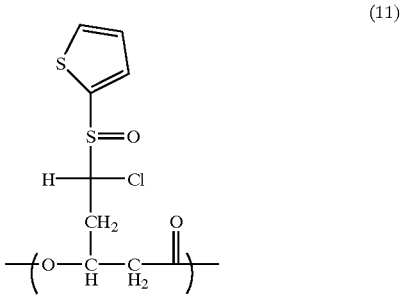

(11)

a 5-chloro-3-hydroxy-5-(2-thienylsulfonyl) valeric acid unit represented by the following chemical formula (12):

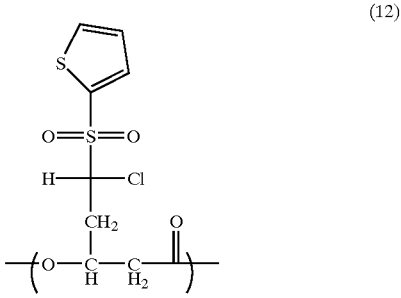

(12)

a 5,5-dichloro-3-hydroxy-5-(2-thienylsulfinyl) valeric acid unit represented by the following chemical formula (13):

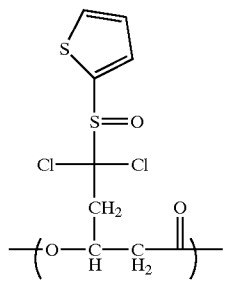

(13)

and a 5,5-dichloro-3-hydroxy-5-(2-thienylsulfonyl) valeric acid unit represented by the following chemical formula (14):

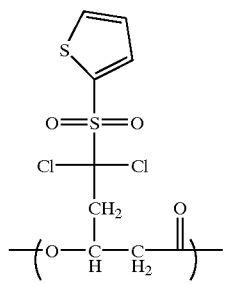

(14)

Furthermore, an embodiment of the PHA of the present invention may be polyhydroxyalkanoate featured by including, in the polymer molecule:

a 3-hydroxy-4-(2-thienylsulfinyl) butyric acid unit represented by the following chemical formula (15):

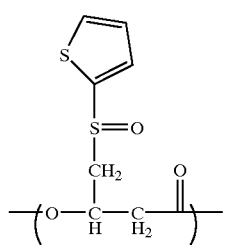

(15)

a 3-hydroxy-4-(2-thienylsulfonyl) butyric acid unit represented by the following chemical formula (16):

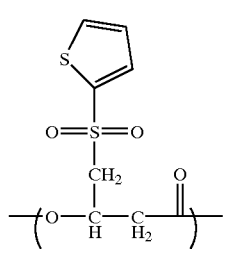

(16)

at least one of four chloro-substituted units represented by the following chemical formulas (17) to (20), namely:

a 4-chloro-3-hydroxy-4-(2-thienylsulfinyl) butyric acid unit represented by the following chemical formula (17):

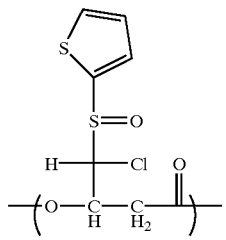

(17)

a 4-chloro-3-hydroxy-4-(2-thienylsulfonyl)-butyric acid unit represented by the following chemical formula (18):

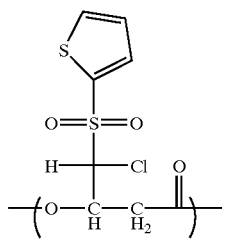

(18)

a 4,4-dichloro-3-hydroxy-4-(2-thienylsulfinyl)-butyric acid unit represented by the following chemical formula (19):

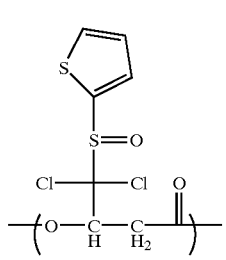

(19)

and a 4,4-dichloro-3-hydroxy-4-(2-thienylsulfonyl) butyric acid unit represented by the following chemical formula (20):

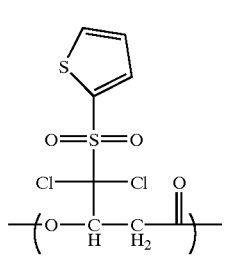

(20)

further a 3-hydroxy-6-(2-thienylsulfinyl)-hexanoic acid unit represented by the following chemical formula (21):

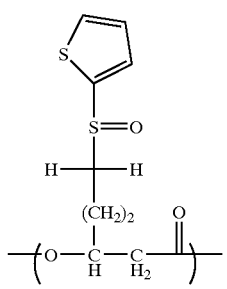

(21)

a 3-hydroxy-6-(2-thienylsulfonyl) hexanoic acid unit represented by the following chemical formula (22):

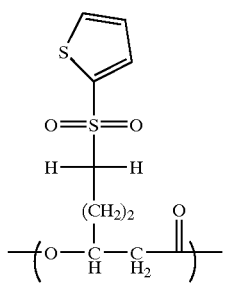

(22)

and at least one of the four chloro-substituted units represented in the following chemical formulas (23) to (26), namely:
a 6-chloro-3-hydroxy-6-(2-thienylsulfinyl)-hexanoic acid unit represented by the following chemical formula (23):

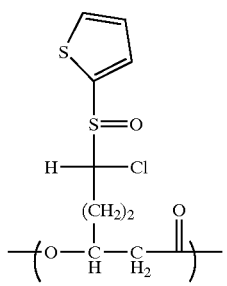

(23)

a 6-chloro-3-hydroxy-6-(2-thienylsulfonyl)-hexanoic acid unit represented by the following chemical formula (24):

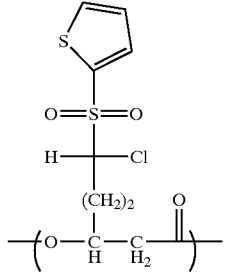

(24)

a 6,6-dichloro-3-hydroxy-6-(2-thienylsulfinyl)-hexanoic acid unit represented by the following chemical formula (25):

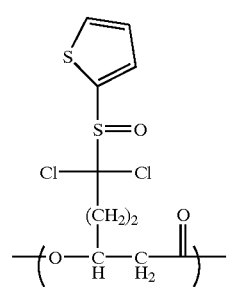

(25)

and a 6,6-dichloro-3-hydroxy-6-(2-thienylsulfonyl) hexanoic acid unit represented by the following chemical formula (26):

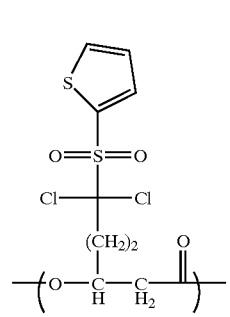

(26)

In addition, the present invention provides a method for producing the aforementioned PHA of the present invention. More specifically, the method of the present invention for producing polyhydroxyalkanoate is a method for producing polyhydroxyalkanoate having any of the aforementioned configurations, featured by including:

(step 1) a step of culturing microorganisms in a culture medium containing at least one of ω-(2-thienylsulfanyl) alkanoic acids represented by the following general formula (27)

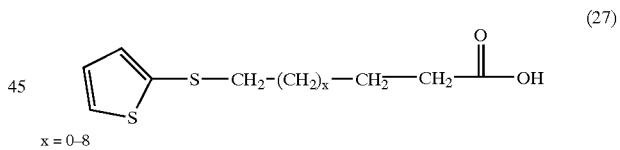

(27)

x = 0–8

(wherein x stands for an integer selected from a range of 0–8); and (step 2) a step of processing polyhydroxyalkanoate, produced by the microorganisms cultured in the step 1, with sodium hypochlorite.

In the PHA producing method of the present invention, between the aforementioned step 1 and step 2, there may be provided a step of separating polyhydroxyalkanoate produced by the microorganisms cultured in the step 1 from the cells of such microorganisms.

In such case, the step of separating polyhydroxyalkanoate produced by such microorganisms may include a step of pulverizing the microorganism cells. Such step for pulverizing the microorganism cells is preferably executed by an ultrasonic pulverizing method, a homogenizer method, a pressure pulverizing method, a beads impact method, a mechanical pulverizing method, a grinding method or a freezing-thawing method.

Otherwise, the step of separating polyhydroxyalkanoate produced by the microorganisms from the cells thereof may include a step of extracting polyhydroxyalkanoate from the microorganism cells with a solvent capable dissolving polyhydroxyalkanoate produced by the microorganisms. The aforementioned solvent capable of dissolving polyhydroxyalkanoate produced by the microorganisms is preferably at least one selected from chloroform, dichloromethane, dioxane, tetrahydrofurane, acetonitrile and acetone.

Furthermore, the PHA producing method of the present invention may be featured in that the culture medium employed in the step 1 contains polypeptone. It may also be featured in that the culture medium employed in the step 1 contains yeast extract. Otherwise, it may also be featured in that the culture medium employed in the step 1 contains saccharide. In such case, such saccharide is preferably at least one compound selected from a group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose and lactose.

Furthermore, the PHA producing method of the present invention may be featured in that the culture medium employed in the step 1 contains an organic acid or a salt thereof. In such case, the aforementioned organic acid or salt thereof is preferably at least a compound selected from a group consisting of pyruvic acid, malic acid, lactic acid, citric acid, succinic acid and salts thereof. Also the PHA producing method of the present invention may be featured in that the culture medium employed in the step 1 contains an amino acid or a salt thereof. In such case, the aforementioned amino acid or salt thereof is preferably at least a compound selected from a group consisting of glutamic acid, aspartic acid and salts thereof. In certain cases, the method may be featured in that the culture medium employed in the step 1 contains a straight-chain alkanoic acid with 4 to 12 carbon atoms or a salt thereof.

Also the PHA producing method of the present invention may be featured in that the culture of microorganisms in the step 1 includes:

(step 1-1) a step of culturing microorganisms in a culture medium containing at least one of ω-(2-thienylsulfanyl) alkanoic acids represented by the following general formula (27)

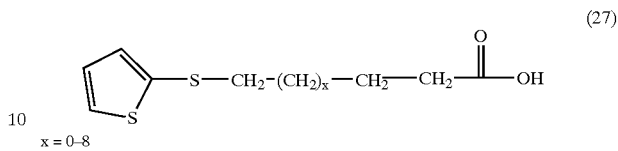

(27)

x = 0–8

(wherein x stands for an integer selected from a range of 0–8) and polypeptone; and (step 1-2) a step of further culturing the microorganisms, cultured in the step 1-1, in a culture medium containing at least one of ω-(2-thienylsulfanyl) alkanoic acids represented by the aforementioned general formula (27) and an organic acid or a salt thereof.

In such case, the aforementioned organic acid or salt thereof contained in the culture medium employed in the step 1-2 is preferably at least a compound selected from a group consisting of pyruvic acid, malic acid, lactic acid, citric acid, succinic acid and salts thereof. In such case it is further preferred that the culture medium employed in the step 1-2 does not contain nitrogen source.

Otherwise, in the PHA producing method of the present invention, the culture of microorganisms in the aforementioned step 1 may be featured by including:

(step 1-3) a step of culturing microorganisms in a culture medium containing at least one of ω-(2-thienylsulfanyl) alkanoic acids represented by the following general formula (27)

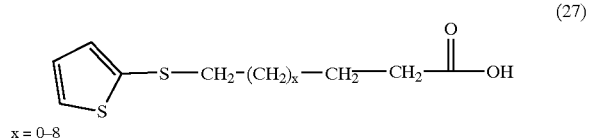

(27)

x = 0–8

(wherein x stands for an integer selected from a range of 0–8) and saccharide; and (step 1-4) a step of further culturing the microorganisms, cultured in the step 1-3, in a culture medium containing at least one of ω-(2-thienylsulfanyl) alkanoic acids represented by the aforementioned general formula (27) and saccharide but not containing a nitrogen source.

In such case, such saccharide is preferably at least one compound selected from a group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose and lactose. Also in such case, it is further preferred that the culture medium employed in the step 1-4 does not contain nitrogen source.

In addition, an embodiment of the PHA producing method of the present invention may be a method for producing polyhydroxyalkanoate which comprises culturing microorganisms, in the step 1, in a culture medium employing 5-(2-thienylsulfanyl) valeric acid represented by the following chemical formula (28):

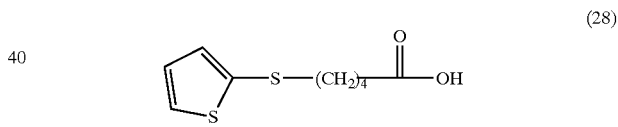

(28)

as ω-(2-thienylsulfanyl) alkanoic acid to be contained in the culture medium, and processing, with sodium hypochlorite in the step 2, the polyhydroxyalkanoate which the microorganisms, cultured in the step 1, produce from 5-(2-thienylsulfanyl) valeric acid represented by the aforementioned chemical formula (28), thereby producing polyhydroxyalkanoate containing, in the polymer molecule:

a 3-hydroxy-5-(2-thienylsulfinyl) valeric acid unit represented by the following chemical formula (9):

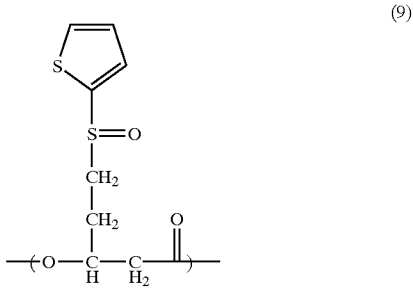

(9)

a 3-hydroxy-5-(2-thienylsulfonyl) valeric acid unit represented by the following chemical formula (10):

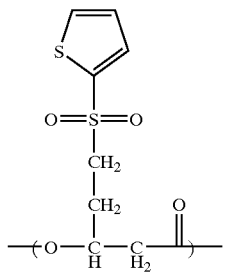

(10)

and at least one of the chloro-substituted units represented by the following chemical formulas (11) to (14), namely:

a 5-chloro-3-hydroxy-5-(2-thienylsulfinyl)-valeric acid unit represented by the following chemical formula (11):

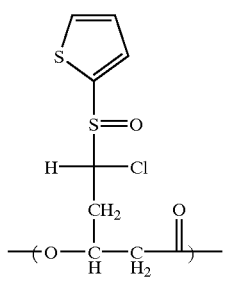

(11)

a 5-chloro-3-hydroxy-5-(2-thienylsulfonyl) valeric acid unit represented by the following chemical formula (12):

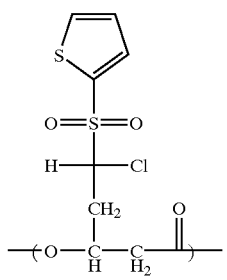

(12)

a 5,5-dichloro-3-hydroxy-5-(2-thienylsulfinyl) valeric acid unit represented by the following chemical formula (13):

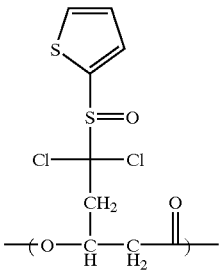

(13)

and a 5,5-dichloro-3-hydroxy-5-(2-thienylsulfonyl) valeric acid unit represented by the following chemical formula (14):

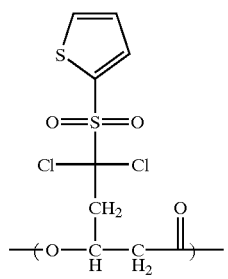

(14)

In addition, an embodiment of the PHA producing method of the present invention may be a method for producing polyhydroxyalkanoate which comprises culturing microorganisms, in the step 1, in a culture medium employing 6-(2-thienylsulfanyl) hexanoic acid represented by the following chemical formula (29):

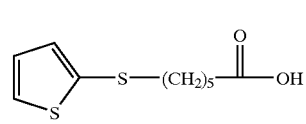

(29)

as ω-(2-thienylsulfanyl) alkanoic acid to be contained in the culture medium, and processing, with sodium hypochlorite in the step 2, the polyhydroxyalkanoate which the microorganisms, cultured in the step 1, produce from 6-(2-thienylsulfanyl) hexanoic acid represented by the aforementioned chemical formula (29), thereby producing polyhydroxyalkanoate containing, in the polymer molecule:

a 3-hydroxy-4-(2-thienylsulfinyl) butyric acid unit represented by the following chemical formula (15):

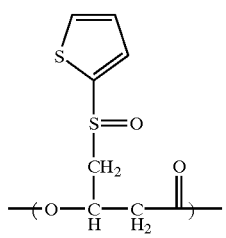

(15)

a 3-hydroxy-4-(2-thienylsulfonyl) butyric acid unit represented by the following chemical formula (16):

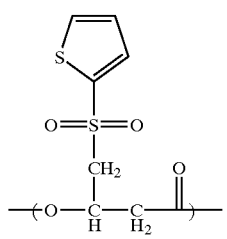
(16)

at least one of four chloro-substituted units represented by the following chemical formulas (17) to (20), namely:
a 4-chloro-3-hydroxy-4-(2-thienylsulfinyl) butyric acid unit represented by the following chemical formula (17):

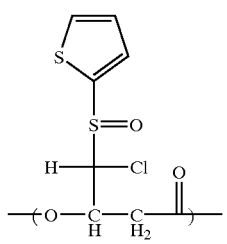
(17)

a 4-chloro-3-hydroxy-4-(2-thienylsulfonyl)-butyric acid unit represented by the following chemical formula (18):

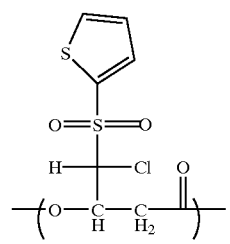
(18)

a 4,4-dichloro-3-hydroxy-4-(2-thienylsulfinyl)-butyric acid unit represented by the following chemical formula (19):

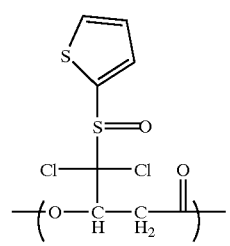
(19)

and a 4,4-dichloro-3-hydroxy-4-(2-thienylsulfonyl) butyric acid unit represented by the following chemical formula (20):

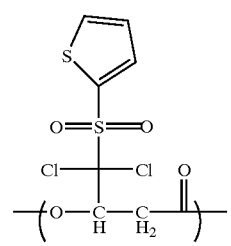
(20)

further a 3-hydroxy-6-(2-thienylsulfinyl)-hexanoic acid unit represented by the following chemical formula (21):

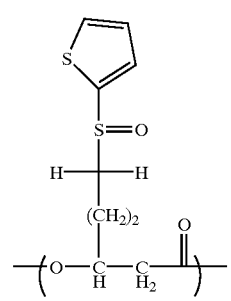
(21)

a 3-hydroxy-6-(2-thienylsulfonyl) hexanoic acid unit represented by the following chemical formula (22):

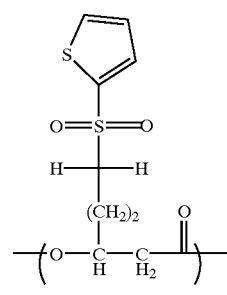
(22)

and at least one of the four chloro-substituted units represented in the following chemical formulas (23) to (26), namely:
a 6-chloro-3-hydroxy-6-(2-thienylsulfinyl)-hexanoic acid unit represented by the following chemical formula (23):

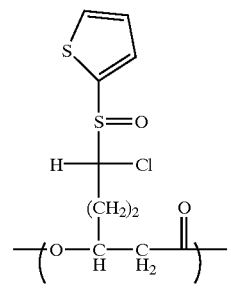
(23)

a 6-chloro-3-hydroxy-6-(2-thienylsulfonyl)-hexanoic acid unit represented by the following chemical formula (24):

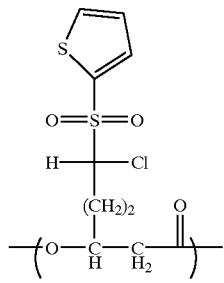

(24)

a 6,6-dichloro-3-hydroxy-6-(2-thienylsulfinyl)-hexanoic acid unit represented by the following chemical formula (25):

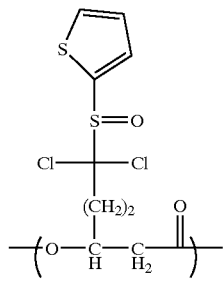

(25)

and a 6,6-dichloro-3-hydroxy-6-(2-thienylsulfonyl) hexanoic acid unit represented by the following chemical formula (26):

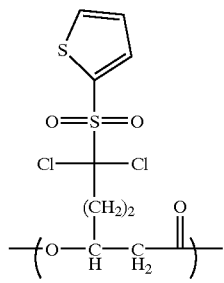

(26)

In the PHA producing method of the present invention, having the aforementioned configurations, the microorganisms to be employed in the step 1 are preferably those belonging to *Pseudomonas* genus. For example, the aforementioned microorganisms to be employed in the step 1 are preferably those of at least a strain selected from *Pseudomonas cichorii* YN2 (FERM BP-7375), *Pseudomonas cichorii* H45 (FERM BP-7374) and *Pseudomonas jessenii* P161 (FERM BP-7376).

Also as a result of intensive investigation for obtaining a charge control agent which is of high performance, substantially colorless and does not require use of a metal, the present inventors have reached the present invention.

More specifically, the present invention provides a charge control agent including polyhydroxyalkanoate featured by containing, in the polymer molecule, a unit represented by the following general formula (1):

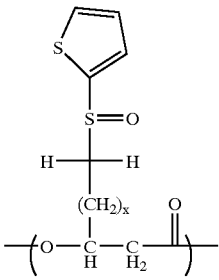

(1)

X = 0–8

(wherein x stands for an integer selected within a range of 0–8 indicated in the chemical formula, and such unit may be present at least one in the polymer);

a unit represented by the following general formula (2):

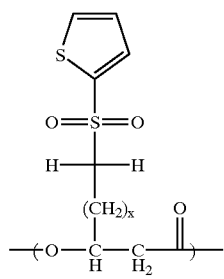

(2)

X = 0–8

(wherein x stands for an integer selected within a range of 0–8 indicated in the chemical formula, and such unit may be present at least one in the polymer); and at least one of the units represented by the following general formulas (3) to (6), namely:

a unit represented by the following general formula (3):

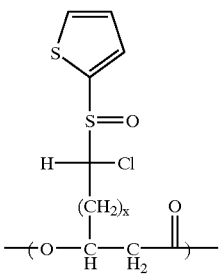

(3)

X = 0–8

(wherein x stands for an integer selected within a range of 0–8 indicated in the chemical formula, and such unit may be present at least one in the polymer);

a unit represented by the following general formula (4):

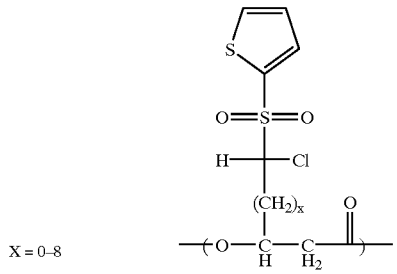

(4)

X = 0–8

(wherein x stands for an integer selected within a range of 0–8 indicated in the chemical formula, and such unit may be present at least one in the polymer);

a unit represented by the following general formula (5):

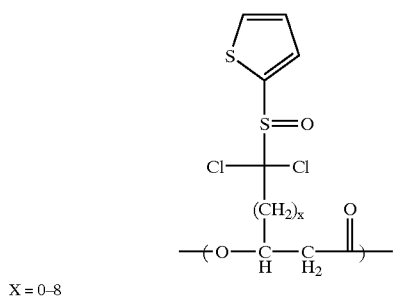

(5)

X = 0–8

(wherein x stands for an integer selected within a range of 0–8 indicated in the chemical formula, and such unit may be present at least one in the polymer); and a unit represented by the following general formula (6):

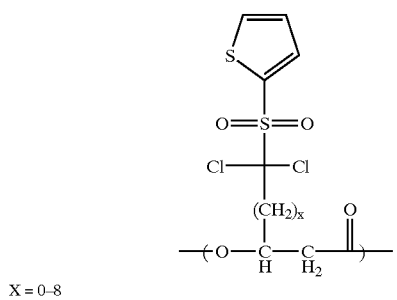

(6)

X = 0–8

(wherein x stands for an integer selected within a range of 0–8 indicated in the chemical formula, and such unit may be present at least one in the polymer).

Such PHA may further include at least one of:

a unit represented by the following general formula (7):

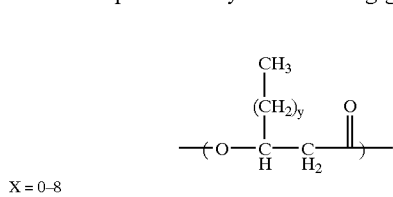

(7)

X = 0–8

(wherein y stands for an integer selected within a range of 0–8 indicated in the chemical formula, and such unit may be present at least one in the polymer); and a unit represented by the following general formula (8):

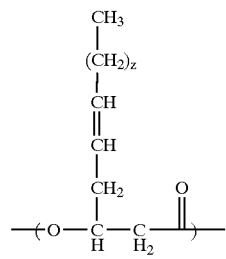

(8)

z = 3, 5

(wherein y and z may assume arbitrary integral values at least equal to 1 within the ranges shown in the chemical formulas, independently from the units represented by (1), (2), (3), (4), (5) and (6)).

Also PHA contained in the charge control agent of the present invention preferably has a number average molecular weight within a range of 1000 to 500000.

The present invention also provides toner binder containing the charge control agent of the present invention.

The present invention further provides electrostatic latent image developing toner at least comprising binder resin, a coloring agent, and the charge control agent of the present invention.

The present invention further provides an image forming method at least including a step of externally applying a voltage to a charging member thereby charging an electrostatic latent image bearing member, a step of forming an electrostatic latent image on the charged electrostatic latent image bearing member, a development step of developing the electrostatic latent image with electrostatic latent image developing toner thereby forming a toner image on the electrostatic latent image bearing member, a transfer step of transferring the toner image on the electrostatic latent image bearing member onto a recording material, and a fixation step of heat fixing the toner image on the recording material, the method being featured by using electrostatic latent image developing toner containing at least a binder resin, a coloring agent, and a charge control agent of the present invention.

The present invention further provides an image forming method at least comprising a step of externally applying a voltage to a charging member thereby charging an electrostatic latent image bearing member, a step of forming an electrostatic latent image on the charged electrostatic latent image bearing member, a development step of developing the electrostatic latent image with electrostatic latent image developing toner thereby forming a toner image on the electrostatic latent image bearing member, a first transfer step of transferring the toner image on the electrostatic latent image bearing member onto an intermediate transfer member, a second transfer step of transferring the toner image on the intermediate transfer member onto a recording material, and a fixation step of heat fixing the toner image on the recording material, the method being featured by using electrostatic latent image developing toner containing at least a binder resin, a coloring agent, and a charge control agent of the present invention.

The present invention further provides an image forming apparatus featured by forming an image with electrostatic latent image developing toner containing the charge control agent of the present invention.

The present invention further provides an image forming apparatus at least comprising means for externally applying a voltage to a charging member thereby charging an electrostatic latent image bearing member, means for forming an electrostatic latent image on the charged electrostatic latent image bearing member, development means for developing the electrostatic latent image with electrostatic latent image developing toner thereby forming a toner image on the electrostatic latent image bearing member, transfer means for transferring the toner image on the electrostatic latent image bearing member onto a recording material, and fixation means for heat fixing the toner image on the recording material, the apparatus being featured by using electrostatic latent image developing toner containing at least a binder resin, a coloring agent, and a charge control agent of the present invention. The present invention further provides an image forming apparatus at least comprising means for externally applying a voltage to a charging member thereby charging an electrostatic latent image bearing member, means for forming an electrostatic latent image on the charged electrostatic latent image bearing member, development means for developing the electrostatic latent image with electrostatic latent image developing toner thereby forming a toner image on the electrostatic latent image bearing member, first transfer means for transferring the toner image on the electrostatic latent image bearing member onto an intermediate transfer member, second transfer means for transferring the toner image on the intermediate transfer member onto a recording material, and fixation means for heat fixing the toner image on the recording material, the apparatus being featured by using electrostatic latent image developing toner containing at least a binder resin, a coloring agent, and a charge control agent of the present invention.

The PHA producing method of the present invention cultures microorganisms in a culture medium containing ω-(2-thienylsulfanyl) alkanoic acid as the raw material and processing PHA including 3-hydroxy-ω-(2-thienylsulfanyl) alkanoic acid, produced by the cultured microorganisms, with sodium hypochlorite to convert sulfanyl radical (—S—) thereof into sulfonyl radical (—$SO_2$—), thereby enabling production of novel biodegradable polyhydroxyalkanoate featured by containing, in the polymer molecule, a 3-hydroxy-ω-(2-thienylsulfinyl) alkanoic acid unit represented by the general formula (1), a 3-hydroxy-ω-(2-thienylsulfonyl) alkanoic acid unit represented by the general formula (2), and at least one of a ω-chloro-3-hydroxy-ω-(2-thienylsulfinyl) alkanoic acid unit represented by the general formula (3), a ω-chloro-3-hydroxy-ω-(2-thienylsulfonyl) alkanoic acid unit represented by the general formula (4), a ω, ω-dichloro-3-hydroxy-ω-(2-thienylsulfinyl) alkanoic acid unit represented by the general formula (5) and a ω,ω-dichloro-3-hydroxy-ω-(2-thienylsulfonyl) alkanoic acid unit represented by the general formula (6). In addition, PHA produced by the PHA producing method of the present invention has a specific structure including a thiophene ring and a sulfone structure (—$SO_2$—) or a sulfoxide structure (—SO—), and also has a chloro radical substitution on a methylene radical adjacent to the sulfur atom of such sulfone structure (—$SO_2$—) or sulfoxide structure (—SO—), whereby the electrons are localized within the molecule to enable application to fields different from those of the usual polyhydroxyalkanoate, such as optofunctional materials or device materials.

Also the present invention allows to provide a biodegradable charge control agent excellent in the charging characteristics and improved in the dispersibility thereof into the toner resin and in the spent performance.

Also by containing such charge control agent, there can be provided electrostatic latent image developing toner which is free from image fogging even at the output in the image forming apparatus, is excellent in transferrability, and is highly adapted to the electrophotographic process.

Also as the charge control agent of the present invention is colorless or only weakly colored, there can be selected arbitrary coloring agent according to the hue required for the color toner, and the original hue of dye or pigment is not at all hindered.

In addition, the electrostatic latent image developing toner of the present invention does not require use of heavy metals and is biodegradable, thereby providing an industrially important advantage of not affecting the environment.

The above and other objects, effects, features and advantages of the present invention will become more apparent from the following description of embodiments thereof taken in conjunction with the accompanying drawings.

DETAILED DESCRIPTION OF THE PREFERRED EMBODIMENTS

Figure 1:
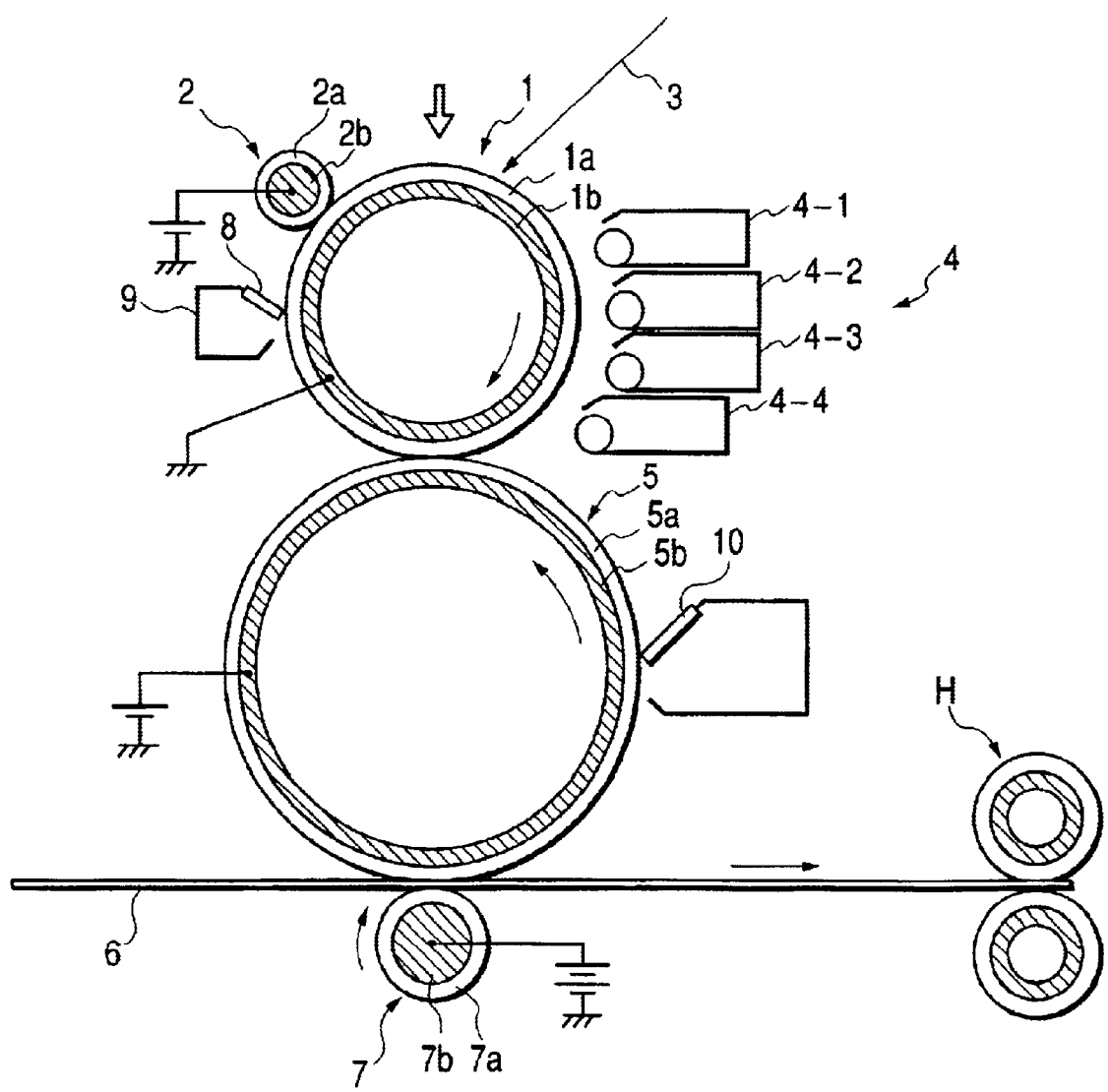
FIG. 1 is a schematic cross-sectional view of an image forming apparatus for executing the image forming method in the examples and comparative examples of the present invention.

The novel polyhydroxyalkanoate of the present invention is provided, as the constituent monomer units, with a unit having a thiophene ring and a sulfoxide structure (—SO—) in the form of a 2-thienylsulfinyl radical at the end of the side chain of a 3-hydroxy alkanoic acid unit, a unit having a thiophene ring and a sulfone structure (—$SO_2$—) in the form of a 2-thienylsulfonyl radical, and a chloro-substituted unit having chloro radical substitution on an ω-carbon atom adjacent to the sulfur atom of the aformentioned sulfone (—SO₂—) or sulfoxide (—SO—) structure. Because of such structure, it shows physicochemical properties significantly different from those of the conventionally known microorganism-produced polyhydroxyalkanoate. Such polyhydroxyalkanoate of the present invention can be produced, for example, by a step of culturing microorganisms having ability of producing polyhydroxyalkanoate in a culture medium containing ω-(2-thienylsulfanyl) alkanoic acid which is the starting carboxylic acid derivative represented by the general formula (27), and a step of processing, with sodium hypochlorite, the PHA containing 3-hydroxy-ω-(2-thienylsulfanyl) alkanoic acid unit and produced by the cultured microorganism cells. Consequently the PHA of the present invention, derived from the intermediate PHA produced by the aforementioned microorganisms, retain the property of biodegradable optical isomer, and, in combination with the novel physicochemical properties, enables exploitation of novel applications for PHA.

The present invention will be explained in the following in more details.

(Carboxylic Acid Derivative)

ω-(2-thienylsulfanyl) alkanoic acid to be employed in the present invention is a carboxylic acid derivative represented by a chemical formula (27). The ω-(2-thienylsulfanyl) alkanoic acid represented by the chemical formula (11) is a novel substance:

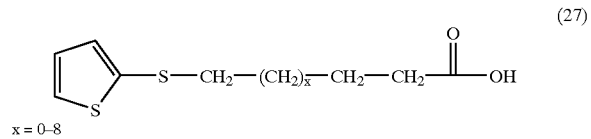

(27)

(wherein x is an integer of 0–8)

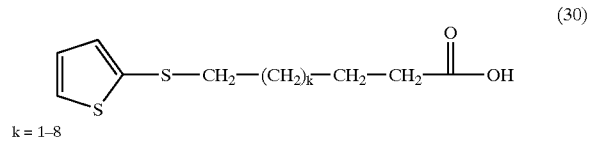

(30)

(wherein k is an integer of 1–8)

Also ω-(2-thienylsulfanyl) alkanoic acid in which k=ω (ω being an integer from 1 to 8) in the chemical formula (30) can be produced in the following methods:

1-1. a method of reacting thiophene-2-thiol and ω-bromoalkanoic acid to obtain ω-(2-thienylsulfanyl) alkanoic acid represented by the chemical formula (30);
1-2. a method of reacting thiophene-2-thiol and ω-bromoalkanoic acid to obtain ω-(2-thienylsulfanyl) alkanoic acid ester and then hydrolyzing the ester to obtain ω-(2-thienylsulfanyl) alkanoic acid represented by the chemical formula (30);
1-3. a method of reacting thiophene-2-thiol and ω-bromo-1-alkanol to obtain ω-(2-thienylsulfanyl)-1-alkanol and then executing oxidation to obtain ω-(2-thienylsulfanyl) alkanoic acid represented by the chemical formula (30);
1-4. a method of reacting thiophene-2-thiol and 1,ω-dibromoalkane to obtain 2-[(ω-bromoalkyl) sulfanyl] thiophene, then preparing a Grignard reagent with metallic magnesium and adding carbon dioxide gas to obtain ω-(2-thienylsulfanyl) alkanoic acid represented by the chemical formula (30); and
1-5. a method of reacting thiophene-2-thiol and a lactone to obtain ω-(2-thienylsulfanyl) alkanoic acid represented by the chemical formula (30).

These producing methods will be explained further in more details.

At first there will be shown methods for producing 5-(2-thienylsulfanyl) valeric acid represented by the chemical formula (28):

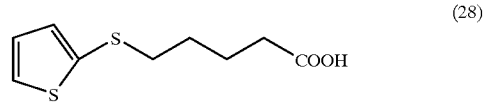

(28)

2-1. a method of reacting thiophene-2-thiol and 5-bromovaleric acid to obtain 5-(2-thienylsulfanyl) valeric acid represented by the chemical formula (28);
2-2. a method of reacting thiophene-2-thiol and 5-bromovaleric acid ester to obtain 5-(2-thienylsulfanyl) valeric acid ester and then hydrolyzing the ester to obtain 5-(2-thienylsulfanyl) valeric acid represented by the chemical formula (28);
2-3. a method of reacting thiophene-2-thiol and 5-bromo-1-pentanol to obtain 5-(2-thienylsulfanyl)-1-pentanol and then executing oxidation to obtain 5-(2-thienylsulfanyl) valeric acid represented by the chemical formula (28);
2-4. a method of reacting thiophene-2-thiol and 1,4-dibromobutane to obtain 2-[(4-bromobutyl) sulfanyl] thiophene, then preparing a Grignard reagent with metallic magnesium and adding carbon dioxide gas to obtain 5-(2-thienylsulfanyl) valeric acid represented by the chemical formula (28); and
2-5. a method of reacting thiophene-2-thiol and δ-valerolactone to obtain 5-(2-thienylsulfanyl) valeric acid represented by the chemical formula (28).

In the following there will be shown methods for producing 6-(2-thienylsulfanyl) hexanoic acid represented by the chemical formula (29):

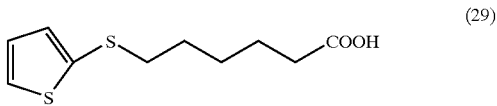

(29)

3-1. a method of reacting thiophene-2-thiol and 6-bromohexanoic acid to obtain 6-(2-thienylsulfanyl) hexanoic acid represented by the chemical formula (29);
3-2. a method of reacting thiophene-2-thiol and 6-bromohexanoic acid ester to obtain 6-(2-thienylsulfanyl) hexanoic acid ester and then hydrolyzing the ester to obtain 6-(2-thienylsulfanyl) hexanoic acid represented by the chemical formula (29);
3-3. a method of reacting thiophene-2-thiol and 6-bromo-1-hexanol to obtain 6-(2-thienylsulfanyl)-1-hexanol and then executing oxidation to obtain 6-(2-thienylsulfanyl) hexanoic acid represented by the chemical formula (29);
3-4. a method of reacting thiophene-2-thiol and 1,5-dibromopentane to obtain 2-[(5-bromopentyl) sulfanyl] thiophene, then preparing a Grignard reagent with metallic magnesium and adding carbon dioxide gas to obtain 6-(2-thienylsulfanyl) hexanoic acid represented by the chemical formula (29); and
3-5. a method of reacting thiophene-2-thiol and ε-caprolactone to obtain 6-(2-thienylsulfanyl) hexanoic acid represented by the chemical formula (29).

However, the production of the carboxylic acid derivatives represented by the chemical formula (30) is not limited to the above-mentioned producing methods.

In the PHA producing method of the present invention, the microorganisms to be employed for producing the precursor PHA constituting the intermediate material can be any microorganisms capable, in the culture in a culture medium containing the starting ω-(2-thienylsulfanyl) alkanoic acid represented by the general formula (27), of producing and accumulating PHA including 3-hydroxy alkanoic acid unit having a 2-thienylsulfanyl radical at the end of the corresponding side chain, such as those belonging to the *Pseudomonas* genus with PHA producing ability. Examples of preferred microorganisms of *Pseudomonas* genus include *Pseudomonas cihorii* YN2 (FERM BP-7375), *Pseudomonas cihorii* H45 (FERM-7374) and *Pseudomonas jessenii* P161 (FERM BP-7376). These three microorganisms are in advance domestically deposited under the name of the present applicant, then transferred from such original deposit to the deposit based on the Budapest treaty and deposited under the aforementioned deposition numbers in International Patent Organism Depositary of Institute of Advanced Industrial Science and Technology (former National Institute of Bioscience and Human Technology, Agency of Industrial Science and Technology) as the International Deposition Organization. Also they are described in the Japanese Patent Application No. 11-371863 as novel strains having PHA producing ability.

In the following there will be shown the bacteriological properties of the strains YN2, H45 and P161.

<Bacteriological Properties of Stain YN2>
(1) Morphological Properties

Shape and size of cells: rod, 0.8 μm×1.5 to 2.0 μm
Polymorphism of cells: negative
Mobility: mobile
Sporulation: negative
Gram staining: negative
Colony shape: circular; entire, smooth margin; low convex; smooth surface; glossy; translucent (2) Physiological Properties Catalase: positive
Oxydase: positive
O/F test: oxidative (non-fermentative)
Nitrate reduction: negative
Indole production: positive
Acid production from glucose: negative
Arginine dihydrolase: negative
Urease: negative
Eaculin hydrolysis: negative
Gelatin hydrolysis: negative
β-Galactosidase: negative
Fluorescent pigment production on King's B agar: positive
Growth under 4% NaCl: positive (weak growth)
Poly-β-hydroxybutyrate accumulation: negative (*)
(*) Colonies cultured on nutrient agar were stained with Sudan Black for determination.
Tween 80 hydrolysis: positive (3) Substrate Assimilation Glucose: positive
L-Arabinose: positive
D-Mannose: negative
D-Mannitol: negative
N-Acetyl-D-glucosamine: negative
Maltose: negative
Potassium gluconate: positive
n-Caprate: positive
Adipate: negative
dl-Malate: positive
Sodium citrate: positive
Phenyl acetate: positive <Bacteriological Properties of Stain H45>
(1) Morphological Properties Shape and size of cells: rod, 0.8 μm×1.0 to 1.2 μm
Polymorphism of cells: negative
Mobility: mobile
Sporulation: negative
Gram staining: negative
Colony shape: circular; entire, smooth margin; low convex; smooth surface; glossy; cream colored (2) Physiological Properties Catalase: positive
Oxydase: positive
O/F test: oxidative
Nitrate reduction: negative
Indole production: negative
Acid production from glucose: negative
Arginine dihydrolase: negative
Urease: negative
Eaculin hydrolysis: negative
Gelatin hydrolysis: negative
β-Galactosidase: negative
Fluorescent pigment production on King's B agar: positive
Growth under 4% NaCl: negative
Poly-β-hydroxybutyrate accumulation: negative (3) Substrate Assimilation Glucose: positive
L-Arabinose: negative
D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive <Bacteriological Properties of Stain P161>
(1) Morphological Properties Shape and size of cells: spheres Φ0.6 μm, rods, 0.6 μm×1.5 to 2.0 μm
Polymorphism of cells: elongated form
Mobility: mobile
Sporulation: negative
Gram staining: negative
Colony shape: circular; entire, smooth margin; low convex; smooth surface; glossy; pale yellow (2) Physiological Properties Catalase: positive
Oxydase: positive O/F test: oxidative
Nitrate reduction: positive
Indole production: negative
Acid production from glucose: negative
Arginine dihydrolase: positive
Urease: negative
Eaculin hydrolysis: negative
Gelatin hydrolysis: negative
β-Galactosidase: negative
Fluorescent pigment production on King's B agar: positive (3) Substrate Assimilation Glucose: positive
L-Arabinose: positive
D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive In addition to the microorganisms belonging to *Pseudomonas* genus, there can also be utilized the microorganisms belonging to *Aeromonas* sp., *Comamonas* sp., *Burkholderia* sp. etc. and capable of producing PHA including 3-hydroxy alkanoic acid unit represented by the aforementioned general formula (3) utilizing substituted alkanoic acid represented by the aformentioned general formula (15) as the raw material (substrate).

(Culturing Step)

In the step 1 of the PHA producing method of the present invention, the aforementioned microorganisms having the PHA producing ability are utilized to produce, from ω-(2-thienylsulfanyl) alkanoic acid constituting the raw material and represented by the aforementioned general formula (27), PHA including 3-hydroxy-ω-(2-thienylsulfanyl) alkanoic acid unit having 2-thienylsulfanyl radical at the end of the corresponding side chain.

For the ordinary culture of the microorganisms to be utilized in the step 1, for example for preparation or reserve strain or for proliferation for securing the number of bacteria required for PHA production or for securing the active state, there is suitably selected a culture medium containing components necessary for the proliferation of the microorganisms. For example, unless detrimental to the growth or life of the microorganisms, there can be employed any culture medium, such as usual natural culture medium (soup culture medium, enzyme extract etc.) or synthesized culture medium in which nutrition sources are added. The culture conditions such as temperature, aeration, agitation etc. are suitably selected according to the microorganisms to be used.

On the other hand, in case of causing the aforementioned PHA producing microorganisms to produce PHA including 3-hydroxy-ω-(2-thienylsulfanyl) alkanoic acid unit having 2-thienylsulfanyl radical at the end of side chain as the intermediate raw material, there can be employed for example an inorganic culture medium containing at least a carbon source for proliferation of the microorganisms in addition to ω-(2-thienylsulfanyl) alkanoic acid compound represented by the aforementioned general formula (27).

The initial content of the raw material compound represented by the general formula (27) is preferably selected within a range of 0.01 to 1%(w/v), more preferably 0.02 to 0.2%(w/v). ω-(2-thienylsulfanyl) alkanoic acid represented by the general formula (27) does not necessarily have satisfactory solubility in water because of its structure having a thiophene ring at the end, but may remain partially suspended in a portion exceeding the solubility at the initial stage of culture, since the aforementioned microorganisms have the property capable of utilizing such compound as the substrate and gradually intake such compound into the cells whereby the initially suspended portion is instead dissolved into the culture medium.

The raw material compound represented by the general formula (27) may also be added to the culture medium in a state dissolved or finely dispersed in solvent such as 1-hexadecene or n-hexadecane in order to improve dispersibility. In such case, the concentration of the solvent such as 1-hexadecene or n-hexadecane should not exceed 3% (w/v).

A proliferation carbon source, to be utilized for proliferation of the microorganisms, is separately added to the culture medium. For such proliferation carbon source, there can be used nutrition source such as yeast extract, polypeptone or meat extract. Also, in consideration of the effectiveness as the carbon source according to the strain to be used, there can be suitably selected saccharides, organic acids generated as intermediate products in the TCA circuit or generated a biochemical reaction of one or two steps from the TCA circuit or salts thereof, amino acids or salts thereof, or straight-chain alkanoic acids with 4 to 12 carbon atoms or salts thereof.

Among these carbon sources, as the saccharide, there can be advantageously utilized one or more compounds selected from aldoses such as glyceraldehyde, erythrose, arabinose, xylose, glucose, galactose, mannose or fructose, alditols such as glycerol, erythritol or xylitol, aldonic acids such as gluconic acid, uronic acids such as glucronic acid or galacturonic acid, and disaccharides such as maltose, sucrose or lactose.

Also as organic acid or salt thereof, there can be advantageously utilized one or more compounds selected from a group consisting of piruvic acid, malic acid, lactic acid, citric acid, succinic acid and salts thereof. Also as amino acid or salts thereof, there can be advantageously utilized one or more compounds selected from a group consisting of glutamic acid, aspartic acid and salts thereof.

Among these various carbon sources, there are preferred polypeptone and saccharides, and, among saccharides, there is more preferred to use at least one selected from a group consisting of glucose, fructose and mannose. The content of such carbon source substrate in the culture medium is preferably selected within a range of 0.1 to 5% (w/v), more preferably 0.2 to 2% (w/v).

In the culture method in the step 1 for causing the microorganisms to produce and accumulate PHA, the productivity may further increase, after sufficient proliferation, by transferring the bacteria to a culture medium in which the nitrogen source such as ammonium chloride is limited and executing further culture in a state including the compound constituting the substrate of the desired unit. For example there can be employed a multi-step method by connecting plural steps of different culture conditions.

More specifically, it is more preferable to employ a two-step culture method of executing, as (step 1-1), a step of continuing the culture of the microorganisms in a culture medium containing the compound represented by the general formula (27) and polypeptone constituting the carbon source from the latter stage of logarithmic proliferation to the stationary state, then recovering the bacteria for example by centrifuging, and executing, as (step 1-2), further culture of the microorganisms cultured in the step 1-1 in a culture medium containing the compound represented by the general formula (27) and the organic acid or salt thereof constituting the carbon source but not containing nitrogen source, or a two-step culture method of executing, as (step 1-3), a step of continuing the culture of the microorganisms in a culture medium containing the compound represented by the general formula (27) and saccharides constituting the carbon source from the latter stage of logarithmic proliferation to the stationary state, then recovering the bacteria for example by centrifuging, and executing, as (step 1-4), further culture of the microorganisms cultured in the step 1-3 in a culture medium containing the compound represented by the general formula (27) and saccharides constituting the carbon source but not containing nitrogen source. In such two-step culture method, it is possible to further increase the PHA amount accumulated in the cells, by proliferating the bacteria in advance in the former step while causing the bacteria to produce, from ω-(2-thienylsulfanyl) alkanoic acid represented by the general formula (27) as a raw material, the PHA including 3-hydroxy alkanoic acid unit having 2-thienylsulfanyl radical at the end of the side chain as the desired intermediate material, and, in the later step, by causing the already cultured bacteria to principally execute PHA production in the culture medium not containing the nitrogen source.

The culture temperature in the step 1 can be any temperature at which the aforementioned strains can satisfactorily proliferate, and can be within a range of 15 to 40° C., preferably 20 to 35° C., more preferably 20 to 30° C.

The culture can be executed in any culture method such as liquid culture or solid culture, in which the employed microorganisms can proliferate and can produce, from the starting compound represented by the general formula (27) and contained in the culture medium, the PHA including 3-hydroxy alkanoic acid unit having 2-thienylsulfanyl radical at the end of the side chain. Also there may be employed any of batch culture, fed batch culture, semi-continuous culture or continuous culture as long as the raw material, carbon source and oxygen can be appropriately supplied. For example for liquid batch culture, there can be employed oxygen supply method by vibration in a shaking flask or by agitated aeration in a jar fermenter.

Also in the aforementioned culture methods, there may be employed any inorganic culture medium containing components necessary for the proliferation of the microorganisms, such as phosphor source (for example phosphoric salt) and nitrogen source (for example ammonium salt or nitrate salt), such as MSB culture medium or M9 culture medium.

In the following there will be shown the composition of the inorganic salt M9 culture medium employed in the examples to be explained later.

[M9 Culture Medium]

| | |
|---|---|
| $Na_2HPO_4$ | 6.2 g |
| $KH_2PO_4$ | 3.0 g |
| NaCl | 0.5 g |
| $NH_4Cl$ | 1.0 g |
| (in 1 liter of culture medium; pH 7.0) | |

For satisfactory proliferation and resulting PHA production, the above-mentioned inorganic culture medium has to be replenished with the essential minor elements by adding the following minor component solution by about 0.3% (w/v).

[Minor Component Solution]

| | |
|---|---|
| nitrilotriacetic acid | 1.5 g; |
| $MgSO_4$ | 3.0 g; |
| $MnSO_4$ | 0.5 g; |
| NaCl | 1.0 g; |
| $FeSO_4$ | 0.1 g; |
| $CaCl_2$ | 0.1 g; |
| $CoCl_2$ | 0.1 g; |
| $ZnSO_4$ | 0.1 g; |
| $CuSO_4$ | 0.1 g; |
| $AlK(SO_4)_2$ | 0.1 g; |
| $H_3BO_3$ | 0.1 g; |
| $Na_2MoO_4$ | 0.1 g; |
| $NiCl_2$ | 0.1 g; |
| (in 1 liter of solution, pH 7.0). | |

(Step of Processing with Sodium Hypochlorite)

For example as already disclosed in the Japanese Patent Application No. 2001-057085 of the present applicant, the microorganisms employed in the present invention in the aforementioned culture methods produce the PHA including a unit having thiophene ring and sulfanyl radical (—S—) as 2-thienylsulfanyl radical to be substituted at the end of the side chain. The PHA of the present invention can be produced by selectively oxidizing the sulfanyl radical (—S—) among the sulfur portions in thus produced PHA. As a specific example, such desired PHA can be produced by applying a process with sodium hypochloride as the oxidant on the intermediate PHA including 3-hydroxy-ω-(2-thienylsulfanyl) alkanoic acid unit having 2-thienylsulfanyl radical.

Among the processing methods utilizing sodium hypochlorite in such step 2, the simplest method consists of suspending and agitating the microorganism cells, in which the PHA including 3-hydroxy-ω-(2-thienylsulfanyl) alkanoic acid unit constituting the precursor (intermediate raw material) of PHA of the present invention are produced and accumulated, in aqueous solution of sodium hypochlorite thereby simultaneously executing removal of insoluble components resulting from the cells and process on PHA. In such direct processing with sodium hypochlorite on the cells, the PHA after processing with sodium hypochlorite is recovered as an insoluble component in the final stage. In such method, in case the concentration of aqueous solution of sodium hypochlorite is relatively high or in case the reaction temperature is relatively high, the PHA of the present invention can be recovered in an almost pure form as an insoluble component after the processing, but, if the reaction condition is too harsh, there may result a reduction in the molecular weight resulting from local cleavage of the ester bond in the main chain. On the other hand, in case the concentration of the aqueous solution of sodium hypochlorite is low, the simultaneously proceeding oxidation and dissolution of the components deriving from the bacteria cells may become insufficient and a part of the components deriving from the bacteria cells such as cell membrane may remain in the insoluble component.

In order to prevent such retention of the components derived from the bacteria cells, there may be employed a method of executing in advance a step of pulverizing the cells of the cultured microorganisms and recovering in crude state the microorganism-produced PHA including 3-hydroxy-ω-(2-thienylsulfanyl) alkanoic acid and constituting the precursor of the PHA of the present invention, and then processing thus recovered precursor PHA (intermediate material) with sodium hypochlorite. Such method including the step of pulverizing the cells and separating and recovering the precursor PHA (intermediate material) allows to recover PHA in a highly pure state even executing the process with sodium hypochlorite under a relatively mild condition.

Also for preventing such retention of the components derived from the bactereia cells, there is another method of executing a step of extracting and separating PHA only with solvent capable of dissolving PHA such as chloroform or acetone from the microorganism cells separated from the culture medium after the step 1 and accumulating the produced PHA therein, and then processing thus extracted and separated precursor PHA (intermediate material) with sodium hypochlorite. In such method including the step of separating and recovering the precursor PHA (intermediate material) by solvent extraction, the extracted and recovered PHA may form blocks in the aqueous medium, thereby resulting in difficulty in operation of significantly lowering the efficiency of recovery with sodium hypochlorite. Therefore, the first-mentioned two methods are also in operation, because the precursor PHA originally present in small particles in the microorganism cells can be processed with sodium hypochlorite in such suspended state.

Sodium hypochlorite employed in the PHA producing method of the present invention can assume any form as long as it can contribute to the object of the present invention, namely executing selective oxidation of sulfanyl radical (—S—) present as 2-thienylsulfanyl radical and also chlorination of the end methylene radical of the side carbon chain on which such 2-thienylsulfanyl radical is substituted. In general, sodium hypochlorite is utilized in the form of aqueous solution thereof.

The processing condition with sodium hypochlorite in the step 2 of the PHA producing method of the present invention is suitably selected according to the state of the processed precursor PHA (presence or absence of solid component, block form or fine particulate form etc.), but can be generally be selected within the following ranges.

The concentration of sodium hypochlorite, as effective chlorine concentration in the processing liquid, is desirably within a range of 0.5 to 12.0%, preferably 1.5 to 5.0%. Also in case of processing in the state including cells themselves, it is desirable to execute processing by selecting the liquid amount within a range of 50 to 300 ml/g of dried weight of the dried microorganism cells. In the processing, the process temperature is desirably within a range of 0 to 20° C., preferably 0 to 10° C., under the control of the reaction activity, since a process temperature higher than the room temperature (about 20° C.) may result in the aforementioned decrease of the molecular weight of PHA. The reaction time depends on the concentration of sodium hypochlorite and process temperature, but is usually selected within a range of 1 to 5 hours, preferably about 2 hours in case of the aforementioned preferred concentration and temperature range, thereby avoiding accumulation of unnecessary subsidiary reactions.

Under the aforementioned process condition with sodium hypochlorite, the PHA including 3-hydroxy-ω-(2-thienylsulfanyl) alkanoic acid unit and accumulated in the bacteria cultured in the step 1 is converted into PHA including, in 3-hydroxy-ω-(2-thienylsulfanyl) alkanoic acid unit thereof, a 3-hydroxy-ω-(2-thienylsulfinyl) alkanoic acid unit represented by the following general formula (1):

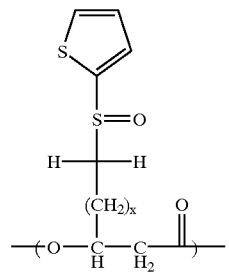

X = 0–8

(wherein x stands for an integer selected within a range of 0–8 indicated in the chemical formula, and such unit may be present at least one in the polymer);

a 3-hydroxy-ω-(2-thienylsulfonyl) alkanoic acid unit represented by the following general formula (2):

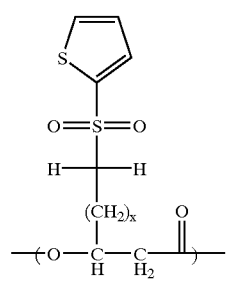

X = 0–8

(wherein x stands for an integer selected within a range of 0–8 indicated in the chemical formula, and such unit may be present at least one in the polymer); and at least one of the chloro-substituted units represented by the following general formulas (3) to (6), namely:

a ω-chloro-3-hydroxy-ω-(2-thienylsulfinyl) alkanoic acid unit represented by the following general formula (3):

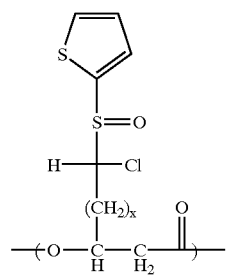

X = 0–8

(wherein x stands for an integer selected within a range of 0–8 indicated in the chemical formula, and such unit may be present at least one in the polymer);

a ω-chloro-3-hydroxy-ω-(2-thienylsulfonyl) alkanoic acid unit represented by the following general formula (4):

(4)

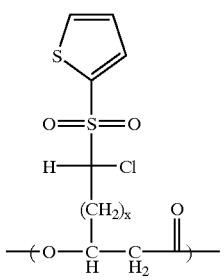

X = 0–8

(wherein x stands for an integer selected within a range of 0–8 indicated in the chemical formula, and such unit may be present at least one in the polymer);

a ω,ω-dichloro-3-hydroxy-ω-(2-thienylsulfinyl) alkanoic acid unit represented by the following general formula (5):

(5)

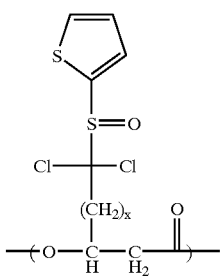

X = 0–8

(wherein x stands for an integer selected within a range of 0–8 indicated in the chemical formula, and such unit may be present at least one in the polymer); and a ω,ω-dichloro-3-hydroxy-ω-(2-thienylsulfonyl) alkanoic acid unit represented by the following general formula (6):

(6)

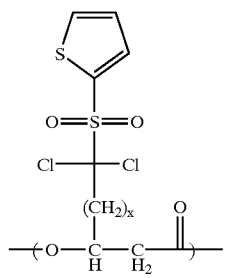

X = 0–8

(wherein x stands for an integer selected within a range of 0–8 indicated in the chemical formula, and such unit may be present at least one in the polymer).

For recovering PHA in the process liquid after processing with sodium hypochlorite in the step 2, there can be utilized any method capable of effectively separating and purifying PHA from the soluble components. For example there can be utilized centrifuging. Also in case chlorine derived from sodium hypochlorite may remain in the recovered PHA, it is preferable to add a step of rinsing the recovered PHA for example with purified water. It is more preferable to add a step of rinsing the recovered PHA with a chemical capable of eliminating remaining chlorine within an extent the physico-chemical properties of the PHA are not changed.

The novel polyhydroxyalkanoate of the present invention includes, as the constituent monomer units, the units represented by the aforementioned general formulas (1) and (2), and at least one of the four chloro-substituted units represented by the general formulas (3) to (6), and is provided with a thiophene ring and a sulfone structure ($-SO_2-$) or a sulfoxide structure ($-SO-$), and is further provided with a partial structure having chloro radical substitution on a methylene radical adjacent to such sulfone structure ($-SO_2-$) or sulfoxide structure ($-SO-$). Such specific structure induces localization of the electrons in the molecule and enables application in the field different from that of the usual polyhydroxyalkanoate, such as optofunctional materials or device materials.

Also the present invention has been attained by a finding that the PHA produced in the present invention has extremely excellent characteristics as a charge control agent and that electrostatic latent image developing toner containing such charge control agent provides significant effect when used in an image forming apparatus provided with a certain developing system.

More specifically, the present invention provides a charge control agent containing polyhydroxyalkanoate including, in the polymer molecule, a unit represented by the following general formula (1):

(1)

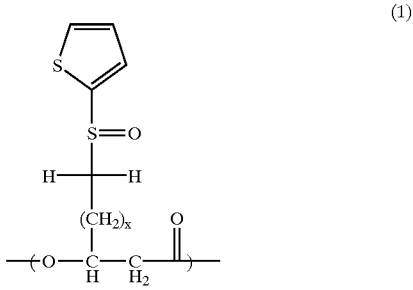

X = 0–8

(wherein x stands for an integer selected within a range of 0–8 indicated in the chemical formula, and such unit may be present at least one in the polymer);

a unit represented by the following general formula (2):

(2)

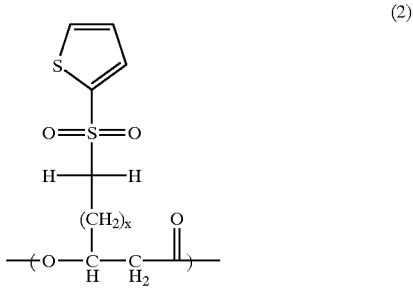

X = 0–8

(wherein x stands for an integer selected within a range of 0–8 indicated in the chemical formula, and such unit may be present at least one in the polymer); and at least one of the units represented by the following general formulas (3) to (6), namely:

a unit represented by the following general formula (3):

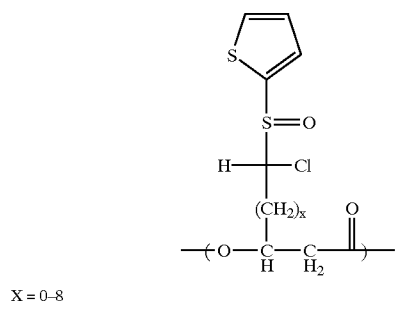

(3)

X = 0–8

(wherein x stands for an integer selected within a range of 0–8 indicated in the chemical formula, and such unit may be present at least one in the polymer);

a unit represented by the following general formula (4):

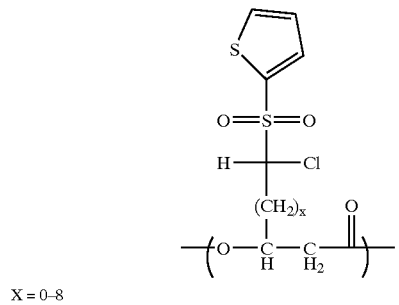

(4)

X = 0–8

(wherein x stands for an integer selected within a range of 0–8 indicated in the chemical formula, and such unit may be present at least one in the polymer);

a unit represented by the following general formula (5):

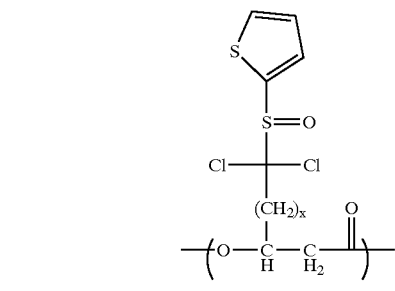

(5)

X = 0–8

(wherein x stands for an integer selected within a range of 0–8 indicated in the chemical formula, and such unit may be present at least one in the polymer); and a unit represented by the following general formula (6):

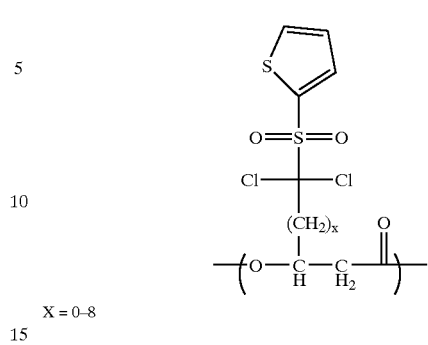

(6)

X = 0–8

(wherein x stands for an integer selected within a range of 0–8 indicated in the chemical formula, and such unit may be present at least one in the polymer), and a charge control agent in which such PHA may further include at least one of:

a unit represented by the following general formula (7):

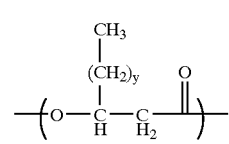

(7)

y = 0–8

(wherein y stands for an integer selected within a range of 0–8 indicated in the chemical formula, and such unit may be present at least one in the polymer); and a unit represented by the following general formula (8):

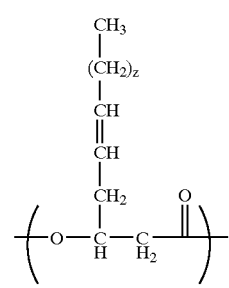

(8)

z = 3, 5

(wherein y and z can assume arbitrary integral values at least equal to one, within the ranges shown in the chemical formulas, independently from the units represented by (1), (2), (3), (4), (5) and (6)), and electrostatic latent image developing toner containing such charge control agent. The present invention also provides an image forming method including a charging step of externally applying a voltage to a charging member thereby uniformly charging an electrostatic latent image bearing member, a development step of forming a toner image on the electrostatic latent image bearing member, a transfer step of transferring the toner image on the electrostatic latent image bearing member onto a recording material either through or without an intermediate transfer member, and a heat fixation step of heat fixing the toner image on the recording material, the method being featured by using the aforementioned electrostatic latent image developing toner, and an image forming apparatus featured by forming an image on the recording material utilizing the aforementioned electrostatic latent image developing toner.

The compound disclosed by the present invention has a basic structure as biodegradable resin, and is expected to provide an effect not detrimentally affecting the environment. The compound disclosed by the present invention can be utilized in the production of various products for example by fusion as in the conventional plastics but, different from the synthesized polymers derived from petroleum, has specific property that it can be decomposed biologically. Therefore, the compound of the present invention, when discarded, is biodegraded and is fetched in the natural material chain and does not remain in the natural environment and does not cause contamination in contrast to the various synthesized polymer compounds conventionally utilized. Also it does not require heavy metals such as chromium, cobalt, nickel, copper, zinc and iron, and gives less burden to the environment in comparison with the conventional charge control agent. Also being degradable and not requiring combustion process, it is effective in preventing air pollution and warming of the earth, and can be utilized as plastics enabling environmental security.

In the following there will be given a specific explanation on the compound of the present invention, suitable as charge control agent to be employed in the electrostatic latent image developing toner of the present invention.

The compound to be used in the present invention is polyester resin composed of 3-hydroxyalkanoate as the monomer unit, includes a unit having a thienyl ring and a sulfonyl structure in the side chain, and also includes another unit which has a thienyl ring and a sulfinyl structure or a sulfonyl structure and in which methylene radical in α-position thereof is substituted with chlorine. Also the compound of the present invention may include, in addition to the aforementioned units, straight-chain 3-hydroxyalkanoate and 3-hydroxyalkanoate containing an unsaturated bond in the side chain simultaneously or independently.

In case such compound is produced by a method of production by microorganisms, the compound of the present invention becomes isotactic polymer consisting of R-isomer only, but such isotactic polymer is not particularly necessary and atactic polymer can also be utilized as long as the objects of the present invention can be attained in the physical properties and the functions. The compound of the present invention can also be obtained for example by chemical synthesis utilizing ring-opening polymerization of lactones.

Among the methods of the present invention, the production by a method including a step of causing the microorganisms to produce the compound of the present invention has been explained in the foregoing.

What is important in the present invention is that polyhydroxyalkanoate contained in the charge control agent of the present invention includes a unit having a thienyl ring and a sulfinyl or sulfonyl structure on the side chain, and another unit having a thienyl ring and a sulfinyl or sulfonyl structure and also having chloro-substitution in a methylene radical in the α-position thereof. These structures induce electron localization in the molecule, whereby the charge control agent of the present invention shows excellent negative charging property. Different from the conventional negatively chargeable polymer charge control agent, the charge control agent of the present invention including the units of the aforementioned structures does not contain ionic functional radicals and shows excellent weather resistance including moisture resistance.

Also it is possible to control the rise of charging by changing the ratio of the units of the aforementioned structures. It is further possible to reduce environmental dependence by controlling such unit ratio.

Polyhydroxyalkanoate contained in the charge control agent of the present invention often includes the units having thienyl ring on the side chain and also having sulfinyl or sulfonyl structure, namely the units represented by the aforementioned chemical formulas (1) and (2), because of the production method, but the presence of such units are not essential in consideration of the contribution to the charging ability of the charge control agent of the present invention, and the presence of a unit having thienyl ring and sulfinyl or sulfonyl structure and also having chloro-substitution on the methylene radical in α-position, namely at least one of the units represented by the aforementioned chemical formulas (3), (4), (5) and (6), is considered to significantly contribute to the charging performance of the charge control agent of the present invention.

The units of such structures may be present at least 1 mol % in the polymer, and the proportion thereof may be selected in consideration of the ratio with other units and of the charging ability, but is preferably present at least 5 mol % in order to achieve sufficient charging ability. The upper limit amount of the unit can be determined in consideration of the kind of the selected binder resin and other units, and in an extent not hindering the mutual solubility with the binder resin.

The compound disclosed in the present invention has satisfactory mutual solubility with binder resin, particularly with polyester binder resin. The toner containing the compound disclosed in the present invention, having a high specific charge amount and satisfactory stability in time, can stably provide a sharp image in the electrostatic image formation even after prolonged storage, and, being colorless and negatively chargeable, can be formed as negatively chargeable black or color toner.

Also, the mutual solubility can be adjusted within a wide range by suitably selecting type/composition of the monomer units constituting the compound disclosed in the present invention.

By selecting the resin composition in such a manner that the charge control agent assumes a microscopic phase-separation structure in the toner binder, the toner can stably hold the charge because electric continuity is not caused in the toner. Also the compound of the present invention, not containing heavy metals, is extremely safe to the environment. Also the toner can be produced stably by suspension polymerization or emulsion polymerization, because of absence of inhibition of polymerization by a heavy metal, as encountered in the metal-containing charge control agent.

(Addition of PHA to Toner)

In the present invention, the aforementioned compound may be added to the toner by internal addition or by external addition. In case of internal addition, the addition amount in the mass ratio of the charge control agent to the toner binder is usually within a range of 0.1 to 50 mass %, preferably 0.3 to 30 mass %, more preferably 0.5 to 20 mass %. An amount less than 0.1 mass % is undesirable because of insufficient improvement in the charging ability of toner. Also an amount exceeding 50 mass % is undesirable because of economical standpoint. Also in case of external addition, the mass ratio of the charge control agent to the toner binder is preferably within a range of 0.01 to 5 mass %, and the charge control agent is preferably fixed to the toner surface in mechanochemical manner. Further, the compound of the present invention can be used in combination with the known charge control agent.

The compound of the present invention normally has a number average molecular weight of 1,000 to 500,000, preferably 1,000 to 100,000. At a molecular weight less than 1,000, it completely dissolves in the toner binder and does not easily form discontinuous phase, thereby resulting in insufficient charge amount and detrimentally affecting the flowability of toner. Also at a molecular weight exceeding 500,000, the dispersion in the toner becomes difficult.

The molecular weight of the compound of the present invention was measured by GPC (gel permeation chromatography). More specifically, the first compound of the present invention was dissolved in dimethylformamide (DMF) containing LiBr in 0.1 mass %, and plural samples were measured in similar moving phase and the molecular weight distribution was determined from a calibration line of standard polystyrene resin.

In the present invention, it is preferable to the aforementioned compound in which the ratio (Mw/Mn) of the weight average molecular weight Mw and the number average molecular weight Mn is within a range of 1 to 10.

In the present invention, it is preferred that the aforementioned compound of the present invention has a melting point within a range of 20 to 150° C., particularly 40 to 150° C., or does not have a melting point but has a glass transition point within a range of 20 to 150° C., particularly 40 to 150° C. If the melting point is lower than 20° C. or the melting point is absent but the glass transition point is lower than 20° C., the flowability and storability of the toner tend to be affected detrimentally. Also if the melting point is higher than 150° C. or the melting point is absent but the glass transition point is higher than 150° C., it becomes difficult to blend the charge control agent in the toner and the charge amount distribution tends to become broad.

The melting point Tm and the glass transition point Tg can be measured, for example, by a highly precise scanning differential thermal analyzer of internal input compensation type such as Perkin Elmer DSC-7.

In the toner binder and the electrostatic latent image developing toner of the present invention, the mass ratio of the charge control agent to the toner binder is usually within a range of 0.1 to 50 mass %, preferably 0.3 to 30 mass %, more preferably 0.5 to 20 mass %. The electrostatic latent image developing toner of the present invention is composed, based on the toner mass, of 0.1 to 50 mass % of the aforementioned charge control agent, 20 to 95 mass % of toner binder and 0 to 15 mass % of coloring agent, and, if necessary, may contain magnetic powder (powder of ferromagnetic metal such as iron, cobalt or nickel or a compound such as magnetite, hematite or ferrite) also as a coloring agent in an amount not exceeding 60 mass %. There may also be contained various additives (lubricant (such as polytetra-fluoroethylene, low molecular weight polyolefin, fatty acid or metal salt or amide thereof) and another charge control agent (such as nigrosin derivative, metal naphthenate, alkoxylated amine, or quaternary ammonium salt). Also there may be used hydrophobic colloidal silica powder or the like for improving flowability of toner. The amount of these additives does not usually exceed 10 mass % based on the toner mass.

In the toner of the present invention, it is preferable that at least a part of the toner binder constitutes continuous phase while at least a part of the charge control agent forms a discontinuous domain. In comparison with a case where the charge control agent is completely dissolved in the toner binder without forming discontinuous domain, the added charge control agent tends to be more exposed to the toner surface, thereby exhibiting effect with a smaller addition amount. The dispersion particle size of such domain is preferably within a range of 0.01 to 4 μm, more preferably 0.05 to 2 μm. A particle size exceeding 4 μm results in insufficient dispersibility and wider charge amount distribution, thus deteriorating the transparency of the toner. On the other hand, a case of the dispersion particle size less than 0.01 μm is similar to the situation where the charge control agent does not form discontinuous domain but is completely dissolved in the toner binder and requires the addition of the charge control agent in a large amount. The state that at least a part of the charge control agent forms discontinuous domain, and the dispersion particle size thereof can be confirmed by observing slices of the toner under a transmission electron microscope or the like. In order to clearly observe the interface, it is effective to execute the electron microscopic observation after dyeing the toner slices with ruthenium tetroxide or osmium tetroxide.

Also in order to reduce the particle size of the discontinuous domain formed by the compound of the present invention, it is possible to add polymer having mutual solubility with the compound of the present invention and mutual solubility also with the toner binder, as mutual dissolver. Examples thereof include polymer in which a polymer chain containing, by at least 50 mol %, a monomer of a structure substantially same as that of the monomer constituting the compound of the present invention, and a polymer chain containing, by at least 50 mol %, a monomer of a structure substantially same as that of the monomer constituting the toner binder are combined in graft or block manner. The amount of the mutual dissolver with respect to the compound of the present invention is usually not exceeding 30 mass %, preferably within a range of 1 to 10 mass %.

<Other Constituents>

In the following there will be explained other constituents constituting the electrostatic latent image developing toner of the present invention.

(Binder Resin)

At first, the binder resin is not particularly limited, and there can be used any binder resin usually employed in the toner preparation. The charge control agent of the present invention can be mixed with the binder resin prior to the preparation of the toner, and can be used as a toner binder composition of the present invention having the charge control ability. Examples of the binder resin include styrene polymer, polyester polymer, epoxy polymer, polyolefin polymer and polyurethane polymer, which can be employed singly or as a mixture.

Examples of the styrene polymer include copolymer of styrene and (meth)acrylate ester, copolymer thereof with another monomer capable of copolymerizing therewith, copolymer of styrene and dienic monomer (butadiene, isoprene etc.) and copolymer thereof with another monomer capable of copolymerizing therewith. Examples of polyester polymer include condensation-polymer of an aromatic dicarboxylic acid and addition product of aromatic diol with alkylene oxide. Examples of epoxy polymer include reaction product of aromatic diol and epichlorhydrin and denatured products thereof. Examples of polyolefin polymer include polyethylene, polypropylene and a copolymerized chain with another monomer capable of copolymerizing therewith. Examples of polyurethane polymer include polymerization-addition product of aromatic diisocyanate and alkylene oxide addition product of aromatic diol.

Specific examples of the binder resin employed in the present invention include polymers of following polymerizable monomers, mixtures thereof, and copolymerization products obtained by using at least two of the following polymerizable monomers. Specific examples of such compounds include styrene copolymers such as styrene-acrylic acid copolymer or styrene-methacrylic acid copolymer, polyester polymers, epoxy polymers, polyolefin polymers and polyurethane polymers.

Specific examples of the polymerizable monomer include styrene and derivatives thereof such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene or p-n-dodecylstyrene; ethylenic unsaturated monoolefins such as ethylene, propylene, butylene or isobutylene; unsaturated polyenes such as butadiene; halogenated vinyls such as vinyl chloride, vinylidene chloride, vinyl bromide or vinyl fluoride; vinyl esters such as vinyl acetate, vinyl propionate or vinyl benzoate; aliphatic α-methylene monocarboxylic acid ester such as methyl methacrylate, ethyl methacrylate, propyl methacrylate, n-butyl methacrylate, isobuty methacrylate, n-octyl methacrylate, dodecyl methacrylate, 2-ethylhexyl methacrylate, stearyl methacrylate, phenyl methacrylate, dimethylaminoethyl methacrylate or diethylaminoethyl methacrylate, acrylate esters such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate or phenyl acrylate; vinylethers such as vinylmethyl ether, vinylethyl ether or vinylisobutyl ether; vinylketones such as vinylmethyl ketone, vinylhexyl ketone or methylisopropenyl ketone; N-vinyl compounds such as N-vinylpyrrol, N-vinylcarbazole, N-vinylindole or N-vinylpyrrolidone; vinylnaphthalenes; acrylic or methacrylic acid derivatives such as acrylonitrile, methacrylonitrile, acrylamide; esters of the aforementioned α,β-unsaturated acids or dibasic acids; dicarboxylic acids such as maleic acid, methyl maleate, butyl maleate, dimethyl maleate, phthalic acid, succinic acid or terephthalic acid; polyols such as ethylene glycol, diethylene glycol, triethylene glycol, 1,2-propylene glycol, 1,3-propylene glycol, 1,4-butanediol, 1.6-hexanediol, bisphenol-A, hydrogenated bisphenol-A or polyoxyethylenated bisphenol-A; isocyanates such as p-phenylene diisocyanate, p-xylilene diisocyanate or 1,4-tetramethylene diisocyanate; amines such as ethylamine, butylamine, ethylenediamine, 1,4-diaminobenzene, 1,4-diaminobutane or monoethanolamine; and epoxy compounds such as diglycidyl ether, ethyleneglycol diglycidyl ether, bisphenol-A glycidyl ether or hydroquinone diglycidyl ether.

(Crosslinking Agent)

In the formation of the binder resin to be used in the present invention, there may be employed the following crosslinking agent if necessary. Examples of the crosslinking agent with two functional radicals include divinylbenzene, bis(4-acryloxy-polyethoxyphenyl) propane, ethyleneglycol diacrylate, 1,3-butyleneglycol diacrylate, 1,4-butanediol diacrylate, 1,5-pentanediol diacrylate, 1,6-hexanediol diacrylate, neopentylglycol diacrylate, diethyleneglycol diacrylate, triethyleneglycol diacrylate, tetraethyleneglycol diacrylate, diacrylates of polyethyleneglycol #200, #400 and #600, dipropyleneglycol diacrylate, polypropyleneglycol diacrylate, polyester type diacrylates (MANDA, NIPPON KAYAKU), and methacrylates corresponding to the foregoing acrylates.

Examples of the crosslinking agent with more than two functional radicals include pentaerythritol triacrylate, trimethyrolethane triacrylate, trimethyrolpropane triacrylate, tetramethyromethane triacrylate, oligoester acrylate and methacrylate, 2,2-bis(4-methacryloxy-polyethoxyphenyl) propane, diallyl phthalate, triallyl cyanurate, triallyl isocyanurate, triallyl trimellitate, and diaryl chlorendate.

(Polymerization Initiator)

In the formation of the binder resin to be used in the present invention, there may be employed the following polymerization initiator if necessary. Examples of the polymerization initiator include t-butylperoxy-2-ethyl hexanoate, cumin perpivarate, t-butyl peroxylaurate, benzoyl peroxide, lauroyl peroxide, octanoyl peroxide, di-t-butyl peroxide, t-butylcumyl peroxide, dicumyl peroxide, 2,2'-azobisisobutylonitrile, 2,2'-azobis(2-methylbutylonitrile), 2,2'-azobis(2,4-dimethylvaleronitrile), 2,2'-azobis(4-methoxy-2,4-dimethylvaleronitrile), 1,1-bis(t-butylperoxy)-3,3,5-trimethylcyclohexane, 1,1-bis(t-butylperoxy) cyclohexane, 1,4-bis(t-butylperoxycarbonyl) cyclohexane, 2,2-bis(t-butylperoxy) octane, n-butyl-4,4-bis(t-butylperoxy) varylate, 2,2-bis(t-butylperoxy) butane, 1,3-bis(t-butylperoxy-isopropyl) benzene, 2,5-dimethyl-2,5-di(t-butylperoxy) hexane, 2,5-dimethyl-2,5-di(benzoylperoxy) hexane, di-t-butyldiperoxy isophthalate, 2,2-bis(4,4-di-t-butylperoxycyclohexl) propane, di-t-butylperoxy-α-methyl succinate, di-t-butylperoxydimethyl glutanate, di-t-butylperoxy hexahydroterephthalate, di-t-butylperoxy azerate, 2,5-dimethyl-2,5-di(t-butylperoxy) hexane, diethyleneglycol-bis(t-butylperoxycarbonate), di-t-butylperoxy trimethylazipate, tris(t-butylperoxy) triazine, and vinyltris(t-butylperoxy) silane. These materials can be used singly or in combination. These materials are used at a concentration of at least 0.05 mass parts (preferably 0.1 to 15 mass parts) with respect to 100 mass parts of the monomer.

(Other Biodegradable Plastics)

In the present invention, the biodegradable plastics can also be used advantageously. Examples of the biodegradable plastics include "ECOSTAR" and "ECOSTAR PLUS" (trade names; available from Hagiwara Kogyo), "BIO-POLE" (trade name; available from I.C.I Japan), "AJI-COAT" (trade name; available from Ajinomoto), "PLAC-CELL" and "POLYCAPROLACTONE" (trade name; available from Daicel Chemical), "SHOREX" and "BION-ORE" (trade name; available from Showa Denko), "LACTY" (trade name; available from Shimadzu Corporation), "RAYCIA" (trade name; available from Mitsui Chemical) and "IUPEC" (trade name; available from Mitsubishi Gas Chemical).

In the combination of such binder resin and the charge control agent of the present invention, it is preferred that the polymer structure of the binder resin is as close as possible to that of the polymer chain of the charge control agent. If the polymer structure of the binder resin is significantly different from that of the polymer chain of the charge control agent, the dispersion thereof into the binder resin tends to become insufficient.

The mass ratio of the charge control agent of the present invention in case of internal addition to the binder resin is usually in a range of 0.1 to 50 mass %, preferably 0.3 to 30 mass % and more preferably 0.5 to 20 mass %. A mass ratio of the internally added charge control agent less than 0.1 mass % results in a low charge amount, while a mass ratio of the internally added charge control agent exceeding 50 mass % deteriorates the stability of toner charging.

(Coloring Agent)

The coloring agent for constituting the electrostatic latent image developing toner of the present invention is not particularly limited, and there can be utilized any coloring agent usually employed for toner preparation. For example there can be utilized carbon black, titanium white and any other pigment and/or dye. In case of using the electrostatic latent image developing toner of the present invention as magnetic color toner, the examples of the coloring agent include C.I. direct red 1, C.I. direct red 4, C.I. acid red 1, C.I. basic red 1, C.I. mordant red 30, C.I. direct blue 1, C.I. direct blue 2, C.I. acid blue 9, C.I. acid blue 15, C.I. basic blue 3, C.I. basic blue 5, C.I. mordant blue 7, C.I. direct green 6, C.I. basic green 4, and C.I. basic green 6. Examples of the pigment include lead yellow, cadmium yellow, mineral fast yellow, nable yellow, naphthol yellow S, Hanza yellow G, Permanent yellow NCG, tartrazine lake, lead reddish yellow, molybdenum orange, permanent orange GTR, pyrazolone orange, benzidine orange G, cadmium red, permanent red 4R, watching red calcium salt, eosine lake, brilliant carmine 3B, manganese violet, fast violet B, methyl violet lake, Prussian blue, cobalt blue, alkali blue lake, pictorial blue lake, phthalocyanine blue, fast sky blue, indanthrene blue BC, chromium green, chromium oxide, pigment green B, malachite green lake and final yellow green G.

In case of using the electrostatic latent image developing toner of the present invention as two-component full-color toner, following coloring agents can be used. The examples of the coloring agent for magenta toner include C.I. pigment red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, 209, C.I. pigment violet 19, C.I. vat red 1, 2, 10, 13, 15, 23, 29 and 35.

In the present invention, the above-mentioned pigment can be singly, but it is more preferable to use a dye and a pigment in combination to improve the sharpness, in consideration of the image quality of the full-color image. Examples of magenta dye usable in such case include oil-soluble dyes such as C.I. solvent red 1, 3, 8, 23, 24, 25, 27, 30, 49, 81, 82, 83, 84, 100, 109, 121, C.I. disperse red 9, C.I. solvent violet 8, 13, 14, 21, 27, or C.I. disperse violet 1; and basic dyes such as C.I. basic red 1, 2, 9, 12, 13, 14, 15, 17, 18, 22, 23, 24, 27, 29, 32, 34, 35, 36, 37, 38, 39, 40, C.I. basic violet 1, 3, 7, 10, 14, 15, 21, 25, 26, 27 or 28.

As other coloring pigments, the examples of cyan coloring pigment include C.I. pigment blue 2, 3, 15, 16, 17, C.I. vat blue 6, C.I. acid blue 45 and copper phthalocyanine dyes having 1 to 5 phthalimidemethyl radicals substituted on the phthalocyanine skeleton.

Examples of yellow coloring pigment include C.I. pigment yellow 1, 2, 3, 4, 5, 6, 7, 10, 11, 12, 13, 14, 15, 16, 17, 23, 65, 73, 83, C.I. vat yellow 1, 3 and 20.

The pigments and dyes mentioned above may be used singly or in an arbitrary mixture in order to obtain desired toner color. Also in case of considering environmental security or safety to the human body, various edible dyes can be used advantageously. The content of the coloring agent in the toner can be varied over a wide range according to the desired coloring effect. For obtaining the optimum toner characteristics, namely in consideration of the coloring power on the print, shape stability of toner and scattering of toner, such coloring agent is usually used in an amount of 0.1 to 60 mass parts, preferably 0.5 to 20 mass parts with respect to 100 mass parts of the binder resin.

(Other Components of Toner)

The electrostatic latent image developing toner of the present invention may include, in addition to the aforementioned binder resin and coloring agent, the following compounds within an extent not detrimentally affecting the effect of the present invention (not exceeding the content of the binder resin). Examples of such compound include silicone resin, aliphatic or alicyclic hydrocarbon resin such as polyester, polyurethane, polyamide, epoxy resin, polyvinylbutyral, rosin, denatured rosin, terpene resin, phenolic resin, low molecular weight polyethylene or low molecular weight polypropylene, aromatic petroleum resin, chlorinated paraffin and paraffin wax. Among these, there is preferably employed wax, and the examples thereof include low molecular weight polypropylene and byproducts thereof, low molecular weight polyester, ester wax and aliphatic derivatives. Wax classified by the molecular weight by means of various methods is also preferably employed in the present invention. After the classification, there may be also executed oxidation, block copolymerization or graft denaturing.

The electrostatic latent image developing toner of the present invention provides particularly excellent characteristics in case the toner includes the aforementioned wax component and such wax component is dispersed in substantially spherical- and/or spindle-shaped islands in the binder resin in the observation of the toner section under the transmission electron microscope (TEM).

(Method of Toner Preparation)

The electrostatic latent image developing toner of the present invention, having the above-described configuration, can be prepared by any known method. The electrostatic latent image developing toner of the present invention can be prepared by so-called pulverizing method for obtaining the toner by the following steps. More specifically, the electrostatic latent image developing toner of the present invention can be prepared by sufficiently mixing the aforementioned compound of the present invention, resins such as the binder resin and wax to be added if necessary by a mixer such as a Henshell mixer or a ball mill, then mutually dissolving the resins by fusion kneading with a heat kneader such as heated rollers, a kneader or an extruder, then dispersing or dissolving therein additives such as pigment, dye or magnetic material as the coloring agent, and a metallic compound to be added if necessary, then solidifying the mixture by cooling, pulverizing the solidified mixture with a pulverizer such as a jet mill or a ball mill and executing classification to a desired particle size. In the classifying step, there is preferably employed a multi-division classifier in consideration of the production efficiency.

The electrostatic latent image developing toner of the present invention can also be obtained by mixing the binder resin and the compound of the present invention in solution, utilizing solvent (for example aromatic hydrocarbon such as toluene or xylene, halogenated solvent such as chloroform or ethylene dichloride, ketone such as acetone or methylethyl-ketone, or amide such as dimethylformamide), charging the solution into water after agitation to achieve re-precipitation, then filtering and drying the precipitate, pulverizing the solid with a pulverizer such as a jet mill or a ball mill and executing classification to obtain the desired particle size. In the classifying step, there is preferably employed a multi-division classifier in consideration of the production efficiency.

The electrostatic latent image developing toner of the present invention can also be obtained by so-called polymerization method explained in the following. In this case, the compound of the present invention, a polymerizable monomer, a pigment, dye or magnetic material serving as the coloring agent, and a crosslinking agent, a polymerization initiator, wax and other additives if necessary are mixed and dispersed and are subjected to suspension polymerization in aqueous dispersion medium in the presence of a surfactant to obtain polymerized colored resin particles, which are then separated from the liquid phase, dried and subjected to classification if necessary to obtain the electrostatic latent image developing toner of the present invention.

It is also possible to prepare the colored particles without the charge control agent by the above-described methods and to fix the compound of the present invention singly or together with an externally added material such as colloidal silica onto the surface of the particles by a mechanochemical method.

(Externally Added Silica)

In the present invention, it is preferable to externally add, to the toner prepared in the above-described methods, fine silica powder in order to improve the charge stability, developability, flowability and durability. The fine silica powder to be employed for this purpose provides satisfactory result in case the specific surface area measured by the nitrogen absorption by the BET method is at least equal to 20 $m^2/g$ (particularly 30 to 400 $m^2/g$). In such case, the fine silica powder is used in an amount of 0.01 to 8 mass parts, preferably 0.1 to 5 mass parts, with respect to 100 mass parts of toner particles. The fine silica powder to be used is preferably processed, in necessary in order to control the hydrophobicity and charging ability, with silicone varnish, denatured silicon varnish, silicone oil, denatured silicone oil, silane coupling agent, silane coupling agent containing functional radicals, or othere organic silicon compounds. These processing agents may be used as a mixture.

(In Organic Powder)

It is also preferable to add the following inorganic powder in order to improve the developability and durability of the toner. Examples of such inorganic powder include oxides of metals such as magnesium, zinc, aluminum, cerium, cobalt, iron, zirconium, chromium, manganese, strontium, tin or antimony; complex metal oxides such as calcium titanate, magnesium titanate or strontium titanate; metal salts such as calcium carbonate, magnesium carbonate or aluminum carbonate; clay minerals such as caolin; phosphate compounds such as apatite; silicon compounds such as silicon carbide or silicon nitride; and carbon powder such as carbon black or graphite. Among these, particularly preferred is fine powder of zinc oxide, aluminum oxide, cobalt oxide, manganese dioxide, strontium titanate or magnesium titanate.

(Lubricant)

It is also possible to add following lubricant powder to the toner. Examples of such lubricant include fluorinated resins such as teflon polyfluoro-vinylidene; fluorinated compounds such as carbon fluoride; metal salts of fatty acids such as zinc stearate; fatty acid derivatives such as fatty acid or fatty acid ester; and molybdenum sulfide.

(Carrier)

The electrostatic latent image developing toner of the present invention can be used singly as the non-magnetic one-component developer, or applied to the conventionally known various toners such as non-magnetic toner constituting the magnetic two-component developer together with magnetic carrier or magnetic toner to be singly used as the magnetic one-component toner. In case of use in the two-component developing method, there can be utilized any known carrier. More specifically, the carrier particles can be constituted by particles of an average particle size of 20 to 300 μm composed of a surfacially oxidized or unoxidized metal such as iron, nickel, cobalt, manganese, chromium or a rare earth metal, or alloys or oxides thereof. The carrier to be employed in the present invention is preferably covered, on the surface of the carrier particles, with styrene resin, acrylic resin, silicone resin, fluorinated resin, polyester resin or the like.

(Magnetic Toner)

The electrostatic latent image developing toner of the present invention can also be formed as magnetic toner by including a magnetic material in the toner particles. In such case, the magnetic material may also serve as a coloring agent. Examples of such usable magnetic material include iron oxides such as magnetite, hematite or ferrite; metals such as iron, cobalt or nickel; and alloys of such metals with other metals such as aluminum, cobalt, copper, lead, magnesium, tin, zinc, antimony, beryllium, bismuth, cadmium, calcium, manganese, selenium, titanium, tungsten or vanadium; and mixtures thereof. Such magnetic material to be used in the present invention has an average particle size not exceeding 2 μm, preferably 0.1 to 0.5 μm. The content in the toner is preferably 20 to 200 mass parts, more preferably 40 to 150 mass parts with respect to 100 mass parts of the binder resin.

Also for achieving higher image quality, it is necessary to enable faithful development of smaller latent image dots, and, for this purpose, it is preferable that the electrostatic latent image developing toner of the present invention has a weight-averaged particle size within a range of 4 to 9 μm. The toner particles with a weight-averaged particle size less than 4 μm is undesirable because the transfer efficiency becomes lower to increase the toner amount remaining on the photosensitive member thereby resulting in image fog and uneven image caused by defective transfer. Also the toner particles with a weight-averaged particle size exceeding 9 μm tends to cause scattering of characters and line images.

In the present invention, the average particle size and the particle size distribution of the toner were measured with the Coulter Counter TA-II or Coulter Multisizer (supplied by Coulter Inc.) connected to an interface (supplied by Nippon Kagaku Kikai Co.) and a personal computer PC9801 (supplied by NEC) for outputting the number distribution and the volume distribution. As the electrolyte used in the measurement, there was prepared 1% NaCl aqueous solution with 1st grade sodium chloride. The electrolyte can also be for example composed of commercially available ISOTON R-II (supplied by Coulter Scientific Japan Inc.). In the measurement, a surfactant (preferably alkylbenzene sulfonate salt) as the dispersant was added in an amount of 0.1 to 5 ml to 100 to 150 ml of the aforementioned aqueous electrolyte solution, and a specimen for measurement was added by 2 to 20 mg to obtain the measurement sample. At the measurement, the electrolyte liquid in which the measurement specimen was suspended was subjected to dispersion for about 1 to 3 minutes by an ultrasonic disperser, and was subjected to the measurement of volume and number of toner of 2 μm or larger in the Coulter Counter TA-II with an aperture of 100 μm, thereby calculating the volume distribution and the number distribution. Then there were determined the weight-averaged particle size (D4) based on the volume calculated from the volume distribution of the present invention, and the length-averaged particle size (D1) based on the number calculated from the number distribution.

(Charge Amount)

The electrostatic latent image developing toner of the present invention preferably has a charge amount per unit mass (two component method) of −10 to −80 μC/g, preferably −15 to −70 μC/g in order to improve the transfer efficiency in the transfer method utilizing a voltage-applied transfer member.

Figure 7:
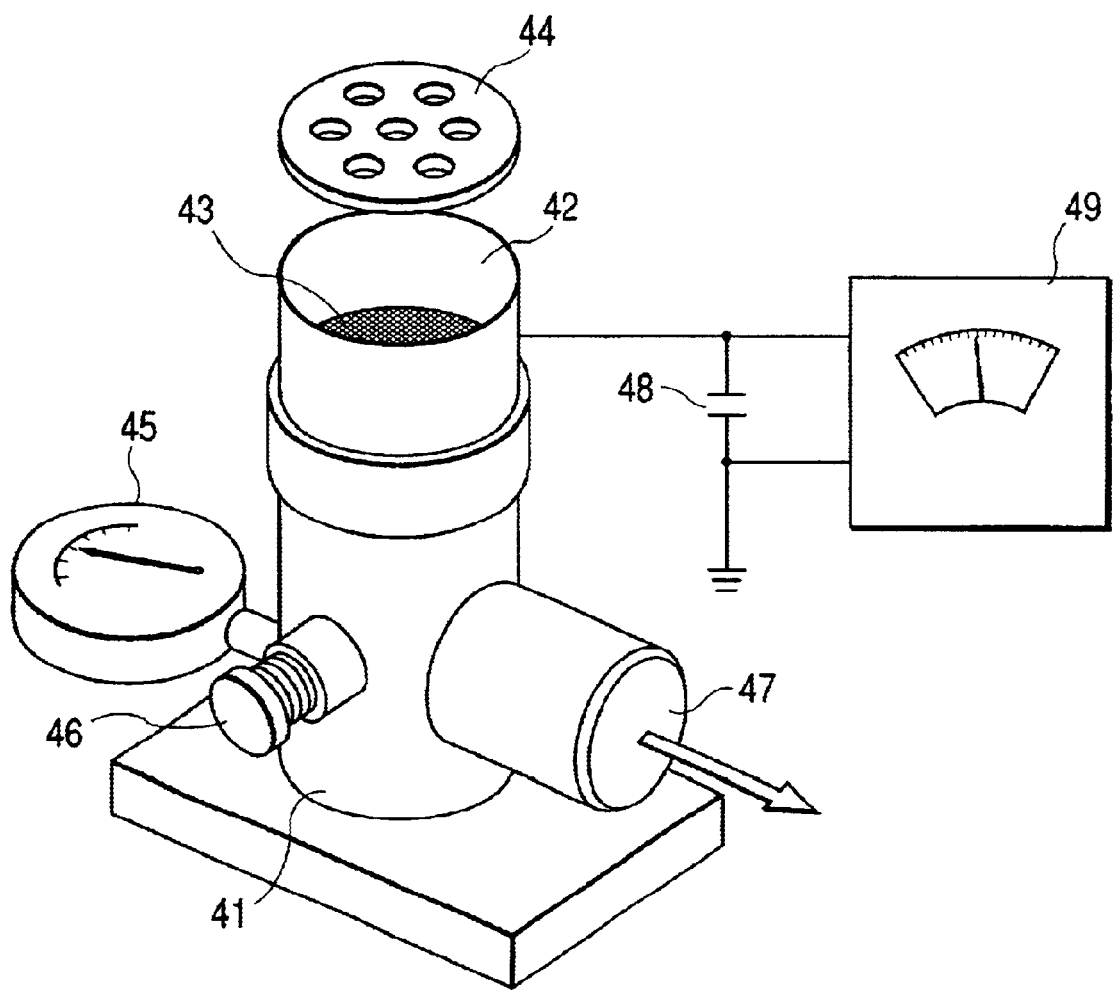
FIG. 7 is a schematic view showing a blow-off charge amount measuring apparatus for measuring the charge amount of toner.

In the following there will be explained the method for measuring the charge amount by the two-component method (two-component tribo) employed in the present invention. For the measurement, there was employed a charge amount measuring apparatus shown in FIG. 7. At first, a mixture consisting of 9.5 g of carrier, composed of EFV 299/300 (supplied by Powdertech Inc.) and 0.5 g of the toner to be measured, was charged in a polyethylene bottle of 50 to 100 ml, then placed on a vibrator of a constant amplitude and was shaked for a predetermined time under an amplitude of 100 mm and a vibrating speed of 100 cycle/minute. Then 1.0 to 1.2 g of the aforementioned mixture was charged in a metallic measurement container 42 of the charge amount measuring apparatus shown in FIG. 7, having a screen 43 of 500 mesh at the bottom, and a metal cover 44 was placed. The mass of the entire measurement container 42 was measured as W1 (g). Then suction was executed with an unrepresented suction device (made insulating at least in a portion in contact with the measurement container 22) from a suction aperture 47, and an air amount adjusting valve 46 was so adjusted that a vacuum meter 45 indicated a pressure of 2450 Pa (250 mm Aq). The suction was executed for 1 minute in this state to eliminate the toner by suction. The potential indicated by a potential meter 49 was selected as V (volt). A capacitor 48 had a capacity C ($\mu$F). The mass of the entire measurement container after sucking was measured as W2 (g). The triboelectric charge amount of the toner ($\mu$C/g) was calculated from these measured values according to the following formula:

Triboelectric charge amount ($\mu$C/g)=C×V/(W1−W2).

(Molecular Weight Distribution of Binder Resin)

The binder resin to be employed as a constituent of the electrostatic latent image developing toner of the present invention preferably has, particularly in case of preparation by the pulverizing method, a peak in the low molecular weight range in the GPC molecular weight distribution within a range of 3,000 to 15,000. If the GPC peak in the low molecular weight range exceeds 15,000, the transfer efficiency may become insufficient. Also the binder resin having a GPC peak in the low molecular weight range less than 3,000 is undesirable because fusion tends to be caused at the surface treatment.

In the present invention, the molecular weight of the binder resin was measured by GPC (gel permeation chromatography). More specifically, the molecular weight measurement by the GPC was executed by employing a sample obtained by extracting the toner with THF (tetrahydrofurane) for 20 hours in a Soxlet extractor, also employing a column configuration formed by connecting A-801, 802, 803, 804, 805, 806 and 807 supplied by Showa Denko Co. and utilizing a calibration line of standard polystyrene resin. Also in the present invention, it is preferable to use binder resin having a ratio (Mw/Mn) of the weight-average molecular weight (Mw) and the number average molecular weight (Mn), measured as explained in the foregoing, within a range of 2 to 100.

(Glass Transition Point of Toner)

Furthermore, the toner of the present invention is so prepared, with suitable materials, as to have a glass transition point Tg preferably within a range of 40 to 75° C., more preferably 52 to 70° C. in consideration of the fixability and storability. The glass transition point Tg can be measured, for example, by a highly precise scanning differential thermal analyzer of internal input compensation type such as Perkin Elmer DSC-7. The measurement is executed according to ASTM D3418-82. In the present invention, the measurement of the glass transition point is preferably executed by once heating the specimen to eliminate the prior hysteresis, then rapidly cooling the specimen and utilizing a DSC curve obtained heating the specimen again within a range of 0 to 200° C. with a heating rate of 10° C./min.

(Image Forming Method)

The electrostatic latent image developing toner of the present invention having the aforementioned configuration is particularly preferably applied to an image forming method at least comprising a charging step of externally applying a voltage to a charging member thereby charging an electrostatic latent image bearing member, a step of forming an electrostatic latent image on the charged electrostatic latent image bearing member, a development step of developing the electrostatic latent image with electrostatic latent image developing toner thereby forming a toner image on the electrostatic latent image bearing member, a transfer step of transferring the toner image on the electrostatic latent image bearing member onto a recording material, and a heat fixation step of heat fixing the toner image on the recording material, or an image forming method in which the above-mentioned transfer step consists of a first transfer step of transferring the toner image on the electrostatic latent image bearing member onto an intermediate transfer member and a second transfer step of transferring the toner image on the intermediate transfer member onto the recording material.

EXAMPLES

In the following, the present invention will be explained in more details by examples thereof. These examples represent examples of the optimum embodiments of the present invention, but the present invention is by no means limited by these examples.

At first the following examples 1 to 10 show production of PHA including, in the polymer molecule, the 3-hydroxy-5-(2-thienylsulfinyl) valeric acid unit of the chemical formula (9), the 3-hydroxy-5-(2-thienylsulfonyl) valeric acid unit of the chemical formula (10), and at least a chloro-substituted unit among the following four units, namely the 5-chloro-3-hydroxy-5-(2-thienylsulfinyl) valeric acid unit of the chemical formula (11), 5-chloro-3-hydroxy-5-(2-thienylsulfonyl) valeric acid unit of the chemical formula (12), 5,5-dichloro-3-hydroxy-5-(2-thienylsulfinyl) valeric acid unit of the chemical formula (13) and 5,5-dichloro-3-hydroxy-5-(2-thienylsulfonyl) valeric acid unit of the chemical formula (14), by culturing PHA producing bacteria in a culture medium containing 5-(2-thienylsulfanyl) valeric acid as a raw material, and then processing PHA produced by the PHA producing bacteria with sodium hypochlorite.

Example 1

1000 ml of M9 culture medium containing 0.5% of commercial polypeptone (supplied by Wako Chemical Co.) and 0.1% of 5-(2-thienylsulfanyl) valeric acid was charged in a 2000 ml shaking flask, then the strain YN2 was inoculated and shaking culture was executed for 62 hours under conditions of 30° C. and 125 stroke/minute. The bacteria cells were recovered from the obtained culture liquid by centrifuging (78000 m/S$^2$(=8000G), 4° C., 10 minutes).

The recovered cells were suspended in 40 ml of purified water, and 20 ml of sodium hypochlorite aqueous solution (supplied by Kishida Chemical Co., effective chlorine concentration 5% or higher) was added. The mixture was shaked for 2 hours at 4° C., to solubilize the cell components other than the desired PHA and to oxidize and chlorinate PHA. After the reaction, the PHA was separated and recovered as an insoluble component from the process liquid by centrifuging (29400 M/S$^2$(=3000G), 4° C., 30 minutes). The separated PHA was again suspended in 70 ml of purified water, and the PHA was again separated and recovered by centrifuging (29400 m/S$^2$(=3000G), 4° C., 30 minutes). The re-suspension and centrifuging were repeated in three cycles in total to rinse the PHA. Finally, the rinsed PHA was suspended in 10 ml of purified water and was lyophilized to obtain 445 mg (dry weight) of PHA particles.

The average molecular weight of obtained PHA was measured by gel permeation chromatography (GPC) under the following conditions:

apparatus: Toso HLC-8020;
column: Polymer Laboratory PLgel MIXED-C (5 μm)×2;
moving layer solvent: DMF containing 0.1 mass % LiBr:
and was obtained as the molecular weight converted into polystyrene. Also structure of obtained PHA was measured by proton-nucleomagnetic resonance ($^1$H-NMR) under the following conditions:

apparatus: Bruker DPX400 FT-NMR;
$^1$H resonance frequency: 400 MHz;
measured nucleus species: $^1$H;
solvent: CDCl$_3$;
reference: capillary-sealed TMS/CDCl$_3$;
measurement temperature: room temperature.

Figure 8:
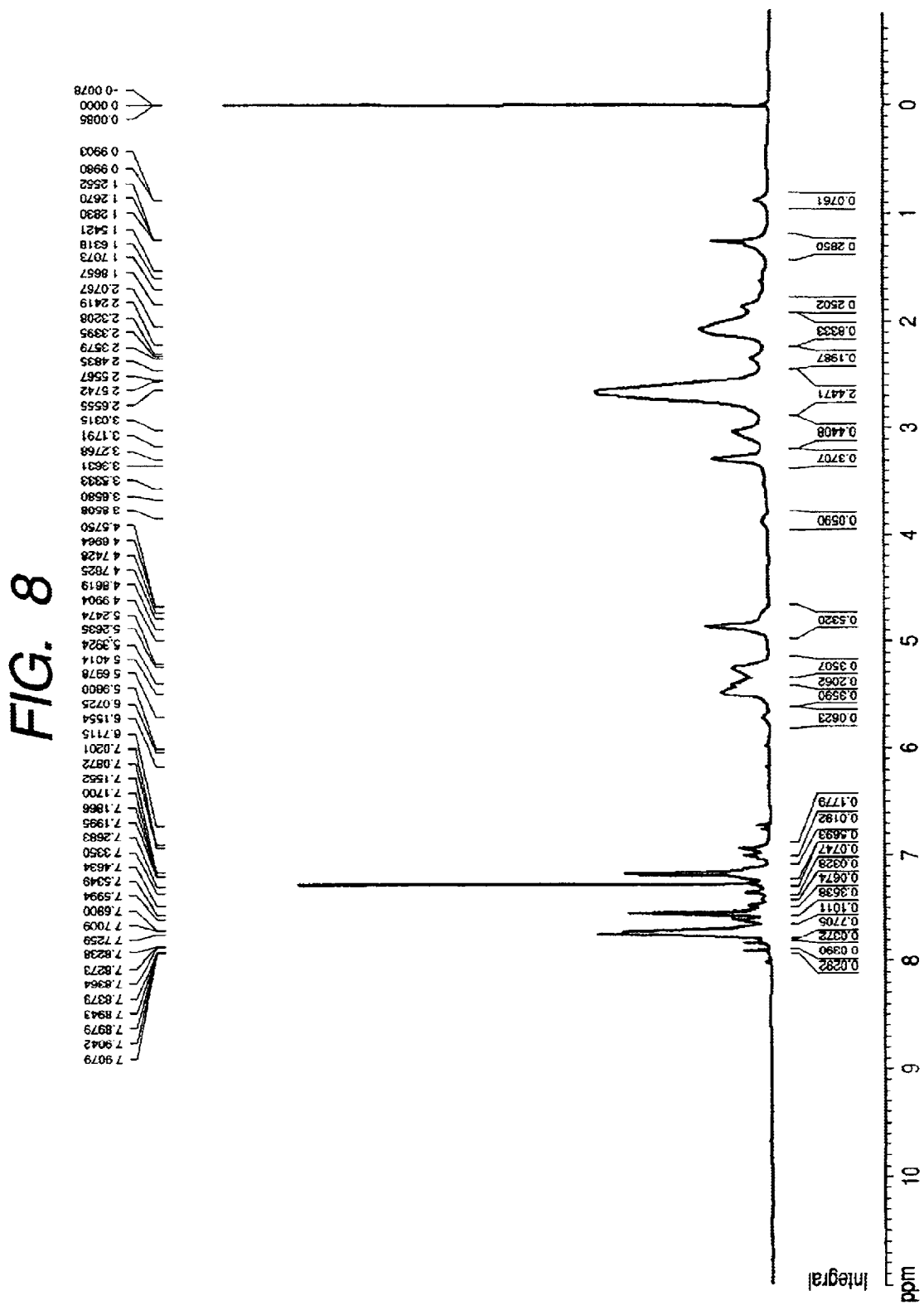
FIG. 8 is a chart showing $^1$H-NMR spectrum of a sample obtained in the example 1.

FIG. 8 shows the obtained chart of measured $^1$H-NMR spectrum, and Table 1 shows the result of calculation of the content (mol %) of the monomer unit based on the measurement by the $^1$H-NMR. Also the PHA has a number average molecular weight (Mn) of 11,000, a weight average molecular weight (Mw) of 17,900 and a ratio Mw/Mn of 1.6.

The $^1$H-NMR analysis indicated that, in the obtained PHA, 3-hydroxy-5-(2-thienylsulfanyl) valeric acid unit contained in the precursor PHA produced by the YN2 strain from the starting 5-(2-thienylsulfanyl) valeric acid is converted by processing with sodium hypochlorite into 3-hydroxy-5-(2-thienylsulfinyl) valeric acid unit of the chemical formula (9), 3-hydroxy-5-(2-thienylsulfonyl) valeric acid unit of the chemical formula (10), 5-chloro-3-hydroxy-5-(2-thienylsulfinyl) valeric acid unit of the chemical formula (11), 5-chloro-3-hydroxy-5-(2-thienylsulfonyl) valeric acid unit of the chemical formula (12), 5,5-dichloro-3-hydroxy-5-(2-thienylsulfinyl) valeric acid unit of the chemical formula (13) and 5,5-dichloro-3-hydroxy-5-(2-thienylsulfonyl) valeric acid unit of the chemical formula (14). In addition it was confirmed that PHA included, as other units, a straight-chain 3-hydroxy alkanoic acid unit with 4 to 12 carbon atoms of the general formula (7) or a straight-chain 3-hydroxyalk-5-enoic acid unit of the general formula (8). In Table 1, the straight-chain 3-hydroxy alkanoic acid unit with 4 to 12 carbon atoms of the general formula 5 (7) and the straight-chain 3-hydroxyalkenoic acid unit of the general formula (8) are collectively indicated as 3HA.

TABLE 1

| Kinds of units | NMR (mol %) |
| --- | --- |
| formulas (9) and (10) | 18.8 |
| formulas (11) and (12) | 53.8 |
| formulas (13) and (14) | 6.3 |
| 3HA | 21.1 |

The units of the chemical formulas (9) and (10), those of the chemical formulas (11) and (12) or those of the chemical formulas (13) and (14) are difficult to individually identify the amounts by NMR, so that Table 1 shows the amounts in total. In consideration of the results of infrared absorption spectrum and thermal decomposition GC-MC analysis in addition to the NMR analysis, it was concluded that the polymer contained all the aforementioned chloro-substituted units.

Example 2

1000 ml of M9 culture medium containing 0.5% of commercial polypeptone (supplied by Wako Chemical Co.) and 0.1% of 5-(2-thienylsulfanyl) valeric acid was charged in a 2000 ml shaking flask, then the strain H45 was inoculated and shaking culture was executed for 62 hours under conditions of 30° C. and 125 stroke/minute. The bacteria cells were recovered from the obtained culture liquid by centrifuging (78000 m/S$^2$(=8000G), 4° C., 10 minutes).

The obtained cells were processed with sodium hypochlorite under the conditions similar to those in the example 1 to obtain 255 mg (dry weight) of polyhydroxyalkanoate.

Example 3

1000 ml of M9 culture medium containing 0.5% of commercial polypeptone (supplied by Wako Chemical Co.) and 0.1% of 5-(2-thienylsulfanyl) valeric acid was charged in a 2000 ml shaking flask, then the strain P161 was inoculated and shaking culture was executed for 62 hours under conditions of 30° C. and 125 stroke/minute. The bacteria cells were recovered from the obtained culture liquid by centrifuging (78000 m/S$^2$(=8000G), 4° C., 10 minutes).

The obtained cells were processed with sodium hypochlorite under the conditions similar to those in the example 1 to obtain 220 mg (dry weight) of polyhydroxyalkanoate.

Example 4

1000 ml of M9 culture medium containing 0.5% of glucose and 0.1% of 5-(2-thienylsulfanyl) valeric acid was charged in a 2000 ml shaking flask, then the strain YN2 was inoculated and shaking culture was executed for 45 hours under conditions of 30° C. and 125 stroke/minute. The cultured bacteria were recovered from the obtained culture liquid by centrifuging. The recovered cultured bacteria were re-suspended in 1000 ml of M9 culture medium containing 0.5% of glucose and 0.1% of 5-(2-thienylsulfanyl) valeric acid but not containing nitrogen source (NH$_4$Cl), and were subjected to shaking culture in a 2000 ml shaking flask for 48 hours under conditions of 30° C. and 125 stroke/minute. The bacteria cells were recovered from the culture liquid by centrifuging (78000 m/S$^2$(=8000G), 4° C., 10 minutes).

The obtained cells were processed with sodium hypochlorite under the conditions similar to those in the example 1 to obtain 960 mg (dry weight) of polyhydroxyalkanoate.

Example 5

1000 ml of M9 culture medium containing 0.5% of glycerol and 0.1% of 5-(2-thienylsulfanyl) valeric acid was charged in a 2000 ml shaking flask, then the strain YN2 was inoculated and shaking culture was executed for 45 hours under conditions of 30° C. and 125 stroke/minute. The cultured bacteria were recovered from the obtained culture liquid by centrifuging. The recovered cultured bacteria were re-suspended in 1000 ml of M9 culture medium containing 0.5% of glycerol and 0.1% of 5-(2-thienylsulfanyl) valeric acid but not containing nitrogen source (NH$_4$Cl), and were subjected to shaking culture in a 2000 ml shaking flask for 48 hours under conditions of 30° C. and 125 stroke/minute. The bacteria cells were recovered from the culture liquid by centrifuging (78000 m/S$^2$(=8000G), 4° C., 10 minutes).

The obtained cells were processed with sodium hypochlorite under the conditions similar to those in the example 1 to obtain 830 mg (dry weight) of polyhydroxyalkanoate.

Example 6

1000 ml of M9 culture medium containing 0.5% of polypeptone and 0.1% of 5-(2-thienylsulfanyl) valeric acid was charged in a 2000 ml shaking flask, then the strain YN2 was inoculated and shaking culture was executed for 45 hours under conditions of 30° C. and 125 stroke/minute. The cultured bacteria were recovered from the obtained culture liquid by centrifuging. The recovered cultured bacteria were re-suspended in 1000 ml of M9 culture medium containing 0.5% of sodium pyruvate and 0.1% of 5-(2-thienylsulfanyl) valeric acid but not containing nitrogen source (NH$_4$Cl), and were subjected to shaking culture in a 2000 ml shaking flask for 48 hours under conditions of 30° C. and 125 stroke/minute. The bacteria cells were recovered from the culture liquid by centrifuging (78000 m/S$^2$(=8000G), 4° C., 10 minutes).

The obtained cells were processed with sodium hypochlorite under the conditions similar to those in the example 1 to obtain 1410 mg (dry weight) of polyhydroxyalkanoate.

Example 7

1000 ml of M9 culture medium containing 0.5% of commercial yeast extract (supplied by Difco Co.) and 0.1% of 5-(2-thienylsulfanyl) valeric acid was charged in a 2000 ml shaking flask, then the strain YN2 was inoculated and shaking culture was executed for 62 hours under conditions of 30° C. and 125 stroke/minute. The cultured bacteria were recovered from the culture liquid by centrifuging (78000 m/S$^2$(=8000G), 4° C., 10 minutes).

The obtained cells were processed with sodium hypochlorite under the conditions similar to those in the example 1 to obtain 120 mg (dry weight) of polyhydroxyalkanoate.

Example 8

1000 ml of M9 culture medium containing 0.5% of sodium pyruvate and 0.1% of 5-(2-thienylsulfanyl) valeric acid was charged in a 2000 ml shaking flask, then the strain YN2 was inoculated and shaking culture was executed for 62 hours under conditions of 30° C. and 125 stroke/minute. The cultured bacteria were recovered from the culture liquid by centrifuging (78000 m/S$^2$(=8000G), 4° C., 10 minutes).

The obtained cells were processed with sodium hypochlorite under the conditions similar to those in the example 1 to obtain 425 mg (dry weight) of polyhydroxyalkanoate.

Example 9

1000 ml of M9 culture medium containing 0.5% of sodium glutamate and 0.1% of 5-(2-thienylsulfanyl) valeric acid was charged in a 2000 ml shaking flask, then the strain YN2 was inoculated and shaking culture was executed for 62 hours under conditions of 30° C. and 125 stroke/minute. The cultured bacteria were recovered from the culture liquid by centrifuging (78000 m/S$^2$(=8000G), 4° C., 10 minutes).

The obtained cells were processed with sodium hypochlorite under the conditions similar to those in the example 1 to obtain 410 mg (dry weight) of polyhydroxyalkanoate.

Example 10

1000 ml of M9 culture medium containing 0.1% of nonanoic acid and 0.1% of 5-(2-thienylsulfanyl) valeric acid was charged in a 2000 ml shaking flask, then the strain YN2 was inoculated and shaking culture was executed for 62 hours under conditions of 30° C. and 125 stroke/minute. The cultured bacteria were recovered from the culture liquid by centrifuging (78000 m/S$^2$(=8000G), 4° C., 10 minutes).

The obtained cells were processed with sodium hypochlorite under the conditions similar to those in the example 1 to obtain 430 mg (dry weight) of polyhydroxyalkanoate.

The polyhydroxyalkanoates obtained in the foregoing examples 2 to 10 were subjected to the NMR analysis and molecular weight measurement under the same conditions as those in the example 1. Table 2 shows the contents of the units calculated from the result of NMR analysis, and Table 3 shows the average molecular weights. In Table 2, the straight-chain 3-hydroxy alkanoic acid unit with 4 to 12 carbon atoms of the general formula (6) and the straight-chain 3-hydroxyalkenoic acid unit of the general formula (7) are collectively indicated as 3HA.

TABLE 2

|  | PHA (mg) | Unit content (mol %) | | | |
| --- | --- | --- | --- | --- | --- |
|  |  | formulas (9) & (10) | formulas (11) & (12) | formulas (13) & (14) | 3HA |
| Ex. 2 | 255 | 19.3 | 65.4 | 7.3 | 8.0 |
| Ex. 3 | 220 | 19.6 | 65.5 | 7.4 | 7.5 |
| Ex. 4 | 960 | 20.3 | 60.7 | 7.5 | 11.5 |
| Ex. 5 | 830 | 19.7 | 55.5 | 7.4 | 17.4 |
| Ex. 6 | 1410 | 21.1 | 63.3 | 7.2 | 8.4 |
| Ex. 7 | 120 | 21.0 | 61.9 | 7.0 | 10.1 |
| Ex. 8 | 425 | 21.5 | 62.4 | 5.6 | 10.5 |
| Ex. 9 | 410 | 21.9 | 61.9 | 7.3 | 8.9 |
| Ex. 10 | 430 | 1.8 | 5.1 | 0.6 | 92.5 |

TABLE 3

|  | Mn | Mw | Mw/Mn |
| --- | --- | --- | --- |
| Ex. 2 | 12100 | 19800 | 1.6 |
| Ex. 3 | 10700 | 18200 | 1.7 |
| Ex. 4 | 12300 | 18500 | 1.5 |
| Ex. 5 | 11300 | 18400 | 1.6 |
| Ex. 6 | 10900 | 17400 | 1.6 |
| Ex. 7 | 10800 | 18300 | 1.7 |
| Ex. 8 | 12500 | 20400 | 1.6 |
| Ex. 9 | 12000 | 20400 | 1.7 |
| Ex. 10 | 12100 | 19300 | 1.6 |

The following examples 11 to 14 show production of PHA including, in the polymer molecule, 3-hydroxy-6-(2-thienylsulfinyl) hexanoic acid unit of the chemical formula (21), 3-hydroxy-6-(2-thienylsulfonyl) hexanoic acid unit of the chemical formula (22), at least a chloro-substituted unit among the following four units, namely 6-chloro-3-hydroxy-6-(2-thienylsulfinyl) hexanoic acid unit of the chemical formula (23), 6-chloro-3-hydroxy-6-(2-thienylsulfonyl) hexanoic acid unit of the chemical formula (24), 6,6-dichloro-3-hydroxy-6-(2-thienylsulfinyl) hexanoic acid unit of the chemical formula (25) and 6,6-dichloro-3-hydroxy-6-(2-thienylsulfonyl) hexanoic acid unit of the chemical formula (26), 3-hydroxy-4-(2-thienylsulfinyl) butyric acid unit of the chemical formula (15), 3-hydroxy-4-(2-thienylsulfonyl) butyric acid unit of the chemical formula (16), and at least a chloro-substituted unit among the following four units, namely 4-chloro-3-hydroxy-4-(2- thienylsulfinyl) butyric acid unit of the chemical formula (17), 4-chloro-3-hydroxy-4-(2-thienylsulfonyl) butyric acid unit of the chemical formula (18), 4,4-dichloro-3-hydroxy-4-(2-thienylsulfinyl) butyric acid unit of the chemical formula (19) and 4,4-dichloro-3-hydroxy-4-(2-thienylsulfonyl) butyric acid unit of the chemical formula (20), by culturing PHA producing bacteria in a culture medium containing the starting 6-(2-thienylsulfanyl) hexanoic acid, and then processing PHA produced by the PHA producing bacteria with sodium hypochlorite.

Example 11

1000 ml of M9 culture medium containing 0.5% of commercial polypeptone (supplied by Wako Chemical Co.) and 0.1% of 6-(2-thienylsulfanyl) hexanoic acid was charged in a 2000 ml shaking flask, then the strain YN2 was inoculated and shaking culture was executed for 30 hours under conditions of 30° C. and 125 stroke/minute. The bacteria cells were recovered from the obtained culture liquid by centrifuging (78000 m/S$^2$(=8000G), 4° C., 10 minutes).

The recovered cells were suspended in 40 ml of purified water, and 20 ml of sodium hypochlorite aqueous solution (supplied by Kishida Chemical Co., effective chlorine concentration 5% or higher) was added. The mixture was shaked for 2 hours at 4° C., to solubilize the cell components other than the desired PHA and to oxidize and chlorinate PHA. After the reaction, the PHA was separated and recovered as an insoluble component from the process liquid by centrifuging (29400 m/S$^2$(=3000G), 4° C., 30 minutes). The separated PHA was again suspended in 70 ml of purified water, and the PHA was separated and recovered by centrifuging (29400 m/S$^2$(=3000G), 4° C., 30 minutes). The re-suspension and centrifuging were repeated in three cycles in total to rinse the PHA. Finally, the rinsed PHA was suspended in 10 ml of purified water and was lyophilized to obtain 440 mg (dry weight) of PHA particles.

The polyhydroxyalkanoate obtained in the example 11 was subjected to the NMR analysis and molecular weight measurement under the same conditions as those in the example 1. Table 4 shows the contents of the units (mol %) calculated from the result of NMR analysis. In Table 4, the straight-chain 3-hydroxy alkanoic acid unit with 4 to 12 carbon atoms of the general formula (7) and the straight-chain 3-hydroxyalkenoic acid unit of the general formula (8) are collectively indicated as 3HA. Also the PHA had a number average molecular weight (Mn) of 3800, a weight average molecular weight (Mw) of 6500 and a ratio Mw/Mn of 1.7.

It was confirmed that the obtained polyhydroxyalkanoate contained 3-hydroxy-4-(2-thienylsulfinyl) butyric acid unit of the chemical formula (15), 3-hydroxy-4-(2-thienylsulfonyl) butyric acid unit of the chemical formula (16), 4-chloro-3-hydroxy-4-(2-thienylsulfinyl) butyric acid unit of the chemical formula (17), 4-chloro-3-hydroxy-4-(2-thienylsulfonyl) butyric acid unit of the chemical formula (18), 4,4-dichloro-3-hydroxy-4-(2-thienylsulfinyl) butyric acid unit of the chemical formula (19) and 4,4-dichloro-3-hydroxy-4-(2-thienylsulfonyl) butyric acid unit of the chemical formula (20), 3-hydroxy-6-(2-thienylsulfinyl) hexanoic acid unit of the chemical formula (21), 3-hydroxy-6-(2-thienylsulfonyl) hexanoic acid unit of the chemical formula (22), 6-chloro-3-hydroxy-6-(2-thienylsulfinyl) hexanoic acid unit of the chemical formula (23), 6-chloro-3-hydroxy-6-(2-thienylsulfonyl) hexanoic acid unit of the chemical formula (24), 6,6-dichloro-3-hydroxy-6-(2-thienylsulfinyl) hexanoic acid unit of the chemical formula (25), and 6,6-dichloro-3-hydroxy-6-(2-thienylsulfonyl) hexanoic acid unit of the chemical formula (26), and also as another unit, straight-chain 3-hydroxy alkanoic acid unit with 4 to 12 carbon atoms of the general formula (7) and straight-chain 3-hydroxyalkenoic acid unit of the general formula (8).

TABLE 4

| Kinds of units | NMR (mol %) |
| --- | --- |
| formulas (15) and (16) | 10.9 |
| formulas (17) and (18) | 31.3 |
| formulas (19) and (20) | 3.8 |
| formulas (21) and (22) | 8.5 |
| formulas (23) and (24) | 23.8 |
| formulas (25) and (26) | 2.7 |
| 3HA | 19.0 |

The units of the chemical formulas (15) and (16), those of the chemical formulas (17) and (18), those of the chemical formulas (19) and (20), those of the chemical formulas (21) and (22), those of the chemical formulas (23) and (24) or those of the chemical formulas (25) and (26) are difficult to individually identify the amounts by NMR, so that Table 4 shows the amounts in total. In consideration of the results of infrared absorption spectrum and thermal decomposition GC-MC analysis in addition to the NMR analysis, it was concluded that the polymer contained all the aforementioned chloro-substituted units.

Example 12

1000 ml of M9 culture medium containing 0.5% of commercial polypeptone (supplied by Wako Chemical Co.) and 0.1% of 6-(2-thienylsulfanyl) hexanoic acid was charged in a 2000 ml shaking flask, then the strain H45 was inoculated and shaking culture was executed for 30 hours under conditions of 30° C. and 125 stroke/minute. The bacteria cells were recovered from the obtained culture liquid by centrifuging (78000 m/S$^2$(=8000G), 4° C., 10 minutes).

The obtained cells were processed with sodium hypochlorite under the conditions similar to those in the example 11 to obtain 155 mg (dry weight) of polyhydroxyalkanoate.

Example 13

1000 ml of M9 culture medium containing 0.5% of commercial polypeptone (supplied by Wako Chemical Co.) and 0.1% of 6-(2-thienylsulfanyl) hexanoic acid was charged in a 2000 ml shaking flask, then the strain P161 was inoculated and shaking culture was executed for 30 hours under conditions of 30° C. and 125 stroke/minute. The bacteria cells were recovered from the obtained culture liquid by centrifuging (78000 m/S$^2$(=8000G), 4° C., 10 minutes).

The obtained cells were processed with sodium hypochlorite under the conditions similar to those in the example 11 to obtain 100 mg (dry weight) of polyhydroxyalkanoate.

Example 14

1000 ml of M9 culture medium containing 0.5% of glucose and 0.1% of 6-(2-thienylsulfanyl) hexanoic acid was charged in a 2000 ml shaking flask, then the strain YN2 was inoculated and shaking culture was executed for 45 hours under conditions of 30° C. and 125 stroke/minute. The cultured bacteria were recovered from the obtained culture liquid by centrifuging. The recovered cultured bacteria were re-suspended in 1000 ml of M9 culture medium containing 0.5% of glucose and 0.1% of 6-(2-thienylsulfanyl) hexanoic acid but not containing nitrogen source ($NH_4Cl$) and subjected to shaking culture in a 2000 ml shaking flask for 48 hours under conditions of 30° C. and 125 stroke/minute. The bacteria cells were recovered from the obtained culture liquid by centrifuging (78000 m/$S^2$(=8000G), 4° C., 10 minutes).

The obtained cells were processed with sodium hypochlorite under the conditions similar to those in the example 11 to obtain 195 mg (dry weight) of polyhydroxyalkanoate.

The polyhydroxyalkanoates obtained in the examples 12 to 14 were subjected to the NMR analysis and molecular weight measurement under the same conditions as those in the example 1. Table 5 shows the contents of the units (mol %) calculated from the result of NMR analysis. Also Table 6 shows the average molecular weight. In Table 5, the straight-chain 3-hydroxy alkanoic acid unit with 4 to 12 carbon atoms of the general formula (7) and the straight-chain 3-hydroxyalkenoic acid unit of the general formula (8) are collectively indicated as 3HA.

TABLE 5

| | PHA (mg) | (15) & (16) | (17) & (18) | (19) & (20) | (21) & (22) | (23) & (24) | (25) & (26) | 3HA |
|---|---|---|---|---|---|---|---|---|
| | | | | Unit content (mol %) | | | | |
| Ex. 12 | 155 | 14.8 | 42.4 | 5.0 | 6.3 | 18.6 | 2.4 | 10.5 |
| Ex. 13 | 100 | 15.8 | 45.2 | 5.3 | 4.9 | 13.9 | 1.6 | 13.3 |
| Ex. 14 | 195 | 8.2 | 23.7 | 3.1 | 10.9 | 30.0 | 4.0 | 20.1 |

TABLE 6

| | Mn | Mw | Mw/Mn |
|---|---|---|---|
| Ex. 12 | 3100 | 5300 | 1.7 |
| Ex. 13 | 2700 | 4500 | 1.7 |
| Ex. 14 | 3500 | 6400 | 1.8 |

The compounds obtained in the foregoing examples 1 to 3 and 11 to 13 were taken as example compounds (1) to (6) as shown in Table 7, and were used as the charge control agents in the preparations of various toners and were evaluated (examples 15 to

TABLE 7

| Example 1 | Example compound (1) |
| Example 2 | Example compound (2) |
| Example 3 | Example compound (3) |
| Example 11 | Example compound (4) |
| Example 12 | Example compound (5) |
| Example 13 | Example compound (6) |

Example 15

At first $Na_3PO_4$ aqueous solution was charged in a 2-liter 4-neck flask with a high-speed agitator TK-Homomixer, and was heated to 60° C. under agitation of 10,000 rpm. Then $CaCl_2$ aqueous solution was gradually added to prepare aqueous dispersion medium containing hardly water-soluble dispersant $Ca_3(PO_4)_2$ in finely dispersed state.

On the other hand, the following composition was dispersed for 3 hours in a ball mill, and added with 10 mass parts of releasing agent (ester wax) and 10 mass parts of 2,2'-azobis-(2,4-dimethylvalero-nitrile) as a polymerization initiator to obtain a polymerizable monomer composition:

| styrene monomer | 82 mass parts |
| ethylhexyl acrylate monomer | 18 mass parts |
| divinylbenzene monomer | 0.1 mass parts |
| cyan coloring agent | 6 mass parts |
| (C.I. pigment blue 15) | |
| oxidized polyethylene resin | 5 mass parts |
| (molecular weight: 3200, acid value 8) | |
| example compound (1) | 2 mass parts. |

Then, thus obtained polymerizable monomer composition was charged into the above-prepared aqueous dispersion medium and particles were formed under agitation of 10,000 rpm. Then reaction was executed for 3 hours at 65° C. under agitation with a paddle agitator, and polymerization was executed for 6 hours at 80° C. to terminate the polymerization. After the reaction, the suspension was cooled, then added with acid to dissolve the hardly water-soluble dispersant $Ca_3(PO_4)_2$, further filtered, rinsed with water and dried to obtain blue polymer particles (1). The obtained blue polymer particles (1) had a weight-averated particle size of 7.2 μm as measured by the Coulter Counter Multisizer (supplied by Coulter Inc.) and a fine powder amount (proportion of the particles not exceeding 3.17 μm in the number distribution) of 5.1 number %.

100 mass parts of thus prepared blue polymer particles (1) were externally added, by dry mixing with a Henshell mixer, with 1.3 mass parts of hydrophobic silica powder (BET: 270 $m^2$/g) treated with hexamethyl disilazane as the flowability improving agent, to obtain blue toner (1) of the present example. Further, 7 mass parts of the blue toner (1) and 93 mass parts of resin-coated magnetic ferrite carrier (average particle size 45 μm) to obtain two-component blue developer (1) for magnetic brush development.

Examples 16 to 20

Blue toners (2) to (6) of the examples 16 to 20 were obtained by a method similar to that in the example 15 except that the example compound (1) was respectively replaced by example compounds (2) to (6). The characteristics of these toners were measured as in the example 15, and the results are shown in Table 8. Also these toners were used as in the example 15 to respectively obtain two-component blue developers (2) to (6).

Comparative Example 1

Blue toner 7 of the comparative example 1 was obtained by a method similar to that of the example 15, except that the example compound was not used. The characteristics of such toner were measured as in the example 15, and the results are shown in Table 8. Also such toner was used as in the example 15 to obtain two-component blue developer 7.

<Evaluation>

The two-component blue developers (1) to (6) obtained in the examples 15 to 20 and the two-component blue developer 7 obtained in the comparative example 1 were subjected to the measurement of toner charge amount after agitation for 10 or 300 seconds, by the aforementioned charge amount measuring method, respectively under an environment of normal temperature and normal humidity (25° C., 60% RH) and an environment of high temperature and high humidity (30° C., 80% RH). The measured value of the two-component blow-off charge amount was rounded at the second place under fractional point, and was evaluated by the following criteria. The results are summarized in Table 8:

⊚: very satisfactory (not exceeding −20 μC/g);
○: satisfactory (−19.9 to −10.0 μC/g);
Δ: practically acceptable (−9.9 to −5.0 μC/g);
X: practically unacceptable (−4.9 μC/g or higher).

TABLE 8

Charging characteristics of blue toners (1) to (6)

| Examples | com-pound No. | Blue toner No. | Part. size | | Chargeability | | | |
|---|---|---|---|---|---|---|---|---|
| | | | | | Normal | | High | |
| | | | Ave. part. size (μm) | Fine powder amount (number %) | temp/normal humidity | | temp/high humidity | |
| | | | | | 10 sec agit. | 300 sec agit. | 10 sec. agit. | 300 sec agit. |
| 15 | 1 | 1 | 7.2 | 5.1 | ⊚ | ⊚ | ⊚ | ⊚ |
| 16 | 2 | 2 | 7.0 | 5.0 | ⊚ | ⊚ | ○ | ⊚ |
| 17 | 3 | 3 | 7.3 | 5.0 | ○ | ⊚ | ○ | ⊚ |
| 18 | 4 | 4 | 7.1 | 5.3 | ○ | ⊚ | ○ | ⊚ |
| 19 | 5 | 5 | 7.0 | 5.4 | ⊚ | ⊚ | ○ | ⊚ |
| 20 | 6 | 6 | 6.9 | 5.5 | ○ | ⊚ | ○ | ⊚ |
| Com. ex. 1 | — | 7 | 7.0 | 5.2 | X | X | X | X |

Examples 21 to 26

Yellow toners (1) to (6) of the examples 21 to 26 were obtained by a method similar to that in the example 15 except that the example compounds (1) to (6) were respectively used in 2.0 mass parts and the cyan coloring agent was replaced by yellow coloring agent (Hanza yellow G). The characteristics of these toners were measured as in the example 15, and the results are shown in Table 9. Also these toners were used as in the example 15 to respectively obtain two-component yellow developers (1) to (6).

Comparative Example 2

Yellow toner 7 of the comparative example 2 was obtained by a method similar to that of the example 15, except that the example compound was not used and that the cyan coloring agent was replaced by the yellow coloring agent (Hanza yellow G). The characteristics of such toner were measured as in the example 15, and the results are shown in Table 9. Also such toner was used as in the example 15 to obtain two-component yellow developer 7 of the comparative example 2.

<Evaluation>

The two-component yellow developers (1) to (6) obtained in the examples 21 to 26 and the two-component yellow developer 7 obtained in the comparative example 2 were subjected to the measurement of toner charge amount after agitation for 10 or 300 seconds, by the aforementioned charge amount measuring method, respectively under an environment of normal temperature and normal humidity (25° C., 60% RH) and an environment of high temperature and high humidity (30° C., 80% RH). The measured value of the two-component blow-off charge amount was rounded at the second place under fractional point, and was evaluated by the following criteria. The results are summarized in Table 9:

⊚: very satisfactory (not exceeding −20 μC/g);
○: satisfactory (−19.9 to −10.0 μC/g);
Δ: practically acceptable (−9.9 to −5.0 μC/g);
X: practically unacceptable (−4.9 μC/g or higher).

TABLE 9

Charging characteristics of yellow toners (1) to (6)

| Examples | com-pound No. | yellow toner No. | Part. size | | Chargeability | | | |
|---|---|---|---|---|---|---|---|---|
| | | | | Distribution | Normal | | High | |
| | | | Ave. part. size (μm) | Fine powder amount (number %) | temp/normal humidity | | temp/high humidity | |
| | | | | | 10 sec agit. | 300 sec agit. | 10 sec. agit. | 300 sec agit. |
| 21 | 1 | 1 | 7.1 | 5.5 | ⊚ | ⊚ | ⊚ | ⊚ |
| 22 | 2 | 2 | 7.3 | 5.6 | ⊚ | ⊚ | ⊚ | ⊚ |
| 23 | 3 | 3 | 7.2 | 5.4 | ⊚ | ⊚ | ○ | ⊚ |
| 24 | 4 | 4 | 7.0 | 5.5 | ○ | ⊚ | ○ | ⊚ |
| 25 | 5 | 5 | 7.1 | 5.2 | ⊚ | ⊚ | ○ | ⊚ |
| 26 | 6 | 6 | 7.1 | 5.1 | ⊚ | ⊚ | ○ | ⊚ |
| Com. ex. 2 | — | 7 | 7.2 | 4.9 | X | X | X | X |

Examples 27 to 32

Black toners (1) to (6) of the examples 27 to 32 were obtained by a method similar to that in the example 15 except that the example compounds (1) to (6) were respectively used in 2.0 mass parts and the cyan coloring agent was replaced by carbon black (DBP oil absorption amount 110 ml/100 g). The characteristics of these toners were measured as in the example 15, and the results are shown in Table 10. Also these toners were used as in the example 15 to respectively obtain two-component black developers (1) to (6).

Comparative Example 3

Black toner 7 of the comparative example 3 was obtained by a method similar to that of the example 15, except that the example compound was not used and that the cyan coloring agent was replaced by carbon black (DBP oil absorption amount 110 ml/100 g). The characteristics of such toner were measured as in the example 15, and the results are shown in Table 10. Also such toner was used as in the example 15 to obtain two-component black developer 7 of the comparative example 3.

<Evaluation>

The two-component black developers (1) to (6) obtained in the examples 27 to 32 and the two-component black developer 7 obtained in the comparative example 2 were subjected to the measurement of toner charge amount after agitation for 10 or 300 seconds, by the aforementioned charge amount measuring method, respectively under an environment of normal temperature and normal humidity (25° C., 60% RH) and an environment of high temperature and high humidity (30° C., 80% RH). The measured value of the two-component blow-off charge amount was rounded at the second place under fractional point, and was evaluated by the following criteria. The results are summarized in Table 10:

⊚: very satisfactory (not exceeding −20 μC/g);
O: satisfactory (−19.9 to −10.0 μC/g);
Δ: practically acceptable (−9.9 to −5.0 μC/g);
X: practically unacceptable (−4.9 μC/g or higher).

TABLE 10

Charging characteristics of black toners (1) to (6)

| | | | Part. Size | | Chargeability | | |
| | | | | | Normal | | High |
| | | | Distribution | | | | |
| Examples | Ex. com- pound No. | black toner No. | Ave. part. size (μm) | Fine powder amount (num- ber. %) | temp/normal humidity | | temp/high humidity | |
| | | | | | 10 sec agit. | 300 sec agit. | 10 sec. agit. | 300 sec agit. |
| 27 | 1 | 1 | 6.9 | 5.1 | ⊚ | ⊚ | ⊚ | ⊚ |
| 28 | 2 | 2 | 7.3 | 5.4 | ⊚ | ⊚ | ⊚ | ⊚ |
| 29 | 3 | 3 | 7.0 | 5.5 | O | ⊚ | O | ⊚ |
| 30 | 4 | 4 | 7.4 | 6.1 | O | ⊚ | O | ⊚ |
| 31 | 5 | 5 | 7.1 | 5.6 | O | ⊚ | O | ⊚ |
| 32 | 6 | 6 | 7.0 | 5.2 | O | ⊚ | O | ⊚ |
| Com. ex. 3 | — | 7 | 6.9 | 5.3 | X | Δ | X | Δ |

Example 33

Following Composition

| | |
|---|---|
| styrene-butyl acrylate copolymer resin (glass transition point 70° C.) | 100 mass parts |
| magenta pigment (C.I. pigment red 114) | 5 mass parts |
| example compound (1) | 2 mass parts | was mixed, and fused and kneaded in a twin-screw extruder (L/D=30). The kneaded substance after cooling was roughly pulverized with a hammer mill, then finely pulverized with a jet mill and classified to obtain magenta colored particles (1) of pulverizing method, which had a weight-averaged particle size of 7.3 μm and a fine powder amount of 5.0 number %.

100 mass parts of thus prepared magenta colored particles (1) were externally added, by dry mixing with a Henshell mixer, with 1.5 mass parts of hydrophobic silica powder (BET: 250 m²/g) treated with hexamethyl disilazane as the flowability improving agent, to obtain magenta toner (1) of the present example. Further, 7 pass parts of the magenta toner (1) and 93 mass parts of resin-coated magnetic ferrite carrier (average particle size 45 μm) to obtain two-component magenta developer (1) for magnetic brush development.

Examples 34 to 38

Magenta toners (2) to (6) of the examples 34 to 38 were obtained by a method similar to that in the example 33 except that the example compound (1) was respectively replaced by example compounds (2) to (6). The characteristics of these toners were measured as in the example 15, and the results are shown in Table 11. Also these toners were used as in the example 33 to respectively obtain two-component magenta developers (2) to (6).

Comparative Example 4

Magenta toner 7 of the comparative example 4 was obtained by a method similar to that of the example 33, except that the example compound was not used. The characteristics of such toner were measured as in the example 15, and the results are shown in Table 11. Also such toner was used as in the example 33 to obtain two-component magenta developer 7.

<Evaluation>

The two-component magenta developers (1) to (6) obtained in the examples 33 to 38 and the two-component magenta developer 7 obtained in the comparative example 4 were subjected to the measurement of toner charge amount after agitation for 10 or 300 seconds, by the aforementioned charge amount measuring method, respectively under an environment of normal temperature and normal humidity (25° C., 60% RH) and an environment of high temperature and high humidity (30° C., 80% RH). The measured value of the two-component blow-off charge amount was rounded at the second place under fractional point, and was evaluated by the following criteria. The results are summarized in Table 11:

⊚: very satisfactory (not exceeding −20 μC/g);
O: satisfactory (−19.9 to −10.0 μC/g);
Δ: practically acceptable (−9.9 to −5.0 μC/g);
X: practically unacceptable (−4.9 μC/g or higher).

TABLE 11

Charging characteristics of magenta toners (1) to (6)

| | | | Part. size | | Chargeability | | |
| | | | | | Normal | | High |
| | | | Distribution | | | | |
| Examples | Ex. com- pound No. | magenta toner No. | Ave. part. size (μm) | Fine powder amount (num- ber. %) | temp/normal humidity | | temp/high humidity | |
| | | | | | 10 sec agit. | 300 sec agit. | 10 sec. agit. | 300 sec agit. |
| 33 | 1 | 1 | 7.3 | 5.0 | ⊚ | ⊚ | ⊚ | ⊚ |
| 34 | 2 | 2 | 7.1 | 5.2 | ⊚ | ⊚ | ⊚ | ⊚ |
| 35 | 3 | 3 | 7.0 | 5.5 | ⊚ | ⊚ | O | ⊚ |
| 36 | 4 | 4 | 6.9 | 5.0 | ⊚ | ⊚ | O | ⊚ |
| 37 | 5 | 5 | 6.9 | 5.3 | O | ⊚ | O | ⊚ |
| 38 | 6 | 6 | 7.2 | 5.0 | O | ⊚ | O | ⊚ |
| Com. ex. 4 | — | 7 | 7.1 | 5.1 | X | X | X | X |

Examples 39 to 44

Black toners (8) to (13) of the examples 39 to 44 were obtained by a method similar to that in the example 33 except that the example compounds (1) to (6) were respectively used in 2.0 mass parts and the magenta pigment was replaced by carbon black (DBP oil absorption amount 110 ml/100 g). The characteristics of these toners were measured as in the example 15, and the results are shown in Table 12. Also these toners were used as in the example 33 to respectively obtain two-component black developers (8) to (13).

Comparative Example 5

Black toner 14 of the comparative example 5 was obtained by a method similar to that of the example 33, except that the example compound was not used and that the magenta pigment was replaced by carbon black (DBP oil absorption amount 110 ml/100 g). The characteristics of such toner were measured as in the example 15, and the results are shown in Table 12. Also such toner was used as in the example 33 to obtain two-component black developer 14 of the comparative example 5.

<Evaluation>

The two-component black developers (8) to (13) obtained in the examples 39 to 44 and the two-component black developer 14 obtained in the comparative example 5 were subjected to the measurement of toner charge amount after agitation for 10 or 300 seconds, by the aforementioned charge amount measuring method, respectively under an environment of normal temperature and normal humidity (25° C., 60% RH) and an environment of high temperature and high humidity (30° C., 80% RH). The measured value of the two-component blow-off charge amount was rounded at the second place under fractional point, and was evaluated by the following criteria. The results are summarized in Table 12:

⊚: very satisfactory (not exceeding −20 µC/g);
○: satisfactory (−19.9 to −10.0 µC/g);
Δ: practically acceptable (−9.9 to −5.0 µC/g);
X: practically unacceptable (−4.9 µC/g or higher).

TABLE 12

Charging characteristics of black toners (8) to (13)

| | | | Part. size | | Chargeability | | | |
| | | | | | Normal | | High | |
| | | | | Distribution | | | | |
| | | | | Fine | temp/normal humidity | | temp/high humidity | |
| Examples | Ex. com- pound No. | black toner No. | Ave. part. size (µm) | powder amount (num- ber. %) | 10 sec agit. | 300 sec agit. | 10 sec. agit. | 300 sec agit. |
| 39 | 1 | 8 | 6.9 | 5.2 | ⊚ | ⊚ | ⊚ | ⊚ |
| 40 | 2 | 9 | 7.0 | 5.0 | ⊚ | ⊚ | ⊚ | ⊚ |
| 41 | 3 | 10 | 7.3 | 5.2 | ○ | ⊚ | ○ | ⊚ |
| 42 | 4 | 11 | 7.2 | 5.3 | ○ | ⊚ | ○ | ⊚ |
| 43 | 5 | 12 | 6.9 | 5.5 | ○ | ⊚ | ○ | ⊚ |
| 44 | 6 | 13 | 7.2 | 5.5 | ○ | ⊚ | ○ | ⊚ |
| Com. ex. 5 | — | 14 | 7.0 | 5.7 | X | Δ | X | X |

Example 45

| polyester resin | 100 mass parts |
| carbon black (DBP oil absorption amount 110 ml/100 g) | 5 mass parts |
| example compound (1) | 2 mass parts |

Polyester resin was synthesized in the following manner. 751 parts of bisphenol-A propylene oxide 2-mole addition product, 104 parts of terephthalic acid and 167 parts of trimellitic anhydride were condensation polymerized utilizing 2 parts of dibutyltin oxide to obtain polyester resin of a softening point of 125° C. The above-mentioned composition was mixed, and fused and kneaded in a twin-screw extruder (L/D=30). The kneaded substance after cooling was roughly pulverized with a hammer mill, then finely pulverized with a jet mill and classified to obtain black colored particles (15) of pulverizing method, which had a weight-averaged particle size of 7.4 µm and a fine powder amount of 5.1 number %.

100 mass parts of thus prepared black polymer particles (15) were externally added, by dry mixing with a Henshell mixer, with 1.5 mass parts of hydrophobic silica powder (BET: 250 m²/g) treated with hexamethyl disilazane as the flowability improving agent, to obtain black toner (15) of the present example. Further, 7 pass parts of the black toner (15) and 93 mass parts of resin-coated magnetic ferrite carrier (average particle size 45 µm) to obtain two-component black developer (15) for magnetic brush development.

Examples 46 to 50

Black toners (16) to (20) of the examples 46' to 50 were obtained by a method similar to that in the example 45 except that the example compound (1) was respectively replaced by example compounds (2) to (6). The characteristics of these toners were measured as in the example 15, and the results are shown in Table 13. Also these toners were used as in the example 45 to respectively obtain two-component black developers (16) to (20).

Comparative Example 6

Black toner 21 of the comparative example 6 was obtained by a method similar to that of the example 45, except that the example compound was not used. The characteristics of such toner were measured as in the example 15, and the results are shown in Table 12. Also such toner was used as in the example 45 to obtain two-component black developer 21.

<Evaluation>

The two-component black developers (15) to (20) obtained in the examples 45 to 50 and the two-component black developer 21 obtained in the comparative example 6 were subjected to the measurement of toner charge amount after agitation for 10 or 300 seconds, by the aforementioned charge amount measuring method, respectively under an environment of normal temperature and normal humidity (25° C., 60% RH) and an environment of high temperature and high humidity (30° C., 80% RH). The measured value of the two-component blow-off charge amount was rounded at the second place under fractional point, and was evaluated by the following criteria. The results are summarized in Table 13:

⊚: very satisfactory (not exceeding −20 µC/g);
○: satisfactory (−19.9 to −10.0 µC/g);
Δ: practically acceptable (−9.9 to −5.0 µC/g);
X: practically unacceptable (−4.9 µC/g or higher).

TABLE 13

Charging characteristics of black toners (15) to (20)

| | | | Part. size | | Chargeability | | | |
| | | | | | Normal | | High | |
| | | | | distribution | | | | |
| | | | | Fine | temp/normal humidity | | temp/high humidity | |
| Examples | Ex. com- pound No. | black toner No. | Ave. part. size (µm) | powder amount (num- ber. %) | 10 sec agit. | 300 sec agit. | 10 sec. agit. | 300 sec agit. |
| 45 | 1 | 15 | 7.4 | 5.1 | ⊚ | ⊚ | ⊚ | ⊚ |
| 46 | 2 | 16 | 7.7 | 5.0 | ⊚ | ⊚ | ⊚ | ⊚ |
| 47 | 3 | 17 | 7.3 | 5.2 | ⊚ | ⊚ | ⊚ | ⊚ |
| 48 | 4 | 18 | 7.5 | 5.3 | ○ | ⊚ | ○ | ⊚ |
| 49 | 5 | 19 | 7.7 | 5.1 | ⊚ | ⊚ | ○ | ⊚ |

TABLE 13-continued

Charging characteristics of black toners (15) to (20)

| | | | Part. size distribution | | Chargeability | | | |
| | | | | | Normal | | High | |
| | | | | | temp/normal humidity | | temp/high humidity | |
| Examples | Ex. com- pound No. | black toner No. | Ave. part. size (μm) | Fine powder amount (num- ber. %) | 10 sec agit. | 300 sec agit. | 10 sec. agit. | 300 sec agit. |
|---|---|---|---|---|---|---|---|---|
| 50 | 6 | 20 | 7.2 | 5.0 | ○ | ◎ | ○ | ◎ |
| Com. ex. 6 | — | 21 | 7.5 | 4.9 | X | Δ | X | Δ |

Examples 51 to 66 and Comparative Examples 7 to 12

At first there will be explained an image forming apparatus employed in the image forming method of the examples 51 to 66 and the comparative examples 7 to 12. FIG. 1 is a schematic cross-sectional view of an image forming apparatus for executing the image forming method of the examples of the present invention and the comparative examples. Referring to FIG. 1, a photosensitive drum 1 is provided with a photosensitive layer 1a containing organic photosemiconductor on a substrate 1b, is rendered rotatable in the direction of arrow, and is surfacially charged at a surface potential of about −600 V by a charging roller 2 constituting a charging member opposed to the photosensitive drum 1 and rotated by contact therewith. As shown in FIG. 1, the charging roller 2 is composed of a conductive elastic layer 2a provided on a core metal 2b.

Figure 2:
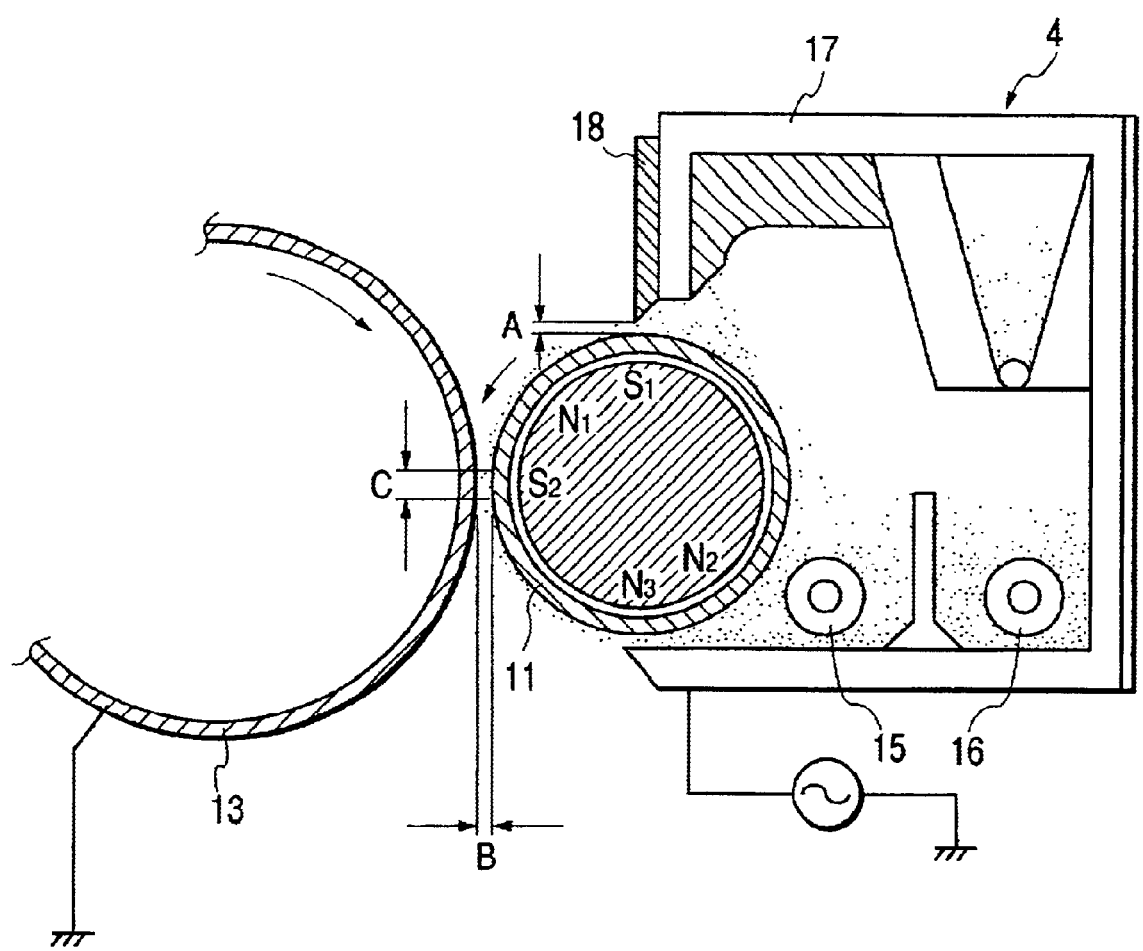
FIG. 2 is a partial magnified cross-sectional view of each developing apparatus 4 for two-component developer shown in FIG. 1.

Then exposure 3 is made toward the surfacially charged photosensitive drum 1 in on-off mode according to the digital image information by a polygon mirror to form an electrostatic latent image of an exposed potential of −100 V and a dark potential of −600 v. Then the electrostatic latent image on the photosensitive drum 1 is reversal developed and rendered visible with plural developing devices 4-1, 4-2, 4-3, 4-4 to form a toner image on the photosensitive drum 1. In this operation, there were respectively employed the two-component developers obtained in the examples 15 to 20, 21, 24, 27, 30, 33, 36, 39, 42, 45, 48 and comparative examples 1 to 6 to form toner images with yellow, magenta, cyan or black toner. FIG. 2 is a magnified partial cross-sectional view of each developing device 4 for two-component developer, employed in the development. Then the toner image on the photosensitive drum 1 is transferred onto an intermediate transfer member 5 rotated in contact with the photosensitive drum 1. As a result, superposed visible images of four colors are formed on the intermediate transfer member 5. The remaining toner, not transferred and remaining on the photosensitive drum 1, is recovered by a cleaner member 8 into a remaining toner container 9.

As shown in FIG. 1, the intermediate transfer member 5 is composed of a metal core 5b constituting a support member, and an elastic layer 5a laminated thereon. In the present example, there was employed an intermediate transfer member 5 formed by coating a pipe-shaped core metal 5b with an elastic layer 5b composed of carbon black as conductivity providing material sufficiently dispersed in nitrile-butadiene rubber (NBR). The elastic layer 5b had a hardness of 30 degrees measured according to JIS K 6301, and a volume resistivity of $10^9$ Ωcm. The transfer current required for transfer from the photosensitive drum 1 to the intermediate transfer member 5 was about 5 μA and was obtained by providing the core metal 5b with a voltage of +500 V from a power source.

The superposed toner images of four colors formed on the intermediate transfer member 5 were transferred by a transfer roller 7 to a transfer material such as paper, and then fixed by a heat fixing device H. The transfer roller 7 was formed by coating, on a core metal 7b of an external diameter of 10 mm, an elastic layer 7a composed of carbon as conductivity providing material sufficiently dispersed in the foam of ethylene-propylene-diene three-dimensional foamed copolymer (EPDM). It had a volume resistivity of $10^6$ Ωcm and a hardness of 35 degrees measured according to JIS K 6301. The transfer roller 7 was given a voltage to obtain a transfer current of 15 μA.

Figure 5:
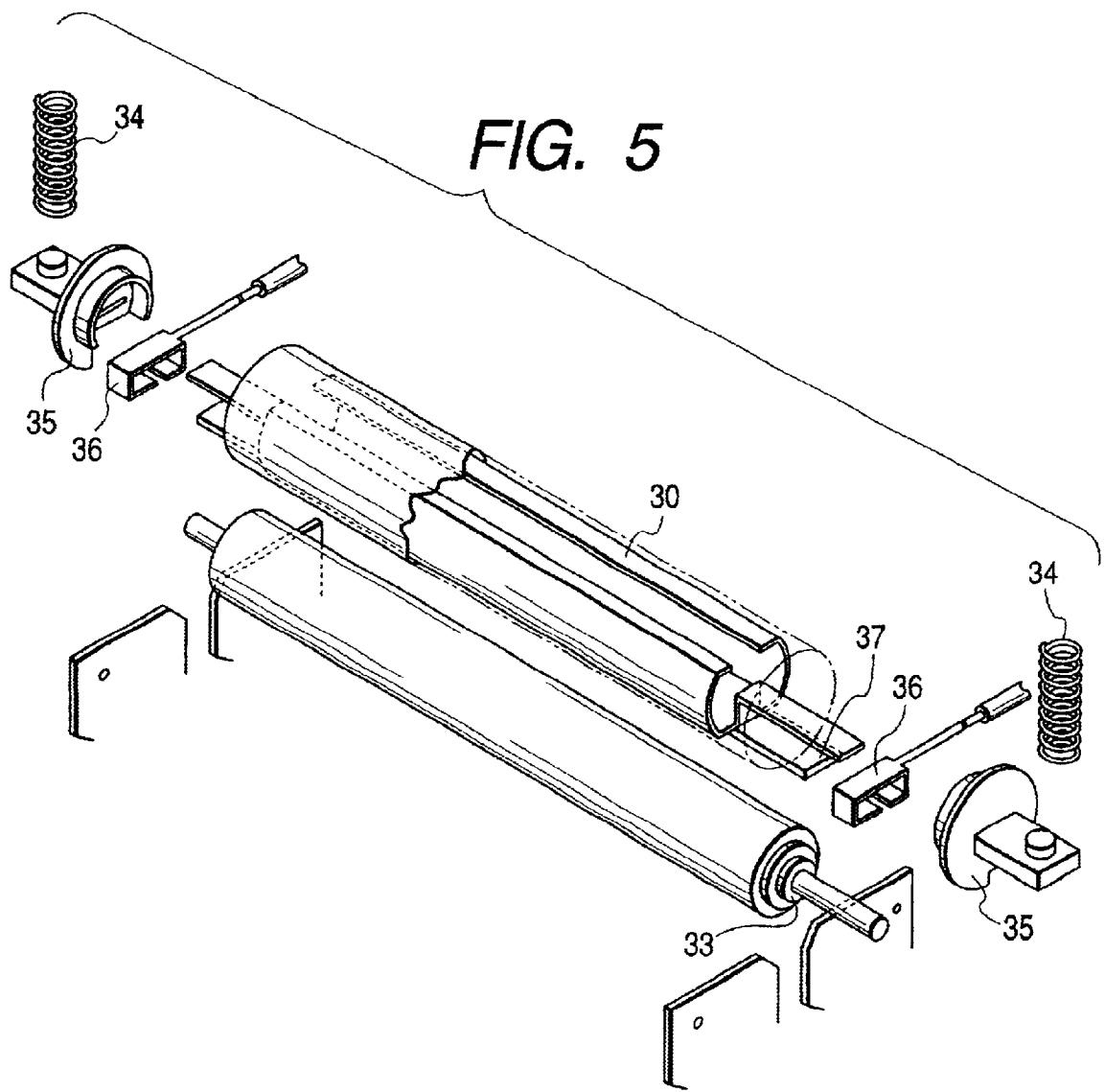
FIG. 5 is a partial exploded perspective view of a fixing apparatus employed in the examples of the present invention.
Figure 6:
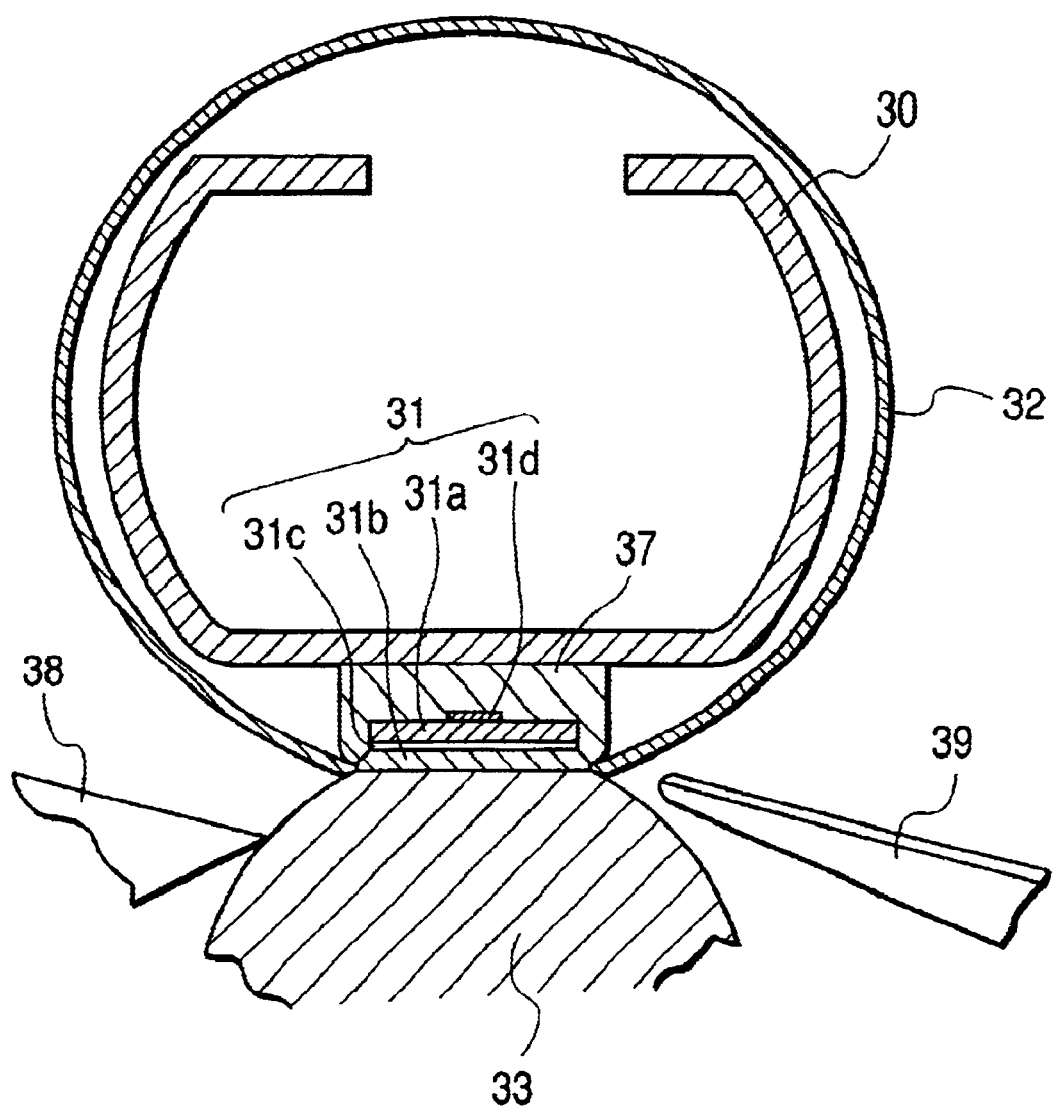
FIG. 6 is a partial magnified cross-sectional view of a fixing apparatus employed in the examples of the present invention, showing a film state in a non-driven state.

In the apparatus shown in FIG. 1, the heat fixing device H was of heated roller type without oil coating mechanism as shown in FIGS. 5 and 6. Both the upper and lower rollers were provided with surface layers of fluorinated resin. The rollers had a diameter of 60 mm. The fixing temperature was selected as 160° C., and the nip width was selected as 7 mm. The toner remaining on the photosensitive drum 1 recovered by cleaning was conveyed by a reuse mechanism to the developing device and was reused.

<Evaluation>

Printout test was conducted with the above-described configuration, under the environments of normal temperature and normal humidity (25° C., 60% RH) and high temperature and high humidity (30° C., 80% RH) and at a printout speed of 8 (A4 size) sheet/minute, respectively utilizing the two-component developers prepared with the toners of examples 15 to 20, 21, 24, 27, 30, 33, 36, 39, 42, 45, 48 and those prepared with the toners of comparative examples 1~6 under successive replenishment, in a monocolor intermittent mode (developing device being stopped for 10 seconds after each printout to accelerate the deterioration of the toner by the preparatory operation at the re-start), and the obtained printout image was evaluated for the following items. The results of evaluation are summarized in Table 14.

[Printout Image Evaluation]

1. Image Density

Printouts of a predetermined number were made on ordinary copying plain paper (75 g/m²), and there was evaluated the level of image density maintained in the image at the end of printing with respect to the initial image. The image density was measured with a Macbeth reflective densitometer (supplied by Macbeth Inc.), and the evaluation was made on the relative density of the printout image corresponding to a white portion of the original having a density of 0.00 by the following criteria:

◎: excellent (image density at end at least equal to 1.4)

○: good (image density at end at least equal to 1.35 but less than 1.40)

Δ: fair (image density at end at least equal to 1.00 but less than 1.35)

X: poor (image density at end less than 1.00).

2. Image Fogging

Printouts of a predetermined number were made on ordinary copying plain paper (75 g/m²), and the evaluation was made by a solid white image at the end of the printouts. More specifically, the worst reflective density Ds of the white portion after printout, measured with a reflective densitometer (Reflectometer Model TC-6DS supplied by Tokyo Denshoku Co., Ltd.) and the average reflective density Dr of the sheet before printing were used to calculate (Ds−Dr) as the fog amount, which was evaluated according to the following criteria:

⊚: excellent (fog amount at least equal to 0% but less than 1.5%)

○: good (fog amount at least equal to 1.5% but less than 3.0%)

Δ: fair (fog amount at least equal to 3.0% but less than 5.0%)

X: poor (fog amount at least equal to 5.0%)

3. Transfer Ability

A solid-black image was printed for a predetermined number on ordinary copying plain paper (75 g/m$^2$), and the amount of image blank amount at the end of printouts was observed visually and evaluated according to the following criteria:

⊚: excellent (almost none)

○: good (slight)

Δ: practically acceptable

X: practically unacceptable

Also after image outputs of 5000 sheets in the examples 51 to 66 and comparative examples 7 to 12, the surfacial scars on the photosensitive drum and the intermediate transfer member, generation of fixing of the remaining toner and influence on the printout image (matching with image forming apparatus) were visually inspected. In the systems utilizing the two-component developers of the examples 51 to 66, the surfacial scars on the photosensitive drum and the intermediate transfer member and generation of fixing of the remaining toner were not at all observed, and the matching with image forming apparatus was very satisfactory. On the other hand, in the systems utilizing the two-component developers of the comparative examples 7 to 12, there was observed the fixing of the remaining toner was observed. Also in the systems utilizing the two-component developers of the comparative examples 7 to 12, there were observed the fixing of the remaining toner and the surfacial scars on the intermediate transfer member, and the matching with image forming apparatus was unsatisfactory in that the image showed defects such as vertical streaks.

TABLE 14 evaluation results of printout image

| | | normal temp. normal hum. | | | high temp. high humidity | | |
|---|---|---|---|---|---|---|---|
| Ex. | 2-com. developer | image density | image fogging | trans-fer abil-ity | image density | image fogging | transfer ability |
| 51 | blue 1 | ⊚ | ⊚ | ⊚ | ⊚ | ⊚ | ⊚ |
| 52 | blue 2 | ⊚ | ⊚ | ⊚ | ○ | ⊚ | ⊚ |
| 53 | blue 3 | ⊚ | ⊚ | ⊚ | ○ | ○ | ⊚ |
| 54 | blue 4 | ⊚ | ⊚ | ⊚ | ○ | ⊚ | ○ |
| 55 | blue 5 | ⊚ | ⊚ | ⊚ | ○ | ○ | ○ |
| 56 | blue 6 | ⊚ | ⊚ | ⊚ | ○ | ○ | ○ |
| 57 | yellow 1 | ⊚ | ⊚ | ⊚ | ⊚ | ⊚ | ⊚ |
| 58 | yellow 4 | ⊚ | ⊚ | ⊚ | ○ | ⊚ | ⊚ |
| 59 | black 1 | ⊚ | ⊚ | ⊚ | ⊚ | ⊚ | ⊚ |
| 60 | black 4 | ⊚ | ⊚ | ⊚ | ⊚ | ⊚ | ⊚ |
| 61 | red 1 | ⊚ | ⊚ | ⊚ | ⊚ | ⊚ | ⊚ |
| 62 | red 4 | ⊚ | ⊚ | ⊚ | ⊚ | ⊚ | ⊚ |
| 63 | black 8 | ⊚ | ⊚ | ⊚ | ⊚ | ⊚ | ⊚ |
| 64 | black 11 | ⊚ | ⊚ | ⊚ | ○ | ⊚ | ⊚ |
| 65 | black 15 | ⊚ | ⊚ | ⊚ | ⊚ | ⊚ | ⊚ |
| 66 | black 18 | ⊚ | ⊚ | ⊚ | ○ | ⊚ | ⊚ |

TABLE 14-continued evaluation results of printout image

| | | normal temp. normal hum. | | | high temp. high humidity | | |
|---|---|---|---|---|---|---|---|
| Ex. | 2-com. developer | image density | image fogging | trans-fer abil-ity | image density | image fogging | transfer ability |
| Com ex 7 | blue 7 | X | X | X | X | X | X |
| 8 | yellow 7 | X | X | X | X | X | X |
| 9 | black 7 | Δ | Δ | X | Δ | X | X |
| 10 | red 7 | Δ | Δ | X | Δ | X | X |
| 11 | black 14 | Δ | Δ | X | X | X | X |
| 12 | black 21 | Δ | Δ | X | Δ | X | X |

Examples 67 to 69 and Comparative Examples 13 to 15

Figure 3:
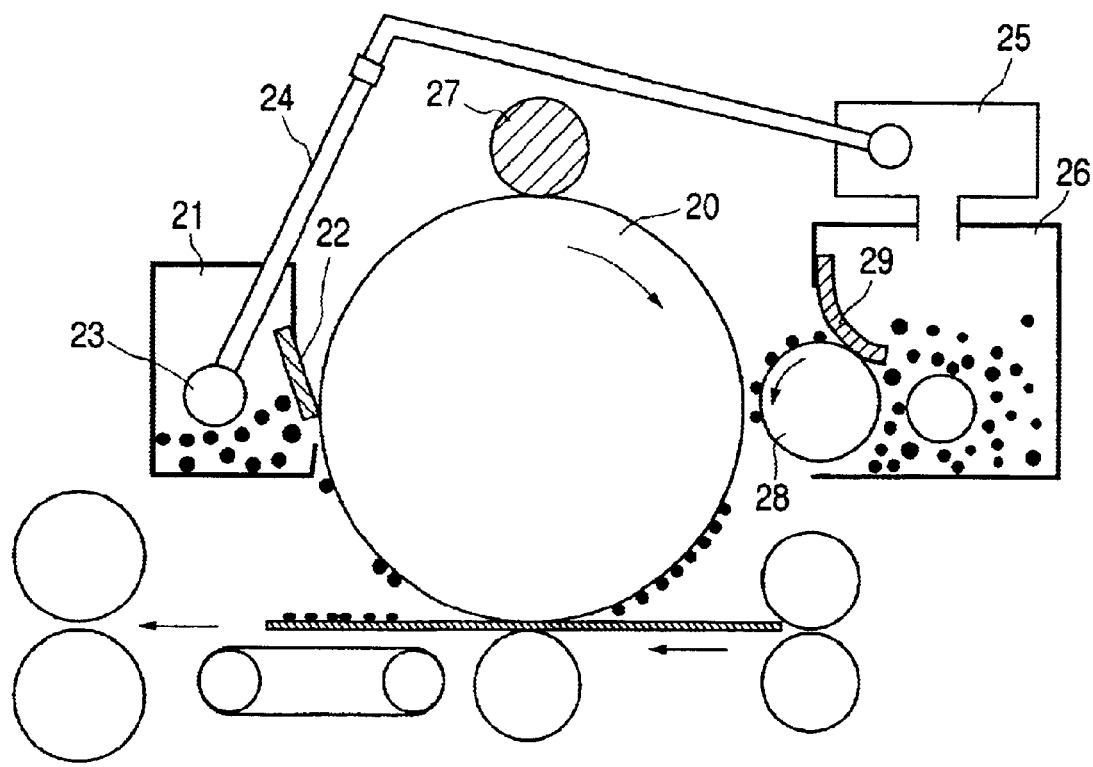
FIG. 3 is a schematic view of an image forming apparatus including a toner reuse mechanism, employed in the examples and comparative examples of the present invention.

In the execution of the image forming method of the examples 67 to 69 and the comparative examples 13 to 15, there were respectively employed toners obtained in the examples 15, 21, 27 and the comparative examples 1 to 3 as the developer. Also as image forming means, there was employed an image forming apparatus obtained by modifying and resetting a commercially available laser beam printer LBP-EX (Canon Inc.) by mounting a reuse mechanism as shown in FIG. 3. More specifically, in the image forming apparatus shown in FIG. 3, there is provided a system for reusing the recovered toner, in which the untransferred toner remaining on the photosensitive drum 20 after the transfer is scraped off by an elastic blade 22 of a cleaner 21 maintained in contact with the photosensitive drum 20, then fed into the cleaner 21 by a cleaner roller, further conveyed by a cleaner reuse mechanism 23 and returned by a supply pipe 24 having a feed screw to a developing device 26 through a hopper 25.

In the image forming apparatus shown in FIG. 3, the photosensitive drum 20 is surfacially charged by a primary charging roller 27. The primary charging roller 27 was composed a rubber roller (diameter 12 mm, contact pressure 50 g/cm) containing conductive carbon dispersed therein and covered with nylon resin. By laser exposure (600 dpi, not shown), an electrostatic latent image with a dark potential VD=−700 V and a light potential VL=−200 V was formed on the electrostatic latent image bearing member (photosensitive drum 20). The toner bearing member was composed of a developing sleeve 28 having a surface roughness Ra of 1.1 and surfacially coated with resin containing carbon black dispersed therein.

Figure 4:
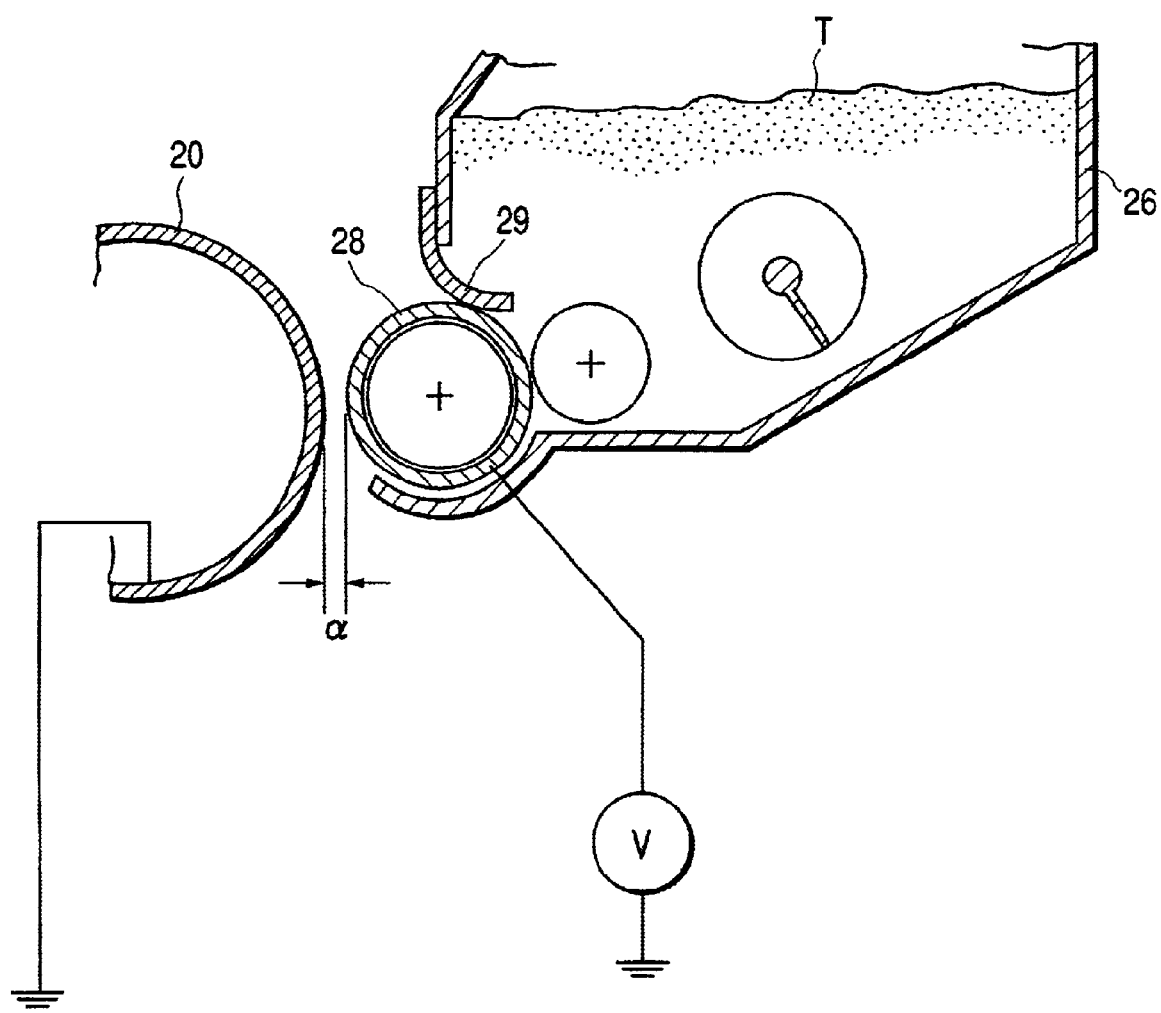
FIG. 4 is a partial cross-sectional view of a developing apparatus for one-component developer employed in the examples and comparative examples of the present invention.

FIG. 4 is a partial magnified cross-sectional view of a developing device for one-component developer, employed in the examples 59 to 61 and the comparative examples 13 to 15. As the developing conditions for the electrostatic latent image, the speed of the developing sleeve 28 was selected as 1.1 times of the surface moving speed of the opposed photosensitive drum 20, and the gap α (S−D) between the photosensitive drum 20 and the developing sleeve 28 was selected as 270 μm. For regulating the toner layer thickness, an urethane rubber blade 29 was employed in contact state. Also the heat fixing device for fixing the toner image was set at a temperature of 160° C. The employed fixing device was as shown in FIGS. 5 and 6.

Printout test was conducted up to 30,000 prints with the above-described configuration, under the environments of normal temperature and normal humidity (25° C., 60% RH), at a printout speed of 8 (A4 size) sheet/minute and under successive toner replenishment, in a continuous mode (developing device being operated without stopping to accelerate the consumption of the toner), and the image density was measured on the obtained printout image and the durability of the image density was evaluated by the following criteria. Also the image of the 10,000th print was observed and the image fogging was evaluated by the following criteria. Also, observation was made on the state of the components constituting the image forming apparatus after the durability test, and evaluation was made also on the matching between each component and each toner. The results of evaluation are summarized in Table 15.

[Image Density Change in Durability Test]

Printouts of a predetermined number were made on ordinary copying plain paper (75 g/m$^2$), and there was evaluated the level of image density maintained in the image at the end of printing with respect to the initial image. The image density was measured with a Macbeth reflective densitometer (supplied by Macbeth Inc.), and the evaluation was made on the relative density of the printout image corresponding to a white portion of the original having a density of 0.00 by the following criteria:

⊚: excellent (image density at end at least equal to 1.4)

○: good (image density at end at least equal to 1.35 but less than 1.40)

Δ: fair (image density at end at least equal to 1.00 but less than 1.35)

X: poor (image density at end less than 1.00).

2. Image Fogging

Printouts of a predetermined number were made on ordinary copying plain paper (75 g/m$^2$), and the evaluation was made by a solid white image at the end of the printouts. More specifically, the worst reflective density Ds of the white portion after printout, measured with a reflective densitometer (Reflectometer Model TC-6DS supplied by Tokyo Denshoku Co., Ltd.) and the average reflective density Dr of the sheet before printing were used to calculate (Ds−Dr) as the fog amount, which was evaluated according to the following criteria:

⊚: excellent (fog amount at least equal to 0% but less than 1.5%)

○: good (fog amount at least equal to 1.5% but less than 3.0%)

Δ: fair (fog amount at least equal to 3.0% but less than 5.0%)

X: poor (fog amount at least equal to 5.0%)

[Evaluation of Matching with Image Forming Apparatus]

1. Matching With Developing Sleeve

After the printout test, the state of fixation of the remaining toner to the developing sleeve surface and the influence thereof on the printout image were evaluated visually:

⊚: excellent (none)

○: good (almost none)

Δ: practically acceptable (toner fixation present but little influence on the image)

X: practically unacceptable (toner fixation present in a large amount to cause unevenness in the image).

2. Matching with Photosensitive Drum

The scars on the photosensitive drum surface, the state of fixation of the remaining toner thereto and the influence thereof on the printout image were evaluated visually:

⊚: excellent (none)

○: good (slight scar generated but no influence on the image)

Δ: practically acceptable (toner fixation and scars present but little influence on the image)

X: practically unacceptable (toner fixation present in a large amount to cause image defects in streaks).

3. Matching with Fixing Device

The state of the surface of the fixing film was observed, and the durability thereof was evaluated in consideration of the surface state and the fixation of the remaining toner.

(1) Surface State

After the printout test, scars and peeling on the surface of the fixing film were visually observed and evaluated:

⊚: excellent (none)

○: good (almost none)

Δ: practically acceptable

X: practically unacceptable.

(2) Fixation of Remaining Toner

After the printout test, the state of fixation of the remaining toner on the surface of the fixing film was visually observed and evaluated:

⊚: excellent (none)

○: good (almost none)

Δ: practically acceptable

X: practically unacceptable.

TABLE 15

Result of printout image evaluation and matching with image forming apparatus

| | | Printout image evaluation | | | | | Matching | | |
| | | Image density change in Durability test | | | | Image fogging | Developing sleeve | Photo-sensitive drum | Fix-device | |
| Example | Toner | Initial | 1,000 | 10,000 | 30,000 | 10,000 | | | Surface | Toner fix. |
|---|---|---|---|---|---|---|---|---|---|---|
| 67 | blue 1 | ⊚ | ⊚ | ⊚ | ⊚ | ⊚ | ⊚ | ⊚ | ⊚ | ⊚ |
| 68 | yellow 1 | ⊚ | ⊚ | ⊚ | ⊚ | ⊚ | ⊚ | ⊚ | ⊚ | ⊚ |
| 69 | black 1 | ⊚ | ⊚ | ⊚ | ⊚ | ⊚ | ⊚ | ⊚ | ⊚ | ⊚ |
| Com. ex 13 | yellow 7 | Δ | X | X | X | X | X | X | X | X |
| 14 | yellow 7 | Δ | X | X | X | X | X | X | X | X |
| 15 | black 7 | ○ | Δ | X | X | X | X | X | X | X |

Printout test was executed in the same manner as in the example 67, except that the toner reuse device was detached from the image forming apparatus shown in FIG. 3 and the printout speed was changed to 16 (A4 size) sheet/minute, under successive replenishment of the blue toner (1) of the example 15, in a continuous mode (developing device being operated without stopping to accelerate the consumption of the toner). The obtained printout image and the matching with the image forming apparatus were evaluated on the items same as those in the examples 67 to 69 and the comparative examples 13 to 15. Satisfactory results could be obtained in all the items.

The present invention has been described in detail with respect to preferred embodiments, and it will now be that changes and modifications may be made without departing from the invention in its broader aspects, and it is the invention, therefore, in the appended claims to cover all such changes and modifications as fall within the true spirit of the invention.

What is claimed is:

1. Polyhydroxyalkanoate comprising, in the polymer molecule, a unit represented by the following general formula (1):

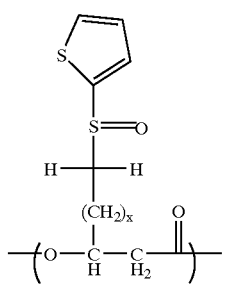

$X = 0-8$ (wherein x stands for an integer selected within a range of 0–8 indicated in the chemical formula, and such unit may be present at least one in the polymer);

a unit represented by the following general formula (2):

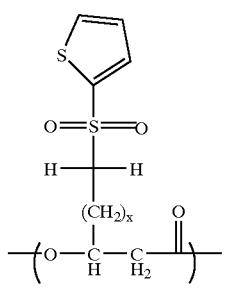

$X = 0-8$ (wherein x stands for an integer selected within a range of 0–8 indicated in the chemical formula, and such unit may be present at least one in the polymer); and at least one of the units represented by the following general formulas (3) to (6), namely:

a unit represented by the following general formula (3):

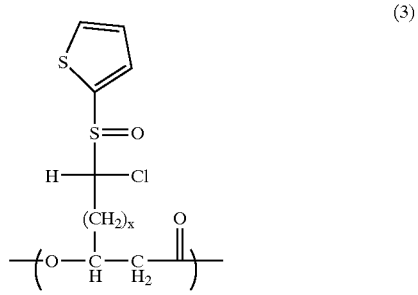

$X = 0-8$ (wherein x stands for an integer selected within a range of 0–8 indicated in the chemical formula, and such unit may be present at least one in the polymer);

a unit represented by the following general formula (4):

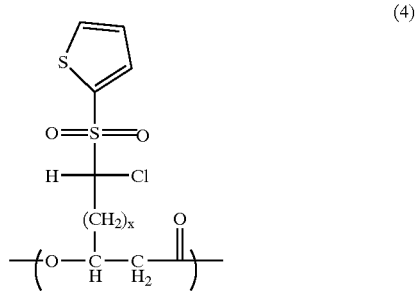

$X = 0-8$ (wherein x stands for an integer selected within a range of 0–8 indicated in the chemical formula, and such unit may be present at least one in the polymer);

a unit represented by the following general formula (5):

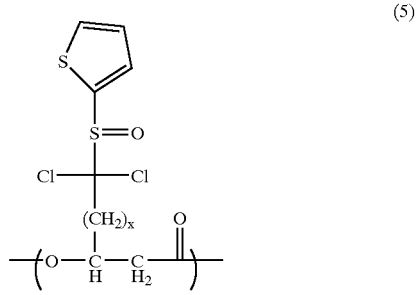

$X = 0-8$ (wherein x stands for an integer selected within a range of 0–8 indicated in the chemical formula, and such unit may be present at least one in the polymer); and a unit represented by the following general formula (6):

(6)

$$\begin{array}{c} \text{thiophene-S(=O)(=O)-C(Cl)(Cl)-(CH}_2)_x\text{-} \\ \text{(-O-CH-CH}_2\text{-C(=O)-)} \end{array}$$

X = 0–8

(wherein x stands for an integer selected within a range of 0–8 indicated in the chemical formula, and such unit may be present at least one in the polymer).

2. Polyhydroxyalkanoate according to claim 1, further comprising, in addition to the unit represented by said general formula (1), the unit represented by said general formula (2) and at least one of the units represented by said general formulas (3) to (6), at least one of:

a unit represented by the following general formula (7):

(7)

$$\text{(-O-CH(-(CH}_2)_y\text{-CH}_3)\text{-CH}_2\text{-C(=O)-)}$$

X = 0–8

(wherein y stands for an integer selected within a range of 0–8 indicated in the chemical formula, and such unit may be present at least one in the polymer); and a unit represented by the following general formula (8):

(8)

$$\text{(-O-CH(-CH}_2\text{-CH=CH-(CH}_2)_z\text{-CH}_3)\text{-CH}_2\text{-C(=O)-)}$$

z = 3, 5

(wherein z stands for an integer selected from 3 and 5).

3. Polyhydroxyalkanoate according to claim 1, having a number average molecular weight within a range of 1000 to 500000.

4. A method for producing polyhydroxyalkanoate according to claim 1, comprising:

(step 1) a step of culturing microorganisms in a culture medium containing at least one of ω-(2-thienylsulfanyl)alkanoic acids represented by the following general formula (27)

(27)

$$\text{thiophene-S-CH}_2\text{-(CH}_2)_x\text{-CH}_2\text{-CH}_2\text{-C(=O)-OH}$$

X = 0–8

(wherein x stands for an integer selected from a range of 0 to 8); and (step 2) a step of processing polyhydroxyalkanoate, produced by the microorganisms cultured in the step 1, with sodium hypochlorite.

5. A producing method according to claim 4, further comprising, between said steps 1 and 2:

a step of separating polyhydroxyalkanoate produced by said microorganisms cultured in the step 1 from the cells of said microorganisms.

6. A producing method according to claim 5, wherein said step of separating polyhydroxyalkanoate produced by said microorganisms includes a step of pulverizing the microorganism cells.

7. A producing method according to claim 5, wherein said step of separating polyhydroxyalkanoate produced by the microorganisms from said cells thereof includes a step of extracting said polyhydroxyalkanoate from the microorganism cells with a solvent capable dissolving polyhydroxyalkanoate produced by the microorganisms.

8. A producing method according to claim 4, wherein the culture medium employed in the step 1 contains polypeptone.

9. A producing method according to claim 4, wherein the culture medium employed in the step 1 contains yeast extract.

10. A producing method according to claim 4, wherein the culture medium employed in the step 1 contains saccharide.

11. A producing method according to claim 10, wherein said saccharide is at least one compound selected from a group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose and lactose.

12. A producing method according to claim 4, wherein the culture medium employed in the step 1 contains an organic acid or a salt thereof.

13. A producing method according to claim 12, wherein said organic acid or salt thereof is at least a compound selected from a group consisting of pyruvic acid, malic acid, lactic acid, citric acid, succinic acid and salts thereof.

14. A producing method according to claim 4, wherein the culture medium employed in the step 1 contains an amino acid or a salt thereof.

15. A producing method according to claim 14, wherein said amino acid or salt thereof is at least a compound selected from a group consisting of glutamic acid, aspartic acid and salts thereof.

16. A producing method according to claim 4, wherein the culture medium employed in the step 1 contains a straight-chain alkanoic acid with 4 to 12 carbon atoms or a salt thereof.

17. A producing method according to claim 4, wherein the culture of microorganisms in said step 1 includes:

(step 1-1) a step of culturing microorganisms in a culture medium containing at least one of ω-(2-thienylsulfanyl)alkanoic acids represented by the following general formula (27)

(27)

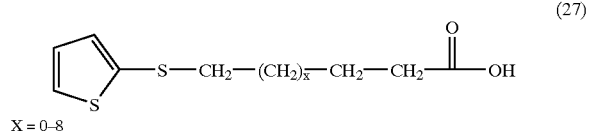

X = 0–8

(wherein x stands for an integer selected from a range of 0 to 8) and polypeptone; and (step 1-2) a step of further culturing the microorganisms, cultured in said step 1-1, in a culture medium containing at least one of ω-(2-thienylsulfanyl)alkanoic acids represented by said general formula (27) and an organic acid or a salt thereof.

18. A producing method according to claim 4, wherein the culture of microorganisms in said step 1 includes:

(step 1-3) a step of culturing microorganisms in a culture medium containing at least one of ω-(2-thienylsulfanyl)alkanoic acids represented by the following general formula (27)

(27)

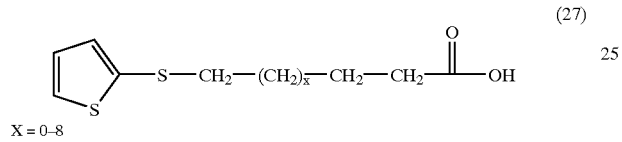

X = 0–8

(wherein x stands for an integer selected from a range of 0–8) and saccharide; and (step 1-4) a step of further culturing the microorganisms, cultured in the step 1-3, in a culture medium containing at least one of ω-(2-thienylsulfanyl)alkanoic acids represented by said general formula (27) and saccharide.

19. A producing method according to claim 4, wherein the microorganisms employed in the step 1 are those belonging to *Pseudomonas* genus.

20. A producing method according to claim 19, wherein said microorganisms employed in the step 1 are those of at least a strain selected from *Pseudomonas cichorii* YN2 (FERM BP-7375), *Pseudomonas cichorii* H45 (FERM BP-7374) and *Pseudomonas jessenii* P161 (FERM BP-7376).

21. In a charge control agent, the improvement wherein the charge control agent comprises a polyhydroxyalkanoate including, in the polymer molecule, a unit represented by the following general formula (1):

(1)

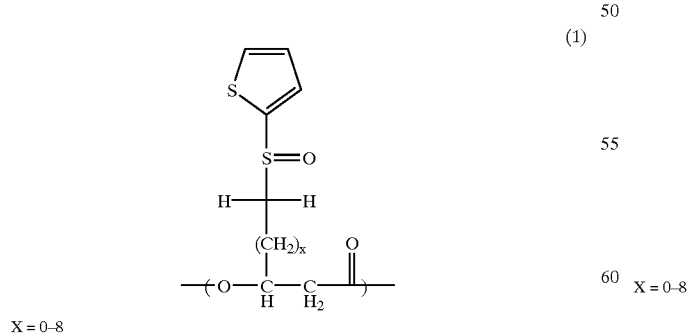

X = 0–8

(wherein x stands for an integer selected within a range of 0–8 indicated in the chemical formula, and such unit may be present at least one in the polymer);

a unit represented by the following general formula (2):

(2)

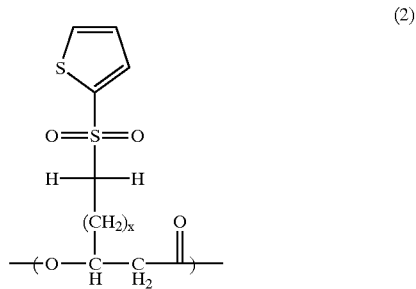

X = 0–8

(wherein x stands for an integer selected within a range of 0–8 indicated in the chemical formula, and such unit may be present at least one in the polymer); and at least one of the units represented by the following general formulas (3) to (6), namely:

a unit represented by the following general formula (3):

(3)

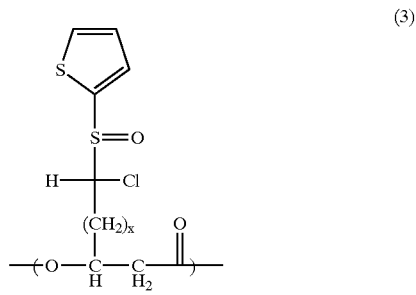

X = 0–8

(wherein x stands for an integer selected within a range of 0–8 indicated in the chemical formula, and such unit may be present at least one in the polymer);

a unit represented by the following general formula (4):

(4)

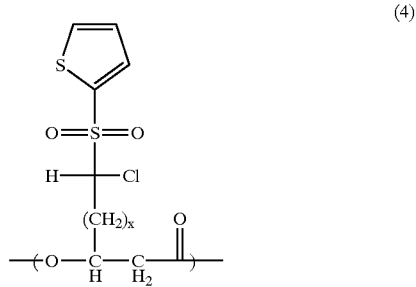

X = 0–8

(wherein x stands for an integer selected within a range of 0–8 indicated in the chemical formula, and such unit may be present at least one in the polymer);

a unit represented by the following general formula (5):

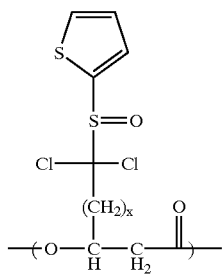

(5)

X = 0–8

(wherein x stands for an integer selected within a range of 0–8 indicated in the chemical formula, and such unit may be present at least one in the polymer); and a unit represented by the following general formula (6):

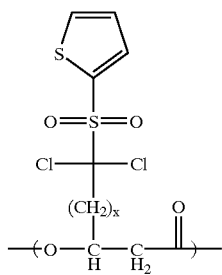

(6)

x = 0–8

(wherein x stands for an integer selected within a range of 0–8 indicated in the chemical formula, and such unit may be present at least one in the polymer).

22. A charge control agent according to claim 21 wherein said polyhydroxyalkanoate further includes, in addition to the unit represented by said general formula (1), the unit represented by said general formula (2) and at least one of the units represented by said general formulas (3) to (6), at least one of:

a unit represented by the following general formula (7):

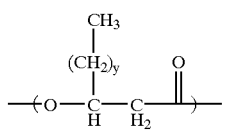

(7)

y = 0–8

(wherein y stands for an integer selected within a range of 0–8 indicated in the chemical formula, and such unit may be present at least one in the polymer); and a unit represented by the following general formula (8):

$$\begin{array}{c} CH_3 \\ | \\ (CH_2)_z \\ | \\ CH \\ \| \\ CH \\ | \\ CH_2 \quad O \\ | \quad \| \\ -\!(\!O\!-\!\underset{H}{C}\!-\!\underset{H_2}{C}\!)\!- \end{array}$$

z = 3, 5

(wherein z stands for an integer selected from 3 and 5) (wherein y and z may assume arbitrary integral values at least equal to 1 within the ranges shown in the chemical formulas, independently from the units represented by (1), (2), (3), (4), (5) and (6)).

23. A charge control agent according to claim 21, wherein said polyhydroxyalkanoate has a number average molecular weight within a range of 1000 to 500000.

24. A toner binder comprising the charge control agent according to claim 21.

25. An electrostatic latent image developing toner comprising, at least, binder resin, a coloring agent, and the charge control agent according to claim 21.

26. An image forming method comprising at least a step of externally applying a voltage to a charging member thereby charging an electrostatic latent image bearing member, a step of forming an electrostatic latent image on the charged electrostatic latent image bearing member, a development step of developing the electrostatic latent image with electrostatic latent image developing toner thereby forming a toner image on the electrostatic latent image bearing member, a transfer step of transferring the toner image on the electrostatic latent image bearing member onto a recording material, and a fixation step of heat fixing the toner image on the recording material;

the method comprising the use of electrostatic latent image developing toner comprising at least a binder resin, a coloring agent, and a charge control agent according to claim 21.

27. An image forming method at least comprising a step of externally applying a voltage to a charging member thereby charging an electrostatic latent image bearing member, a step of forming an electrostatic latent image on the charged electrostatic latent image bearing member, a development step of developing the electrostatic latent image with electrostatic latent image developing toner thereby forming a toner image on the electrostatic latent image bearing member, a first transfer step of transferring the toner image on the electrostatic latent image bearing member onto an intermediate transfer member, a second transfer step of transferring the toner image on the intermediate transfer member onto a recording material, and a fixation step of heat fixing the toner image on the recording material;

the method comprising the use of electrostatic latent image developing toner comprising at least a binder resin, a coloring agent, and a charge control agent according to claim 21.

28. An image forming apparatus comprising formation of an image on a recording material with electrostatic latent image developing toner according to claim 25.

29. An image forming apparatus at least comprising means for externally applying a voltage to a charging member thereby charging an electrostatic latent image bearing member, means for forming an electrostatic latent image on the charged electrostatic latent image bearing member, development means for developing the electrostatic latent image with electrostatic latent image developing toner thereby forming a toner image on the electrostatic latent image bearing member, transfer means for transferring the toner image on the electrostatic latent image bearing member onto a recording material, and fixation means for heat fixing the toner image on the recording material;

the apparatus comprising the use of electrostatic latent image developing toner according to claim 25.

30. An image forming apparatus according to claim 29, comprising at least means for externally applying a voltage to a charging member thereby charging an electrostatic latent image bearing member, means for forming an electrostatic latent image on the charged electrostatic latent image bearing member, development means for developing the electrostatic latent image with electrostatic latent image developing toner thereby forming a toner image on the electrostatic latent image bearing member, first transfer means for transferring the toner image on the electrostatic latent image bearing member onto an intermediate transfer member, second transfer means for transferring the toner image on the intermediate transfer member onto a recording material, and fixation means for heat fixing the toner image on the recording material;

the apparatus comprising the use of electrostatic latent image developing toner.

* * * * *

UNITED STATES PATENT AND TRADEMARK OFFICE
CERTIFICATE OF CORRECTION

PATENT NO. : 6,855,472 B2
DATED : February 15, 2005
INVENTOR(S) : Takeshi Imamura et al.

It is certified that error appears in the above-identified patent and that said Letters Patent is hereby corrected as shown below:

Title page,
Item [56], References Cited, FOREIGN PATENT DOCUMENTS,
"JP          9-2871746          10/1997" should read
-- JP        9-281746           10/1997 --; and
"JP          2001-057085        12/1999" should read
-- JP        2001-057085        02/2001 --.
OTHER PUBLICATIONS,
"Stelnbüchel, et al." reference, "Stelnbüchel," should read -- Steinbüchel --.
"Park, et al." (first occurrence), reference, "Chemistry." should read -- Chemistry, --.
"Gross et al." reference, "Th rmal" should read -- Thermal --.
"Curl y, t al." reference, "Curl y, t al.," should read -- Curley, et al., --;
"Substitu nts" should read -- Substituents --;
"*varans*" should read -- *vorans* --; and
"Macromolecul s," should read -- Macromolecules, --.
"Kim, et al." reference (first occurrence), "Poly(β-hydroxyalkanoat s)" should read -- Poly(β-hydroxyalkanoates) --;
"5-Phenylval ric" should read -- 5-Phenylvaleric --; and
"Macromolecul s," should read -- Macromolecules, --.
"Ritter, et al." reference, "chians," should read -- chains, --.
"Park, et al. reference (second occurrence), "Producation" should read -- Production --.
Item [57], ABSTRACT,
Line 8, "a units" should read -- units --.

Column 1,
Line 13, "novel a" should read -- a novel --; and
Line 21, "2-thienylsulfonyl" should read -- 2-thienylsulfanyl --.

Column 2,
Line 67, "pnenoxyvaleric" should read -- phenoxyvaleric --.

Column 3,
Line 22, "are" should read -- is --; and
Line 30, "stain," should read -- strain, --.

Column 4,
Line 31, "salycilic" should read -- salicylic --; and
Line 34, "tibutyltin" should read -- tributyltin --.

Column 5,
Line 43, "dyestaff" should read -- dyestuff --.

UNITED STATES PATENT AND TRADEMARK OFFICE
CERTIFICATE OF CORRECTION

PATENT NO. : 6,855,472 B2
DATED : February 15, 2005
INVENTOR(S) : Takeshi Imamura et al.

It is certified that error appears in the above-identified patent and that said Letters Patent is hereby corrected as shown below:

Column 23,
Formula (4), that portion of the formula reading "x=0-8" should read -- y=0-8 --.

Column 27,
Line 15, "retain" should read -- retains --.

Column 29,
Line 23, "Advancd" should read -- Advanced --; and
Line 31, "Stain" should read -- Strain --.

Column 30,
Lines 9 and 52, "Stain" should read -- Strain --.

Column 31,
Line 33, "aformentioned" should read -- aforementioned --; and
Line 45, "or reserve" should read -- of reserve --.

Column 32,
Line 27, "generated a" should read -- generated as a --; and
Line 37, "glucronic" should read -- glucuronic --.

Column 35,
Line 6, "bactereia" should read -- bacteria --.

Column 43,
Line 51, "(such" should read -- such --.

Column 45,
Line 21, "isobuty" should read -- isobutyl --; and
Line 42, "1.6-hexanediol," should read -- 1,6-hexanediol, --.

Column 49,
Line 25, "in" (first occurrence) should read -- if --;
Line 29, "othere" should read -- other --; and
Line 40, "caolin;" should read -- kaolin; --.

Column 50,
Line 26, "is" should read -- are --; and
Line 31, "tends" should read -- tend --.

UNITED STATES PATENT AND TRADEMARK OFFICE
CERTIFICATE OF CORRECTION

PATENT NO.    : 6,855,472 B2
DATED         : February 15, 2005
INVENTOR(S)   : Takeshi Imamura et al.

It is certified that error appears in the above-identified patent and that said Letters Patent is hereby corrected as shown below:

<u>Column 52</u>
Line 4, "obtained heating" should read -- obtained by heating --; and
Line 57, "stroke/minute." should read -- strokes/minute. --.

<u>Column 53,</u>
Line 54, "formula 5 (7)" should read -- formula (7) --.

<u>Column 59,</u>
Line 47, "15 to" should read -- 15 to 70. --.

<u>Column 60,</u>
Line 23, "weight-averated" should read -- weight-averaged --; and
Line 30, "Henshell" should read -- Henschel --.

<u>Column 63,</u>
Line 45, "Henshell" should read -- Henschel --; and
Line 49, "pass" should read -- mass --.

<u>Column 65,</u>
Line 67, "Henshell" should read -- Henschel --.

<u>Column 66,</u>
Line 4, "pass" should read -- mass --; and
Line 11, "examples 46' " should read -- examples 46 --.

<u>Column 68,</u>
Line 11, "foam" should read -- from --; and
Line 12, "foamed" should read -- formed --.

<u>Column 69,</u>
Line 35, "toner was observed." should read -- toner. --.

<u>Column 73,</u>
Line 18, "invention," should read -- intention, --.

UNITED STATES PATENT AND TRADEMARK OFFICE
CERTIFICATE OF CORRECTION

PATENT NO.    : 6,855,472 B2
DATED         : February 15, 2005
INVENTOR(S)   : Takeshi Imamura et al.

It is certified that error appears in the above-identified patent and that said Letters Patent is hereby corrected as shown below:

Column 75,
Formula (7), that portion of the formula reading "x=0-8" should read -- y=0-8 --.

Signed and Sealed this

Twenty-first Day of February, 2006

JON W. DUDAS
*Director of the United States Patent and Trademark Office*